(12) United States Patent
Bolli et al.

(10) Patent No.: US 12,410,208 B2
(45) Date of Patent: Sep. 9, 2025

(54) (2-ACETAMIDYL)THIO-BETA-D-GALACTOPYRANOSIDE DERIVATIVES

(71) Applicant: Idorsia Pharmaceuticals Ltd, Allschwil (CH)

(72) Inventors: Martin Bolli, Allschwil (CH); Daniel Bur, Therwil (CH); John Gatfield, Allschwil (CH); Corinna Grisostomi, Allschwil (CH); Lubos Remen, Allschwil (CH); Cornelia Zumbrunn, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 814 days.

(21) Appl. No.: 17/633,941

(22) PCT Filed: Aug. 6, 2020

(86) PCT No.: PCT/EP2020/072197
§ 371 (c)(1),
(2) Date: Feb. 8, 2022

(87) PCT Pub. No.: WO2021/028323
PCT Pub. Date: Feb. 18, 2021

(65) Prior Publication Data
US 2022/0306674 A1    Sep. 29, 2022

(51) Int. Cl.
C07H 19/056    (2006.01)

(52) U.S. Cl.
CPC .................. C07H 19/056 (2013.01)

(58) Field of Classification Search
CPC ................................................ C07H 19/056
See application file for complete search history.

(56) References Cited

U.S. PATENT DOCUMENTS

| | | |
|---|---|---|
| 2014/0099319 A1 | 4/2014 | Traber |
| 2023/0295182 A1 | 9/2023 | Bolli et al. |
| 2023/0348442 A1 | 11/2023 | Bolli et al. |
| 2024/0109930 A1 | 4/2024 | Bolli et al. |
| 2024/0124427 A1 | 4/2024 | Bolli et al. |

FOREIGN PATENT DOCUMENTS

| | | |
|---|---|---|
| WO | WO 02/057284 A1 | 7/2002 |
| WO | WO 2005/113568 A1 | 12/2005 |
| WO | WO 2005/113569 A1 | 12/2005 |
| WO | WO 2014/067986 A1 | 5/2014 |
| WO | WO 2014/078655 A1 | 5/2014 |
| WO | WO 2016/120403 A1 | 8/2016 |
| WO | WO 2017/007689 A1 | 1/2017 |
| WO | WO 2018/011094 A1 | 1/2018 |
| WO | WO 2018/209255 A1 | 11/2018 |
| WO | WO 2018/209276 A1 | 11/2018 |
| WO | WO 2019/067702 A1 | 4/2019 |
| WO | WO 2019/067702 A9 | 4/2019 |
| WO | WO 2019/075045 A1 | 4/2019 |
| WO | WO 2019/089080 A1 | 5/2019 |
| WO | WO 2020/078807 A1 | 4/2020 |
| WO | WO 2020/078808 A1 | 4/2020 |
| WO | WO 2020/104335 A1 | 5/2020 |
| WO | WO 2020/210308 A1 | 10/2020 |
| WO | WO 2021/001528 A1 | 1/2021 |
| WO | WO 2021/004940 A1 | 1/2021 |
| WO | WO 2021/028336 A1 | 2/2021 |
| WO | WO 2021/028570 A1 | 2/2021 |
| WO | WO 2021/038068 A1 | 3/2021 |
| WO | WO 2022/073969 A1 | 4/2022 |
| WO | WO 2022/090544 A1 | 5/2022 |
| WO | WO 2022/171594 A1 | 8/2022 |
| WO | WO 2022/184755 A1 | 9/2022 |

OTHER PUBLICATIONS

Blanchard et al., "Galectin-3 inhibitors: a patent review (2008-present)" Expert Opin Ther Patents vol. 24 No. 10 pp. 1053-1065, DOI:10.1517/13543776.2014.947961 (Year: 2014).*
Rose et al., "Prediction and Prevention of Autoimmune Disease in the 21st Century: A Review and Preview" vol. 183 No. 5 pp. 403-406, DOI: 10.1093/aje/kwv292 (Year: 2016).*
Marcel Verweij, "Preventative Medicine Between Obligation and Aspiration", published by Springer-Science and Business Media, DOI:10.1007/978-94-015-9365-6, pp. 25-48 (Year: 2000).*
Penny et al., "The challenges for cancer chemoprevention" Chem Soc Rev vol. 44, pp. 8836-8847, DOI: 10.1039/c5cs00705d (Year: 2015).*
Li et al., "Functions of Galectin-3 and Its Role in Fibrotic Diseases" The Journal of Pharmacology and Experimental Therapeutics vol. 351, pp. 336-343, DOI:10.1124/jpet.114.218370 (Year: 2014).*
Traber et al., "Therapy of Experimental NASH and Fibrosis with Galectin Inhibitors" PLOS One vol. 8 issue 12 pp. 1-12, DOI:doi: 10.1371/journal.pone.0083481 (Year: 2013).*
Ma et al., "Galectin-3 Inhibition Is Associated with Neuropathic Pain Attenuation after Peripheral Nerve Injury" PLOS One vol. 11 No. 2 e0148792, doi: 10.1371/journal.pone.0148792 (Year: 2016).*

(Continued)

*Primary Examiner* — Eric Olson
(74) *Attorney, Agent, or Firm* — Hoxie & Associates LLC

(57) ABSTRACT

The present invention relates to compounds of Formula (I)

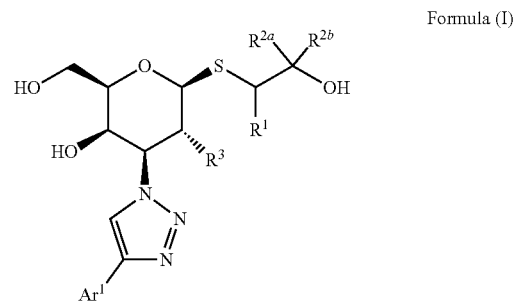

Formula (I)

wherein $Ar^1$, $R^1$, $R^{2a}$, $R^{2b}$, and $R^3$ are as described in the description, their preparation, to pharmaceutically acceptable salts thereof, and to their use as pharmaceuticals, to pharmaceutical compositions containing one or more compounds of Formula (I), and especially to their use as Galectin-3 inhibitors.

15 Claims, No Drawings

(56) References Cited

OTHER PUBLICATIONS

U.S. Appl. No. 17/633,895, filed Feb. 8, 2022 (371(c) Date), Bolli et al.
U.S. Appl. No. 17/634,512, filed Feb. 10, 2022 (371(c) Date), Bolli et al.
U.S. Appl. No. 17/638,799, filed Feb. 25, 2022 (371(c) Date), Bolli et al.
Arciniegas, E. et al., "Galectin-1 and Galectin-3 and Their Potential Binding Partners in the Dermal Thickening of Keloid Tissues," The American Journal of Dermatopathology, 2019, 41 (3), 193-204.
Barondes, S. et al., "Galectins: A Family of Animal β-Galactoside-Binding Lectins," Cell, 1994, 76, 597-598.
Burguillos, M. et al., "Macroglia-Secreted Galectin-3 Acts as a Toll-like Receptor 4 Ligand and Contributes to Microglial Activation," Cell Reports, 2015, 10, 1626-1638.
Caldararu, O. et al., "Are crystallographic β-factors suitable for calculating protein conformational entropy?," Physical Chemistry Chemical Physics, 2019, 21, 18149-18160.
Caniglia, J. et al., "A potential role for Galectin-3 inhibitors in the treatment of COVID-19," PeerJ, 2020, 8:e9392, 10 pages, doi: 10.7717/peerj.9392.
Chasse, T. et al., "Dendritic encapsulation-roles of cores and branches," Tetrahedron, 2003, 59, 3853-3861.
Chen, W-S. et al., "Galectin-3 Inhibition by a Small-Molecule Inhibitor Reduces Both Pathological Corneal Neovascularization and Fibrosis," Investigative Ophthalmology & Visual Science, 2017, 58 (1), 9-20.
Chen, Y-J. et al., "Galectin-3 Enhances Avian H5N1 Influenza A Virus-Induced Pulmonary Inflammation by Promoting NLRP3 Inflammasome Activation," The American Journal of Pathology, 2018, 188 (4), 1031-1042.
Chiariotti, L. et al., "Galectin genes: Regulation of expression," Glycoconjugate Journal, 2004, 19, 441-449.
Dang, Z. et al., "Tubular Atrophy and Interstitial Fibrosis After Renal Transplantation Is Dependent on Galectin-3," Transplantation, 2012, 93 (5), 477-484.
Deroo, E. et al., "The role of galectin-3 and galectin-3-binding protein in venous thrombosis," Blood, 2015, 125 (11), 1813-1821.
Falcone, C. et al., "Galectin-3 Plasma Levels and Coronary Artery Disease: A New Possible Biomarker of Acute Coronary Syndrome," International Journal of Immunopathology and Pharmacology, 2011, 24 (4), 905-913.
Farhad, M. et al., "The role of Galectin-3 in modulating tumor growth and immunosuppression within the tumor microenvironment," OncoImmunology, 2018, 7 (6), e 1434467, 8 pages, https://doi.org/10.1080/2162402X.2018.1434467.
Galectin Therapeutics, "Combination Immunotherapy with Galectin-3 Inhibitor GR-MD-02 Enhances Effects in Pre-clinical Models and Early Results of Phase 1 Clinical Trials," Press Release, dated 2017, 3 pages.
Galectin Therapeutics, "Galectin Therapeutics Announces Results from Phase 2b NASH-CX Trial," Bloomberg, Press Release, dated 2017, 5 pages.
Galecto Biotech, "Galecto Biotech's Lead Molecule TD139 is Safe, Well Tolerated, with Direct Target Engagement and Biomarker Effects in a Clinical Phase Ib/IIa trial in IPF Patients," Press Release, dated 2017, 4 pages.
Gao, P. et al., "Galectin-3: its role in asthma and potential as an anti-inflammatory target," Respiratory Research, 2013, 14:136, 9 pages, doi:10.1186/1465-9921-14-136.
Gehlken, C. et al., "Galectin-3 in Heart Failure: An Update of the Last 3 Years," Heart Failure Clinics, 2018, 14, 75-92.
Giguère, D. et al., "Carbohydrate triazoles and isoxazoles as inhibitors of galectins-1 and -3," Chemical Communications, 2006, 2379-2381.
Greene, T. et al., Eds., Protective Groups in Organic Synthesis, Wiley-Interscience, 1999.
Guha, P. et al., "Cod glycopeptide with picomolar affinity to galectin-3 suppresses T-cell apoptosis and prostate cancer metastasis," Proceedings of the National Academy of Sciences, 2013, 110 (13), 5052-5057.
Henderson, N. et al., "Galectin-3 regulates myofibroblast activation and hepatic fibrosis," Proceedings of the National Academy of Sciences, 2006, 103 (13), 5060-5065.
Henderson, N. et al., "Galectin-3 Expression and Secretion Links Macrophages to the Promotion of Renal Fibrosis," The American Journal of Pathology, 2008, 172 (2), 288-298.
Henderson, N. et al., "The regulation of inflammation by galectin-3," Immunological Reviews, 2009, 230, 160-171.
Hsu, D. et al., "Galectin-3 Expression is Induced in Cirrhotic Liver and Hepatocellular Carcinoma," International Journal of Cancer, 1999, 81, 519-526.
Jin, Q-h. et al., "Serum galectin-3: a risk factor for vascular complications in type 2 diabetes mellitus," Chinese Medical Journal, 2013, 126 (11), 2109-2115.
Johannes, L. et al., "Galectins at a glance," Journal of Cell Science, 2018, 131, jcs208884, 9 pages, doi:10.1242/jcs.208884.
Kikuchi, Y. et al., "Galectin-3-positive call infiltration in human diabetic nephropathy," Nephrology Dialysis Transplantation, 2004, 19 (3), 602-607.
Lacina, L. et al., "Glycophenotype of Psoriatic Skin," Folia Biologica (Praha), 2006, 52, 10-15.
Ladouceur, S et al., "One-Pot Click Synthesis of 1N-Alkyl-4-aryl-1,2,3-triazoles from Protected Arylalkynes and Alkyl Bromides," Synthesis, 2011, 22, 3604-3611.
Leffler, H. et al., "Introduction to galectins," Glycoconjugate Journal, 2004, 19, 433-440.
Li, P. et al., "Hematopoietic-derived Galectin-3 Causes Cellular and Systemic Insulin Resistance," HHS Public Access, Author manuscript, available in PMC 2017, 22 pages, face of article states: Published in final edited form as: Cell, 2016, 167(4), 973-984, doi:10.1016/j.cell.2016.10.025.
Liu, F-T. et al., "Galectins in acute and chronic inflammation," Annals of the New York Academy of Sciences, 2012, 1253, 80-91.
Lowary, T. et al., "Recognition of synthetic O-methyl, epimeric, and amino analogues of the acceptor α-L-Fuc p-(1→2)-β-D-Gal p-OR by the blood-group A and B gene-specified glycosyltransferases," Carbohydrate Research, 1994, 251, 33-67.
MacKinnon, A. et al., "Regulation of Transforming Growth Factor-β1-driven Lung Fibrosis by Galectin-3," American Journal of Respiratory and Critical Care Medicine, 2012, 185 (5), 537-546.
Nachtigal, M. et al., "Galectin-3 Expression in Human Atherosclerotic Lesions," American Journal of Pathology, 1998, 152 (5), 1199-1208.
Nishi, Y. et al., "Role of Galectin-3 in Human Pulmonary Fibrosis," Allergology International, 2007, 56 (1), 57-65.
Noël, J-C. et al., "Galectin-3 is Overexpressed in Various Forms of Endometriosis," Appllied Immunohistochemistry & Molecular Morphology, 2011, 19 (3), 253-257.
Rao, S. et al., "Regulation of Eosinophil Recruitment and Activation by Galectins in Allergic Asthma," Frontiers in Medicine, 2017, 4:68, 12 pages, doi:10.3389/fmed.2017.00068.
Rebholz, C. et al., "Plasma galectin-3 levels are associated with the risk of incident chronic kidney disease," Kidney International, 2018, 93, 252-259.
Remington, The Science and Practice of Pharmacy, 21st Edition, 2005, Part 5, "Pharmaceutical Manufacturing," published by Lippincott Williams & Wilkins.
Ruvolo, P., "Galectin 3 as a guardian of the tumor microenvironment," Biochimica et Biophysica Acta, 2016, 1863, 427-437.
Saegusa J. et al., "Galectin-3 Is Critical for the Development of the Allergic Inflammatory Response in a Mouse Model of Atopic Dermatitis," The American Journal of Pathology, 2009, 174 (3), 922-931.
Sano, H. et al., "Human Galectin-3 Is a Novel Chemoattractant for Monocytes and Macrophages," The Journal of Immunology, 2000, 165 (4), 2156-2164.
Sciacchitano, S. et al., "Galectin-3: One Molecule for an Alphabet of Diseases, from A to Z," International Journal of Molecular Sciences, 2018, 19, 379, 59 pages, doi:10.3390/ijms9020379.

(56) References Cited

OTHER PUBLICATIONS

Sharma, U. et al., "Novel anti-inflammatory mechanisms of N-Acetyl-Ser-Asp-Lys-Pro in hypertension-induced target organ damage," HHS Public Access, Author manuscript, available in PMC 2019, 17 pages, face of article states: Published in final edited form as: *Am J Physiol Heart Circ Physiol.*, 2008, 294(3): H1226-H1232, doi:10.1152/ajpheart.00305.2007.
Stahl, P. et al., Eds., Handbook of Pharmaceutical Salts, Properties, Selection, and Use, Wiley-VCH, 2008.
Sundblad, V. et al., "Regulated expression of galectin-3, a multifunctional glycan-binding protein, in haematopoietic and non-haematopoietic tissues," Histology and Histopathology, 2011, 26, 247-265.
Tanaka, K. et al., "Dianions of Ethyl a-Mercaptoacetate and Ethyl α-Mercaptopropionate: A New Method for an Efficient Synthesis of α, β-Unsaturated Esters from Carbonyl Compounds," Chemistry Letters, 1977, 471-474.
Taniguchi, T. et al., "Serum Levels of Galectin-3: Possible Association with Fibrosis, Aberrant Angiogenesis, and Immune Activation in Patients with Systemic Sclerosis," Journal of Rheumatology, 2012, 39 (3), 539-544.
Thandavarayan, R. et al., "14-3-3 protein regulates Ask1 signaling and protects against diabetic cardiomyopathy," Biochemical Pharmacology, 2008, 75, 1797-1806.
Verteramo, M. et al., "Interplay between Conformational Entropy and Solvation Entropy in Protein-Ligand Binding," Journal of the American Chemical Society, 2019, 141, 2012-2026.
Vuong, L. et al., "An Orally Active Galectin-3 Antagonist Inhibits Lung Adenocarcinoma Growth and Augments Response to PD-L1 Blockade," Cancer Research, 2019, 79 (7), 1480-1492.
Watanabe, H. et al., "Bulky Thiols and Their Coordination Compounds. An Improvement of the Removal Method of Tetrahydropyranyl Group from Thiols and Its Application for Ligand Syntheses," Chemistry Letters, 1996, 999-1000.
Witczak, Z. et al., Eds., Click Chemistry in Glycoscience: New Developments and Strategies, 2013, John Wiley & Sons, Inc., Hoboken, New Jersey.
Wouters, J. et al., Eds., Pharmaceutical Salts and Co-crystals, RSC Publishing, 2012.
Zhong, X. et al., "The role of galectin-3 in heart failure and cardiovascular disease," Clinical and Experimental Pharmacology and Physiology, 2019, 46, 197-203.
De Oliveira, F. et al., "Galectin-3 in autoimmunity and autoimmune diseases," Experimental Biology and Medicine, 2015, 240, 1019-1028.
Park, A-M. et al., "Galectin-3 Plays an Important Role in Innate Immunity to Gastric Infection by *Helicobacter pylori*," Infection and Immunity, 2016, 84 (4), 1184-1193.
Suárez-Fuentetaja, N. et al., "Circulating Galectin-3 Following Heart Transplant: Long-term Dynamics and Prognostic Value," Revista Española de Cardiología, 2019, 72 (11), 899-906.
Tao, C-C. et al., "Galectin-3 promotes Aβ oligomerization and Aβ toxicity in a mouse model of Alzheimer's disease," Cell Death & Differentiation, 2020, 27, 192-209.
U.S. Appl. No. 18/248,007, filed Apr. 5, 2023 (371(c) Date), Bolli et al.
U.S. Appl. No. 18/251,273, filed May 1, 2023 (371(c) Date), Bolli et al.
U.S. Appl. No. 18/264,751, filed Aug. 8, 2023 (371(c) Date), Bolli et al.
U.S. Appl. No. 18/548,833, filed Sep. 1, 2023 (371(c) Date), Bolli et al.

\* cited by examiner

(2-ACETAMIDYL)THIO-BETA-D-GALACTOPYRANOSIDE DERIVATIVES

CROSS REFERENCE TO RELATED APPLICATIONS

This application is the National Stage Entry under 35 U.S.C. § 371 of International Application No. PCT/EP2020/072197 filed Aug. 6, 2020, which claims priority to International Application No. PCT/EP2019/071399 filed Aug. 9, 2019, the contents of each of which are hereby incorporated by reference in their entireties.

The present invention relates to compounds of formula (I) which are galectin-3 inhibitors and their use in the prevention/prophylaxis or treatment of diseases and disorders that are related to galectin-3 binding to natural ligands. The invention also concerns related aspects including processes for the preparation of the compounds, pharmaceutical compositions containing one or more compounds of formula (I), and their medical use as Galectin-3 inhibitors. The compounds of formula (I)) may especially be used as single agents or in combination with one or more therapeutic agents.

Galectins are defined as a protein family based on conserved 3-galactoside-binding sites found within their characteristic ~130 amino acid (aa) carbohydrate recognition domains (CRDs) (Barondes S H et al., Cell 1994; 76, 597-598). Human, mouse and rat genome sequences reveal the existence of at least 16 conserved galectins and galectin-like proteins in one mammalian genome (Leffler H. et al., Glycoconj. J. 2002, 19, 433-440). So far, three galectin subclasses were identified, the prototypical galectins containing one carbohydrate-recognition domain (CRD); the chimaera galectin consisting of unusual tandem repeats of proline- and glycine-rich short stretches fused onto the CRD; and the tandem-repeat-type galectins, containing two distinct CRDs in tandem connected by a linker (Zhong X., Clin Exp Pharmacol Physiol. 2019; 46:197-203). As galectins can bind either bivalently or multivalently, they can e.g. cross-link cell surface glycoconjugates to trigger cellular signaling events. Through this mechanism, galectins modulate a wide variety of biological processes (Sundblad V. et al., Histol Histopathol 2011; 26: 247-265).

Galectin-3 (Gal-3), the only chimaera type in the galectin family, has a molecular weight of 32-35 kDa and consists of 250 amino acid residues in humans, a highly conserved CRD and an atypical N-terminal domain (ND). Galectin-3 is monomeric up to high concentrations (100 µM), but can aggregate with ligands at much lower concentrations, which is promoted by its N-terminal non-CRD region via an oligomerisation mechanism that is not yet completely understood (Johannes, L. et al., Journal of Cell Science 2018; 131, jcs208884).

Gal-3 is widely distributed in the body, but the expression level varies among different organs. Depending on its extracellular or intracellular localization, it can display a broad diversity of biological functions, including immunomodulation, host-pathogen interactions, angiogenesis, cell migration, wound healing and apoptosis (Sundblad V. et al., Histol Histopathol 2011; 26: 247-265). Gal-3 is highly expressed in many human tumours and cell types, such as myeloid cells, inflammatory cells (macrophages, mast cells, neutrophils, T cells, eosinophils, etc.), fibroblasts and cardiomyocytes (Zhong X. et al., Clin Exp Pharmacol Physiol. 2019; 46:197-203), indicating that Gal-3 is involved in the regulation of inflammatory and fibrotic processes (Henderson N C. Et al., Immunological Reviews 2009; 230: 160-171; Sano H. et al., J Immunol. 2000; 165(4):2156-64). Furthermore, Gal-3 protein expression levels are up-regulated under certain pathological conditions, such as neoplasms and inflammation (Chiariotti L. et al., Glycoconjugate Journal 2004 19, 441-449; Farhad M. et al., Oncolmmunology 2018, 7:6, e1434467).

There are multiple lines of evidence supporting functional involvement of Gal-3 in the development of inflammatory/autoimmune diseases, such as asthma (Gao P. et al. Respir Res. 2013, 14:136; Rao S P et al. Front Med (Lausanne) 2017; 4:68), rheumatoid arthritis, multiple sclerosis, diabetes, plaque psoriasis (Lacina L. et al. Folia Biol (Praha) 2006; 52(1-2):10-5) atopic dermatitis (Saegusa J. et al. Am J Pathol. 2009, 174(3):922-31), endometriosis (Noel J C et al. Appl Immunohistochem Mol Morphol. 2011 19(3):253-7), or viral encephalitis (Liu F T et al., Ann N Y Acad Sci. 2012; 1253:80-91; Henderson N C, et al., Immunol Rev. 2009; 230(1):160-71; Li P et al., Cell 2016; 167:973-984). Recently Gal-3 has emerged as a key player of chronic inflammation and organ fibrogenesis development e.g. liver (Henderson N C et al., PNAS 2006; 103: 5060-5065; Hsu D K et al. Int J Cancer. 1999, 81(4):519-26), kidney (Henderson N C et al., Am. J. Pathol. 2008; 172:288-298; Dang Z. et al. Transplantation. 2012, 93(5):477-84), lung (Mackinnon A C et al., Am. J. Respir. Crit. Care Med 2012, 185: 537-546; Nishi Y. et al. Allergol Int. 2007, 56(1):57-65), heart (Thandavarayan R A et al. Biochem Pharmacol. 2008, 75(9):1797-806; Sharma U. et al. Am J Physiol Heart Circ Physiol. 2008; 294(3):H1226-32), as well as the nervous system (Burguillos M A et al. Cell Rep. 2015, 10(9):1626-1638), and in corneal neovascularization (Chen W S. Et al., Investigative Ophthalmology & Visual Science 2017, Vol. 58, 9-20). Additionally, Gal-3 was found to be associated with dermal thickening of keloid tissues (Arciniegas E. et al., The American Journal of dermatopathology 2019; 41(3): 193-204) and systemic sclerosis (SSc) especially with skin fibrosis and proliferative vasculopathy observed in such condition (Taniguchi T. et al. J Rheumatol. 2012, 39(3):539-44). Gal-3 was found to be up-regulated in patient suffering chronic kidney disease (CKD) associated-kidney failure, and especially in those affected by diabetes. Interestingly, data obtained from this patient population showed correlation between Gal-3 upregulation in glomeruli and the observed urinary protein excretion (Kikuchi Y. et al. Nephrol Dial Transplant. 2004, 19(3):602-7). Additionally, a recent prospective study from 2018 demonstrated that higher Gal-3 plasma levels are associated with an elevated risk of developing incident CKD, particularly among hypertension-suffering population (Rebholz C M. et al. Kidney Int. 2018 January; 93(1): 252-259). Gal-3 is highly elevated in cardiovascular diseases (Zhong X. et al. Clin Exp Pharmacol Physiol. 2019, 46(3):197-203), such as atherosclerosis (Nachtigal M. et al. Am J Pathol. 1998; 152(5):1199-208), coronary artery disease (Falcone C. et al. Int J Immunopathol Pharmacol 2011, 24(4):905-13), heart failure and thrombosis (Nachtigal M. et al., Am J Pathol. 1998; 152(5): 1199-208; Gehlken C. et al., Heart Fail Clin. 2018, 14(1): 75-92; DeRoo E P. et al., Blood. 2015, 125(11):1813-21). Gal-3 blood concentration is elevated in obese and diabetic patients and is associated with a higher risk for micro- and macro-vascular complication (such as heart failure, nephropathy/retinopathy, peripheral arterial disease, cerebrovascular event, or myocardial infarction) (Qi-hui-Jin et al. Chin Med J (Engl). 2013,126(11):2109-15). Gal-3 influences oncogenesis, cancer progression, and metastasis (Vuong L. et al., Cancer Res 2019 (79) (7) 1480-1492), and was shown to exert a role as a pro-tumor factor by acting within the micro tumor environment to suppress immune surveillance (Ruvolo P P. et al. Biochim Biophys Acta. 2016 March, 1863(3):427-437; Farhad M. et al. Oncoimmunology 2018 Feb. 20; 7(6):e1434467). Among the cancers that express high level of Gal-3 are found those affecting the thyroid gland, the central nervous system, the tongue, the breast, the gastric cancer, the head and neck squamous cell, the pancreas, the bladder, the kidney, the liver, the parathyroid, the salivary glands, but also lymphoma, carcinoma, non-small cell lung cancer, melanoma and neuroblastoma (Sciacchitano S. et al. Int J Mol Sci 2018 Jan. 26, 19(2): 379).

Also, Gal-3 inhibition has been proposed to be beneficial in the treatment of COVID-19 (Caniglia J L et al. PeerJ 2020, 8:e9392) and influenza H5N1 (Chen Y J et al. Am. J. Pathol. 2018, 188(4), 1031-1042) possibly due to anti-inflammatory effects.

Recently, Gal-3 inhibitors have shown to have positive effects when used in combination immunotherapy (Galectin Therapeutics. Press Release, Feb. 7, 2017) and idiopathic pulmonary fibrosis (Galecto Biotech. Press Release, Mar. 10, 2017) and in NASH cirrhosis (Dec. 5, 2017). WO20180209276, WO2018209255 and WO20190890080 disclose compounds having binding affinity with galectin proteins for the treatment of systemic insulin resistance disorders. Thus, Gal-3 inhibitors, alone or in combination with other therapies, may be useful for the prevention or treatment of diseases or disorders such as fibrosis of organs, cardiovascular diseases and disorders, acute kidney injury and chronic kidney disease, liver diseases and disorders, interstitial lung diseases and disorders, ocular diseases and disorders, cell proliferative diseases and cancers, inflammatory and autoimmune diseases and disorders, gastrointestinal tract diseases and disorders, pancreatic diseases and disorders, abnormal angiogenesis-associated diseases and disorders, brain-associated diseases and disorders, neuropathic pain and peripheral neuropathy, and/or transplant rejection.

Several publications and patent applications describe synthetic inhibitors of Gal-3 that are being explored as antifibrotic agents (see for example WO2005113568, WO2005113569, WO2014067986, WO2016120403, US20140099319, WO2019067702, WO2019075045, WO2014078655, WO2020078807 and WO2020078808).

Verteramo et al. (J. Am. Chem. Soc. 2019, 141, 5, 2012) discloses a comparative analysis of ligand binding to galectin-3C using two diastereomeric 3-D-galactopyranoside ligands, which however are different from the present compounds by at least the absence of present mandatory substituent $R^1$. The same ligand was used by Caldararu et al. (Phys. Chem. Chem. Phys. 2019, 21, 18149) to study whether it is possible to obtain reliable entropies from crystallographic B-factors.

The present invention provides novel compounds of formula (I) which are Galectin-3 inhibitors. The present compounds may, thus, be useful for the prevention/prophylaxis or treatment of diseases and disorders where modulation of Gal-3 binding to its natural carbohydrate ligands is indicated.

1) In a first embodiment, the invention relates to a compound of the Formula (I),

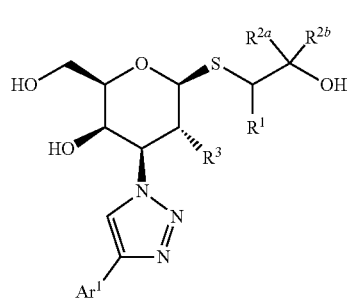

Formula (I)

wherein
$R^1$ represents
an amide group of the structure:

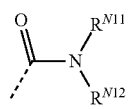

wherein
$R^{N11}$ represents
—$C_{1-6}$-alkyl;
—$CH_2$—$CH_2$—$CH_{1-3}$-alkyl;
—$CH_2$—$C_{1-3}$-fluoroalkyl (especially —$CH_2$—$CF_3$ or —$CH_2$—$C(CH_3)_2F$);
—$C_{0-2}$-alkylene-$C_{3-6}$-cycloalkyl, wherein said $C_{3-6}$-cycloalkyl is unsubstituted or mono- or di-substituted with fluoro or methyl;
—$C_{0-2}$-alkylene-$C_{4-6}$-cycloalkyl wherein said $C_{4-6}$-cycloalkyl contains one oxygen ring atom;
—$CH_2$—$CH_2$—$NR^{N21}R^{N22}$, wherein $R^{N21}$ and $R^{N22}$ together with the nitrogen atom to which they are attached form a 4- to 6-membered heterocyclyl selected from azetidine-1-yl, pyrrolidine-1-yl, piperidine-1-yl, and morpholin-4-yl (especially morpholin-4-yl); or
—$C_{1-2}$-alkylene-$R^{11}$, wherein $R^{11}$ represents phenyl or 5- or 6-membered heteroaryl (especially thiophenyl, pyridinyl, imidazolyl) wherein said phenyl or 5- or 6-membered heteroaryl independently is unsubstituted or mono-substituted with methyl; phenyl or 5- or 6-membered heteroaryl (especially pyridinyl) wherein said phenyl or 5- or 6-membered heteroaryl independently is unsubstituted or mono-substituted with methyl; or

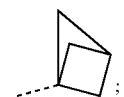

and $R^{N12}$ represents hydrogen or $C_{1-2}$-alkyl;
or $R^{N11}$ and $R^{N12}$ together with the nitrogen atom to which they are attached form a 4- to 6-membered heterocyclyl selected from azetidine-1-yl, pyrrolidine-1-yl, and piperidine-1-yl, wherein said 4- to 6-membered heterocyclyl independently is unsubstituted, mono-, or di-substituted, wherein the substituents independently are methyl or fluoro;
or $R^{N11}$ and $R^{N12}$ together with the nitrogen atom to which they are attached form morpholin-4-yl;

or $R^{N11}$ and $R^{N12}$ together with the nitrogen atom to which they are attached to form a partially aromatic bicyclic ring consisting of a pyrrolidine-1-yl or a piperidine-1-yl, wherein said pyrrolidine or piperidine is fused to a phenyl ring; (especially said bicyclic ring is indolin-1-yl);

$Ar^1$ represents aryl (especially phenyl) which is mono-, di-, tri-, tetra-, or penta-substituted (especially mono-, di-, or tri-substituted), wherein the substituents are independently selected from halogen, methyl, cyano, and methoxy; [wherein in particular at least one of said substituents is attached in a meta- or in para-position of said phenyl; wherein, if present, such substituent in para-position is preferably selected from halogen, methyl, cyano, and methoxy; and, if present, such substituent in meta-position is preferably halogen]; or 5- or 6-membered heteroaryl (especially thiazolyl or pyridinyl), wherein said 5- or 6-membered heteroaryl independently is unsubstituted, mono- or di-substituted, wherein the substituents are independently selected from halogen, methyl, cyano, and methoxy;

$R^{2a}$ represents hydrogen; and $R^{2b}$ represents

—$C_{2-4}$-alkyl (especially ethyl),

—$C_{0-1}$-alkylene-$Ar^{2b}$, wherein $Ar^{2b}$ represents phenyl or 5- or 6-membered heteroaryl (especially 1H-pyrazole-3-yl), wherein said phenyl or 5- or 6-membered heteroaryl independently is unsubstituted, mono- or di-substituted with methyl;

or $R^{2a}$ and $R^{2b}$ both represent hydrogen, methyl, ethyl, or n-propyl;

or $R^{2a}$ and $R^{2b}$ together with the carbon atom to which they are attached form a 3- to 6-membered ring selected from $C_{3-6}$-cycloalkylene, wherein said Cm-cycloalkylene independently is unsubstituted, mono-, or di-substituted, wherein the substituents independently are methyl or fluoro; tetrahydro-2H-pyran-4,4-diyl, which is unsubstituted, di-, or tetra-substituted with methyl; or piperidine-4,4-diyl, pyrrolidine-3,3-diyl, or azetidine-3,3-diyl wherein the nitrogen of said piperidine, pyrrolidine or azetidine independently is unsubstituted, or substituted with —$C_{1-3}$-alkyl, —$C_{0-2}$-alkylene-$C_{3-6}$-cycloalkyl, or -L-$R^{N2}$ wherein -L- represents —CO—, —$SO_2$—, *—CO—NH—, *—CO—O—, or *—$SO_2$—NH—, and $R^{N2}$ represents —$C_{1-3}$-alkyl or —$C_{0-2}$-alkylene-$C_{3-6}$-cycloalkyl;

(especially said piperidine is unsubstituted or substituted with methyl, —CO-methyl, —CO—O-methyl, —CO—NH-cyclopropyl, —$SO_2$-methyl, —$SO_2$-cyclopropyl, or —$SO_2$—NH-methyl; and said azetidine is substituted with —CO—O-methyl);

wherein in the above groups the asterisks indicate the bond which is connected to the rest of the molecule; or $R^{2a}$ and $R^{2b}$ together with the carbon atom to which they are attached form a spiro-bicyclic ring system of the structure ($S^{2AB}$)

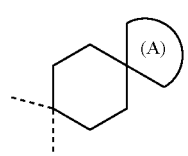

($S^{2AB}$)

wherein ring (A) represents a 3- to 6-membered non-aromatic carbocyclic ring, wherein said 3- to 6-membered non-aromatic carbocyclic ring optionally contains one ring oxygen atom and wherein said 3- to 6-membered non-aromatic carbocyclic ring is unsubstituted or di-substituted with fluoro; and $R^3$ represents hydroxy or $C_{1-3}$-alkoxy (especially methoxy).

The compounds of Formula (I) contain five stereogenic or asymmetric centers, which are situated on the tetrahydropyran moiety and which are in the absolute configuration as drawn for Formula (I). In addition, the compounds of Formula (I) contain at least one, and possibly more, further stereogenic or asymmetric centers, such as one or more additional asymmetric carbon atoms. The compounds of Formula (I) may thus be present as mixtures of stereoisomers or preferably as pure stereoisomers. Mixtures of stereoisomers may be separated in a manner known to a person skilled in the art.

In case a particular compound (or generic structure) is designated as being in a certain absolute configuration, e.g. as (R)- or (S)-enantiomer, such designation is to be understood as referring to the respective compound (or generic structure) in enriched, especially essentially pure, enantiomeric form. Likewise, in case a specific asymmetric center in a compound is designated as being in (R)- or (S)-configuration or as being in a certain relative configuration, such designation is to be understood as referring to the compound that is in enriched, especially essentially pure, form with regard to the respective configuration of said asymmetric center.

The term "enriched", when used in the context of stereoisomers, is to be understood in the context of the present invention to mean that the respective stereoisomer is present in a ratio of at least 70:30, especially of at least 90:10 (i.e., in a purity of at least 70% by weight, especially of at least 90% by weight), with regard to the respective other stereoisomer/the entirety of the respective other stereoisomers.

The term "essentially pure", when used in the context of stereoisomers, is to be understood in the context of the present invention to mean that the respective stereoisomer is present in a purity of at least 95% by weight, especially of at least 99% by weight, with regard to the respective other stereoisomer/the entirety of the respective other stereoisomers.

The present invention also includes isotopically labelled, especially $^2H$ (deuterium) labelled compounds of Formula (I) according to embodiments 1) to 25), which compounds are identical to the compounds of Formula (I) except that one or more atoms have each been replaced by an atom having the same atomic number but an atomic mass different from the atomic mass usually found in nature. Isotopically labelled, especially $^2H$ (deuterium) labelled compounds of formulae (I), (II) and (III) and salts thereof are within the scope of the present invention. Substitution of hydrogen with the heavier isotope $^2H$ (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of Formula (I) are not isotopically labelled, or they are labelled only with one or more deuterium atoms. In a sub-embodiment, the compounds of Formula (I) are not isotopically labelled at all. Isotopically labelled compounds of Formula (I) may be prepared in analogy to the methods described hereinafter, but using the appropriate isotopic variation of suitable reagents or starting materials.

In this patent application, a bond drawn as a dotted line shows the point of attachment of the radical drawn. For example, the radical drawn below

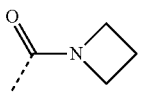

is an azetidine-1-carbonyl group.

Where the plural form is used for compounds, salts, pharmaceutical compositions, diseases and the like, this is intended to mean also a single compound, salt, or the like.

Any reference to compounds of Formula (I) according to embodiments 1) to 25) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example "Handbook of Pharmaceutical Salts. Properties, Selection and Use.", P. Heinrich Stahl, Camille G. Wermuth (Eds.), Wiley-VCH, 2008; and "Pharmaceutical Salts and Co-crystals", Johan Wouters and Luc Quere (Eds.), RSC Publishing, 2012.

Definitions provided herein are intended to apply uniformly to the compounds of Formula (I), as defined in any one of embodiments 1) to 19), and, *mutatis mutandis*, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

In this patent application, the compounds are named using IUPAC nomenclature, but can also be named using carbohydrate nomenclature. Thus, the moiety:

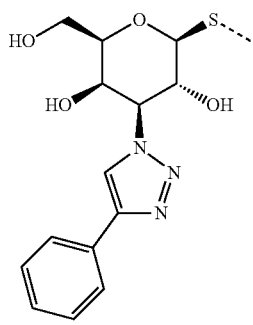

can be named (2S,3R,4S,5R,6R)-3,5-dihydroxy-6-(hydroxymethyl)-4-(4-phenyl-1H-1,2,3-triazol-1-yl)tetrahydro-2H-pyran-2-thiyl or, alternatively, 1,3-di-deoxy-3-[4-phenyl-1H-1,2,3-triazol-1-yl]-8-D-galactopyranoside-1-thiyl, wherein the absolute configuration of carbon atom carrying sulphur atom which is the point of attachment to the rest of the molecule is in (2S)—, respectively, beta-configuration.

For example, compound (S)-2-(1-(Cyclopropylsulfonyl)-4-hydroxypiperidin-4-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-N-methylacetamide is to be understood as also referring to: 1,3-di-deoxy-1-((2-(1-(cyclopropylsulfonyl)-4-hydroxypiperidin-4-yl)-N-ethyl-N-methylacetamide)-(S)-thio)-3-[4-(3,4,5-trifluorophenyl)-1H-1,2,3-triazol-1-yl]-β-D-galactopyranoside.

Whenever a substituent is denoted as optional, it is understood that such substituent may be absent (i.e. the respective residue is unsubstituted with regard to such optional substituent), in which case all positions having a free valency (to which such optional substituent could have been attached to; such as for example in an aromatic ring the ring carbon atoms and/or the ring nitrogen atoms having a free valency) are substituted with hydrogen where appropriate. Likewise, in case the term "optionally" is used in the context of (ring) heteroatom(s), the term means that either the respective optional heteroatom(s), or the like, are absent (i.e. a certain moiety does not contain heteroatom(s)/is a carbocycle/or the like), or the respective optional heteroatom(s), or the like, are present as explicitly defined. If not explicitly defined otherwise in the respective embodiment or claim, groups defined herein are unsubstituted.

The term "halogen" means fluorine, chlorine, or bromine, preferably fluorine or chlorine.

The term "alkyl", used alone or in combination, refers to a saturated straight or branched chain hydrocarbon group containing one to six carbon atoms. The term "$C_{x-y}$-alkyl" (x and y each being an integer), refers to an alkyl group as defined before, containing x to y carbon atoms. For example, a $C_{1-6}$-alkyl group contains from one to six carbon atoms. Representative examples of alkyl groups are methyl, ethyl, propyl, isopropyl, butyl, isobutyl, tert.-butyl, pentyl, 3-methyl-butyl, 2,2-dimethyl-propyl and 3,3-dimethyl-butyl. For avoidance of any doubt, in case a group is referred to as e.g. propyl or butyl, it is meant to be n-propyl, respectively n-butyl. In case $R^{N11}$ represents "—$C_{1-6}$-alkyl", the term preferably means methyl, ethyl, isopropyl, isobutyl, pent-3-yl, 2,2-dimethyl-propyl or 3,3-dimethyl-butyl.

The term "—$C_{x-y}$-alkylene-", used alone or in combination, refers to bivalently bound alkyl group as defined before containing x to y carbon atoms. The term "—$C_{0-y}$-alkylene-" refers to a direct bond, or to a —($C_{1-y}$)alkylene- as defined before. Preferably, the points of attachment of a —$C_{1-y}$-alkylene group are in 1,1-diyl, or in 1,2-diyl, or in 1,3-diyl arrangement. Preferably, the points of attachment of a —$C_{2-y}$-alkylene group are in 1,2-diyl or in 1,3-diyl arrangement. In case a $C_{0-y}$-alkylene group is used in combination with another substituent, the term means that either said substituent is linked through a $C_{1-y}$-alkylene group to the rest of the molecule, or it is directly attached to the rest of the molecule (i.e. a $C_0$-alkylene group represents a direct bond linking said substituent to the rest of the molecule). The alkylene group —$C_2H_4$— refers to —$CH_2$—$CH_2$— if not explicitly indicated otherwise.

The term "alkenyl", used alone or in combination, refers to a straight or branched hydrocarbon chain containing two to five carbon atoms and one carbon-carbon double bond. The term "$C_{x-y}$-alkenyl" (x and y each being an integer), refers to an alkenyl group as defined before containing x to y carbon atoms. For example, a $C_{2-5}$-alkenyl group contains from two to five carbon atoms.

The term "fluoroalkyl", used alone or in combination, refers to an alkyl group as defined before containing one to three carbon atoms in which one or more (and possibly all)

hydrogen atoms have been replaced with fluorine. The term "$C_{x-y}$-fluoroalkyl" (x and y each being an integer) refers to a fluoroalkyl group as defined before containing x to y carbon atoms. For example, a $C_{1-3}$-fluoroalkyl group contains from one to three carbon atoms in which one to seven hydrogen atoms have been replaced with fluorine. Representative examples of fluoroalkyl groups include trifluoromethyl, 2-fluoroethyl, 2,2-difluoroethyl and 2,2,2-trifluoroethyl. Preferred are $C_1$-fluoroalkyl groups such as trifluoromethyl.

The term "fluoroalkoxy", used alone or in combination, refers to an alkoxy group as defined before containing one to three carbon atoms in which one or more (and possibly all) hydrogen atoms have been replaced with fluorine. The term "$C_{x-y}$-fluoroalkoxy" (x and y each being an integer) refers to a fluoroalkoxy group as defined before containing x to y carbon atoms. For example, a $C_{1-3}$-fluoroalkoxy group contains from one to three carbon atoms in which one to seven hydrogen atoms have been replaced with fluorine. Representative examples of fluoroalkoxy groups include trifluoromethoxy, difluoromethoxy, 2-fluoroethoxy, 2,2-difluoroethoxy and 2,2,2-trifluoroethoxy.

The term "cycloalkyl", used alone or in combination, refers especially to a saturated monocyclic, or to a fused-, bridged-, or spiro-bicyclic hydrocarbon ring containing three to eight carbon atoms. The term "$C_{x-y}$-cycloalkyl" (x and y each being an integer), refers to a cycloalkyl group as defined before containing x toy carbon atoms. For example, a $C_{3-6}$-cycloalkyl group contains from three to six carbon atoms. Examples of cycloalkyl groups are cyclopropyl, cyclobutyl, cyclopentyl, cyclohexyl, and cycloheptyl.

The term "$C_{x-y}$-cycloalkyl containing a ring oxygen atom" refers to a cycloalkyl group as defined before containing x to y carbon atoms, wherein one ring carbon atom of said $C_{x-y}$-cycloalkyl is replaced by an oxygen atom. Such groups are unsubstituted or substituted as explicitly defined. Examples are especially oxetanyl, tetrahydrofuranyl, and tetrahydropyranyl. A particular "$C_{4-6}$-cycloalkyl, wherein said Cm-cycloalkyl contains one ring oxygen atom" is tetrahydro-2H-pyran-4-yl.

The term "—$C_{x-y}$-cycloalkylene-", used alone or in combination, refers to bivalently bound cycloalkyl group as defined before containing x to y carbon atoms. Preferably, the points of attachment of any bivalently bound cycloalkyl group are in 1,1-diyl arrangement. Examples are cyclopropan-1,1-diyl, cyclobutan-1,1-diyl, cyclopentan-1,1-diyl; and cyclohexan-1,1-diyl, preferred is cyclohexan-1,1-diyl. In case "$R^{2a}$ and $R^{2b}$ together with the carbon atom to which they are attached form a $C_{3-6}$-cycloalkylene, wherein said $C_{3-6}$-cycloalkylene independently is unsubstituted, mono-, or di-substituted", the term especially refers to the above-listed groups which are unsubstituted or substituted as explicitly defined; particular examples are cyclobutane-1,1-diyl, cyclopentane-1,1-diyl, cyclohexane-1,1-diyl, 3,3-difluorocyclobutane-1,1-diyl, 4,4-dimethylcyclohexane-1,1-diyl, or 4,4-difluorocyclohexane-1,1-diyl; especially 4,4-difluorocyclohexane-1,1-diyl.

The term "alkoxy", used alone or in combination, refers to an alkyl-O— group wherein the alkyl group is as defined before. The term "$C_{x-y}$-alkoxy" (x and y each being an integer) refers to an alkoxy group as defined before containing x to y carbon atoms. Preferred are ethoxy and especially methoxy. In case $R^3$ represents "$C_{1-3}$-alkoxy". the term preferably means methoxy or ethoxy, especially methoxy.

The term "heterocyclyl", used alone or in combination, and if not explicitly defined in a broader or more narrow way, refers to a saturated or unsaturated non-aromatic monocyclic hydrocarbon ring containing one or two ring heteroatoms independently selected from nitrogen, sulfur, and oxygen (especially one oxygen atom, one sulfur atom, one nitrogen atom, two nitrogen atoms, two oxygen atoms, one nitrogen atom and one oxygen atom). The term "$C_{x-y}$-heterocyclyl" refers to such a heterocycle containing x to y ring atoms. Heterocyclyl groups are unsubstituted or substituted as explicitly defined.

The term "aryl", used alone or in combination, means phenyl or naphthyl, preferably phenyl, wherein said aryl group is unsubstituted or substituted as explicitly defined.

The term "heteroaryl", used alone or in combination, and if not explicitly defined in a broader or more narrow way, means a 5- to 10-membered monocyclic or bicyclic aromatic ring containing one to a maximum of four heteroatoms, each independently selected from oxygen, nitrogen and sulfur. Representative examples of such heteroaryl groups are 5-membered heteroaryl groups such as furanyl, oxazolyl, isoxazolyl, oxadiazolyl, thiophenyl, thiazolyl, isothiazolyl, thiadiazolyl, pyrrolyl, imidazolyl, pyrazolyl, triazolyl, tetrazolyl; 6-membered heteroaryl groups such as pyridinyl, pyrimidinyl, pyridazinyl, pyrazinyl; and 8- to 10-membered bicyclic heteroaryl groups such as indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzoxadiazolyl, benzothiadiazolyl, thienopyridinyl, quinolinyl, isoquinolinyl, naphthyridinyl, cinnolinyl, quinazolinyl, quinoxalinyl, phthalazinyl, pyrrolopyridinyl, pyrazolopyridinyl, pyrazolopyrimidinyl, pyrrolopyrazinyl, imidazopyridinyl, imidazopyridazinyl, and imidazothiazolyl. The above-mentioned heteroaryl groups are unsubstituted or substituted as explicitly defined For the substituent $R^{11}$ representing "5- or 6-membered heteroaryl", the term especially means thiophenyl, pyridinyl, imidazolyl; in particular thiophen-2-yl, pyridine-2-yl, 1H-imidazol-4-yl. In case $R^{N11}$ represents "5- or 6-membered heteroaryl", the term means the above-listed groups, especially pyridinyl; in particular pyridin-2-yl or pyridin-3-yl; wherein said 5- or 6-membered heteroaryl group is unsubstituted or substituted as explicitly defined. In case Art represents "5- or 6-membered heteroaryl", the term means the above-listed groups, especially pyridinyl or thiazolyl; in particular thiazol-2-yl or pyridin-3-yl; wherein said 5- or 6-membered heteroaryl group is unsubstituted or substituted as explicitly defined.

In case $R^{2a}$ and $R^{2b}$ together with the carbon atom to which they are attached form a "spiro-bicyclic ring system of the structure ($S^{2AB}$)", such structure ($S^{2AB}$) especially refers to the following structures:

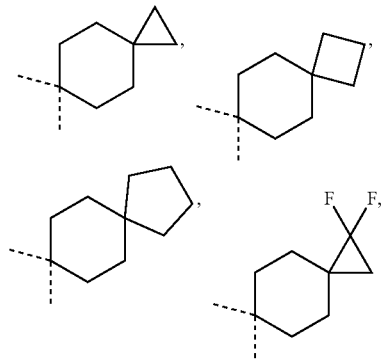

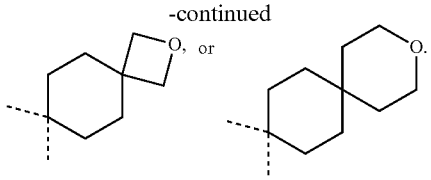

The term "cyano" refers to a group —CN.

The term "oxo" refers to a group =O which is preferably attached to a chain or ring carbon or sulfur atom as for example in a carbonyl group —(CO)—, or a sulfonyl group —(SO₂)—.

Examples of bicyclic rings where "$R^{N11}$ and $R^{N12}$ together with the nitrogen atom to which they are attached to form a partially aromatic bicyclic ring consisting of a pyrrolidine-1-yl or a piperidine-1-yl, wherein said pyrrolidine or piperidine is fused to a phenyl ring" are indolin-1-yl, isoindolin-2-yl, 3,4-dihydroisoquinolin-2(1H)-yl, and 3,4-dihydroquinolin-1(2H)-yl, especially indolin-1-yl.

Examples of heterocyclyl where "$R^{N11}$ and $R^{N12}$ together with the nitrogen atom to which they are attached form a 4- to 6-membered heterocyclyl selected from azetidin-1-yl, pyrrolidin-1-yl, and piperidin-1-yl, wherein said 4- to 6-membered heterocyclyl independently is unsubstituted, mono-, or di-substituted, wherein the substituents independently are methyl or fluoro" are especially azetidin-1-yl which is unsubstituted, or mono-substituted in position 2 or 3 with methyl, or di-substituted in position 3 with fluoro; pyrrolidin-1-yl which is unsubstituted, or di-substituted in position 3 with fluoro; piperidin-1-yl which is unsubstituted, or di-substituted in position 3 or 4 with fluoro.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1,2,3, or 4.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C. Besides, the term "room temperature" as used herein refers to a temperature of about 25° C.

Further embodiments of the invention are presented hereinafter:

2) A second embodiment relates to the compounds of Formula (I) according to embodiment 1) which are also compounds of Formula ($I_s$),

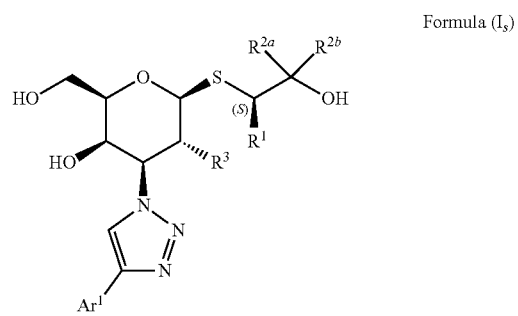

Formula ($I_s$)

wherein the carbon atom to which the group $R^1$ is attached is in the absolute configuration as drawn in Formula (Is) [i.e. it is in absolute (S)-configuration];
wherein $R^1$, $R^{2a}$, $R^{2b}$, $R^3$ and $Ar^1$ are as defined in embodiment 1).

3) Another embodiment relates to compounds according to embodiments 1) or 2), wherein $Ar^1$ represents phenyl which is mono-, di- or tri-substituted, wherein the substituents are independently selected from halogen, methyl, cyano, and methoxy;
wherein at least one of said substituents is attached in a meta- or in para-position of said phenyl,
  wherein, if present, the substituent in para-position is preferably selected from halogen, methyl, cyano, and methoxy; and
  wherein, if present, the substituent in meta-position is preferably halogen.

4) Another embodiment relates to compounds according to embodiments 1) or 2), wherein Art represents phenyl which is mono-, di- or tri-substituted, wherein
  one of said substituents is attached in meta-position of said phenyl, wherein said substituent is halogen; and the remaining substituent(s), if present, is l are halogen (especially fluoro); or
  one of said substituents is attached in para-position of said phenyl, wherein said substituent is independently selected from methyl, cyano, and methoxy; and
  the remaining substituent(s), if present, is l are halogen (especially fluoro).

5) Another embodiment relates to compounds according to embodiments 1) or 2), wherein $Ar^1$ represents a phenyl group of the structure

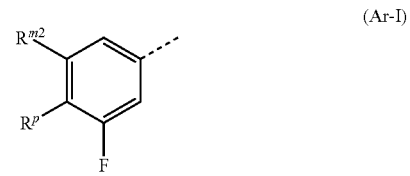

(Ar-I)

wherein
  $R^{m2}$ represents hydrogen or fluoro; and
  $R^p$ represents independently halogen (especially fluoro or chloro), methyl, cyano, or methoxy (notably $R^p$ represents fluoro, chloro, or methyl); or
  $R^{m2}$ represents hydrogen or fluoro; and
  $R^p$ represents hydrogen.

6) Another embodiment relates to compounds according to embodiments 1) or 2), wherein Ar$^1$ represents a phenyl group of the structure

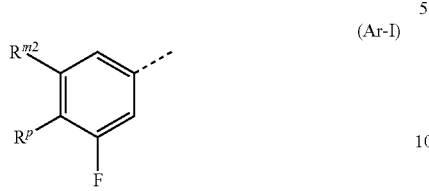

(Ar-I)

wherein
R$^{m2}$ represents halogen (especially fluoro); and
R$_p$ represents hydrogen, halogen (especially fluoro or chloro), methyl, cyano, or methoxy (notably R$^p$ represents fluoro, chloro, or methyl).

7) Another embodiment relates to compounds according to embodiments 1) or 2), wherein Ar$^1$ represents

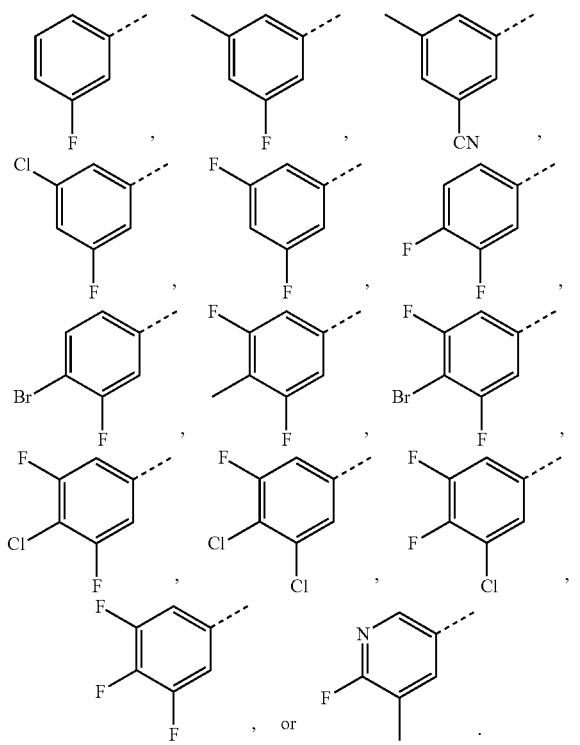

In a sub-embodiment of embodiment 7), Ar$^1$ represents 3,4,5-trifluorophenyl.

8) Another embodiment relates to compounds according to embodiments 1) to 7), wherein R$^1$ represents an amide group of the structure

wherein
R$^{N11}$ represents
—C$_{1-6}$-alkyl (especially methyl, ethyl, isobutyl, 2,2-dimethylprop-1-yl, or 3,3-dimethylbut-1-yl);
—CH$_2$—CH$_2$—O—C$_{1-3}$-alkyl;
—CH$_2$C$_{1-3}$-fluoroalkyl (especially —CH$_2$—CF$_3$ or —CH$_2$—C(CH$_3$)$_2$F);
cyclopropyl, cyclobutyl, —CH$_2$-cyclopropyl, —CH$_2$-cyclopentyl, —CH$_2$-1-fluorocyclopentyl, or —CH$_2$—CH$_2$-cyclopropyl;
3,3-difluorocyclobutyl, —CH$_2$-3,3-difluorocyclobutyl or 4,4-dimethylcyclohexyl;
—CH$_2$-tetrahydro-2H-pyran-4-yl, or —CH$_2$—CH$_2$-tetrahydro-2H-pyran-4-yl;
tetrahydro-2H-pyran-4-yl, or oxetane-3-yl;
—CH$_2$—CH$_2$-morpholin-4-yl; or
—CH$_2$-thiophenyl, —CH$_2$-pyridinyl, benzyl, or —CH$_2$-1-methyl-1H-imidazol-4-yl;
phenyl, or pyridinyl; or

and R$^{N12}$ represents hydrogen or C$_{1-2}$-alkyl (especially methyl).
or R$^{N11}$ and R$^{N12}$ together with the nitrogen atom to which they are attached form a 4- to 6-membered heterocyclyl selected from azetidin-1-yl which is unsubstituted, or mono-substituted in position 2 or 3 with methyl, or di-substituted in position 3 with fluoro; pyrrolidin-1-yl which is unsubstituted, or di-substituted in position 3 with fluoro; and piperidin-1-yl which is unsubstituted, or di-substituted in position 3 or 4 with fluoro or methyl;
or R$^{N11}$ and R$^{N12}$ together with the nitrogen atom to which they are attached form morpholin-4-yl;
or R$^{N11}$ and R$^{N12}$ together with the nitrogen atom to which they are attached to form an indolin-1-yl, isoindolin-2-yl, 3,4-dihydroisoquinolin-2(1H)-yl, or 3,4-dihydroquinolin-1(2H)-yl ring (especially indolin-1-yl).

9) Another embodiment relates to compounds according to embodiments 1) to 7), wherein R$^1$ represents an amide group of the structure

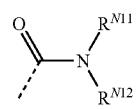

wherein
R$^{N11}$ represents
C$_{1-6}$-alkyl (especially methyl, ethyl, isobutyl, 2,2-dimethylprop-1-yl, or 3,3-dimethylbut-1-yl);
—CH$_2$—C$_{1-3}$-fluoroalkyl (especially —CH$_2$—CF$_3$ or —CH$_2$—C(CH$_3$)$_2$F);
cyclopropyl, cyclobutyl, —CH$_2$-cyclopropyl, —CH$_2$-cyclopentyl, —CH$_2$-1-fluorocyclopentyl, or —CH$_2$—CH$_2$-cyclopropyl;
—CH$_2$-3,3-difluorocyclobutyl;
—CH$_2$-tetrahydro-2H-pyran-4-yl, or —CH$_2$—CH$_2$-tetrahydro-2H-pyran-4-yl;
tetrahydro-2H-pyran-4-yl, or oxetane-3-yl;
benzyl;
phenyl, or pyridinyl; or

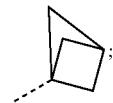

and $R^{N12}$ represents hydrogen or $C_{1-2}$-alkyl (especially methyl);

or $R^{N11}$ and $R^{N12}$ together with the nitrogen atom to which they are attached form a 4- to 6-membered heterocyclyl selected from azetidin-1-yl which is unsubstituted, or di-substituted in position 3 with fluoro; pyrrolidin-1-yl which is unsubstituted, or di-substituted in position 3 with fluoro; and piperidin-1-yl which is unsubstituted, or di-substituted in position 3 or 4 with fluoro;

or $R^{N11}$ and $R^{N12}$ together with the nitrogen atom to which they are attached form morpholin-4-yl;

or $R^{N11}$ and $R^{N12}$ together with the nitrogen atom to which they are attached form an indolin-1-yl ring.

10) Another embodiment relates to compounds according to embodiments 1) to 7), wherein $R^1$ represents an amide group of the structure

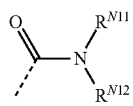

wherein
$R^{N11}$ represents
—$C_{1-6}$-alkyl (especially methyl, ethyl, isobutyl, 2,2-dimethylprop-1-yl, or 3,3-dimethylbut-1-yl);
—$CH_2$—$CH_2$—O—$C_{1-3}$-alkyl;
—$CH_2$—$C_{1-3}$-fluoroalkyl (especially —$CH_2$—$CF_3$ or —$CH_2$—$C(CH_3)_2F$);
cyclopropyl, cyclobutyl, —$CH_2$-cyclopropyl, —$CH_2$-cyclopentyl, —$CH_2$-1-fluorocyclopentyl, or —$CH_2$—$CH_2$-cyclopropyl;
3,3-difluorocyclobutyl, or —$CH_2$-3,3-difluorocyclobutyl;
$CH_2$-tetrahydro-2H-pyran-4-yl, or —$CH_2$—$CH_2$-tetrahydro-2H-pyran-4-yl;
tetrahydro-2H-pyran-4-yl, or oxetane-3-yl;
—$CH_2$—$CH_2$-morpholin-4-yl;
—$CH_2$-thiophenyl, —$CH_2$-pyridinyl, benzyl, or —$CH_2$-1-methyl-1H-imidazol-4-yl; or
phenyl, or pyridinyl;
and $R^{N12}$ represents hydrogen or $C_{1-2}$-alkyl (especially methyl).

11) Another embodiment relates to compounds according to embodiments 1) to 7), wherein $R^1$ represents an amide group of the structure

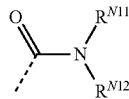

wherein
$R^{N11}$ represents
—$C_{1-6}$-alkyl (especially methyl, ethyl, isobutyl, 2,2-dimethylprop-1-yl, or 3,3-dimethylbut-1-yl);
—$CH_2$—$CH_2$—O—$C_{1-3}$-alkyl;
—$CH_2$—$C_{1-3}$-fluoroalkyl (especially —$CH_2$—$CF_3$ or —$CH_2$—$C(CH_3)_2F$); or
cyclopropyl, cyclobutyl, —$CH_2$-cyclopropyl, —$CH_2$-cyclopentyl, —$CH_2$-1-fluorocyclopentyl, or —$CH_2$—$CH_2$-cyclopropyl;
and $R^{N12}$ represents $C_{1-2}$-alkyl (especially methyl).

12) Another embodiment relates to compounds according to embodiments 1) to 7), wherein $R^1$ represents

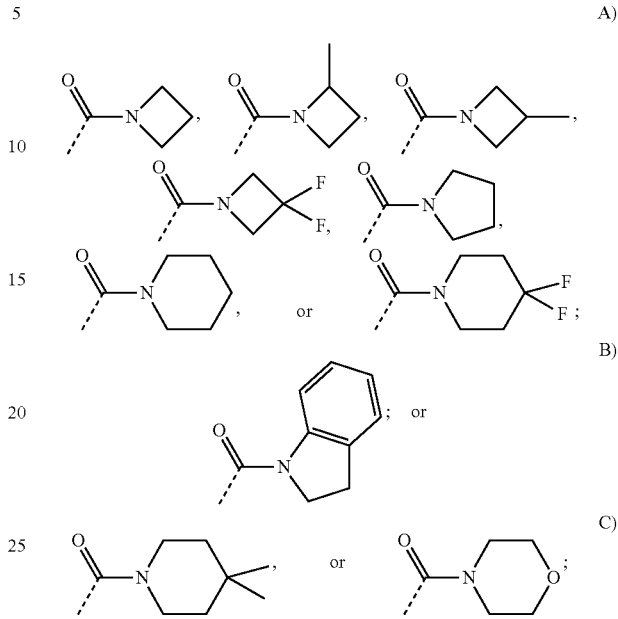

wherein each of the above groups A) to C) form a particular sub-embodiment; and wherein another sub-embodiment refers to groups A) and/or B).

13) Another embodiment relates to compounds according to any one of embodiments 1) to 12), wherein
$R^{2a}$ represents hydrogen; and $R^{2b}$ represents
—$C_{2-4}$-alkyl (especially ethyl),
benzyl;
phenyl which is unsubstituted, mono- or di-substituted with methyl; or
5-membered heteroaryl (especially 1H-pyrazole-3-yl) which is unsubstituted or mono-substituted with methyl;
or $R^{2a}$ and $R^{2b}$ both represent methyl, ethyl, or n-propyl;
or $R^{2a}$ and $R^{2b}$ together with the carbon atom to which they are attached form a 3- to 6-membered ring selected from
$C_{4-6}$-cycloalkylene, wherein said cycloalkyl independently is unsubstituted, mono-, or di-substituted, wherein the substituents independently are methyl or fluoro (especially cyclobutane-1,1-diyl, cyclopentane-1,1-diyl, cyclohexane-1,1-diyl, 3,3-difluorocyclobutane-1,1-diyl, 4,4-difluorocyclohexane-1,1-diyl; or, in addition, 4,4-dimethylcyclohexane-1,1-diyl);
tetrahydro-2H-pyran-4,4-diyl;
piperidine-4,4-diyl, wherein the nitrogen of said piperidine is unsubstituted, or substituted with —$C_{1-3}$-alkyl, —CO—$C_{1-3}$-alkyl, —CO—O—$C_{1-3}$-alkyl, —CO—NH-cyclopropyl, —$SO_2$—$C_{1-3}$-alkyl, —$SO_2$-cyclopropyl, or —$SO_2$—NH—$C_{1-3}$-alkyl (especially said piperidine is unsubstituted or substituted with methyl, —CO-methyl, —CO-methoxy, —CO—NH-cyclopropyl, —$SO_2$-methyl, —$SO_2$-cyclopropyl, or —$SO_2$—NH-methyl);
azetidine-3,3-diyl, wherein the nitrogen of said azetidine is substituted with —CO—O—$C_{1-3}$-alkyl (especially with —CO—O-methyl); or R²ᵃ and R²ᵇ together with the carbon atom to which they are attached form a spiro-bicyclic ring system of the structure:

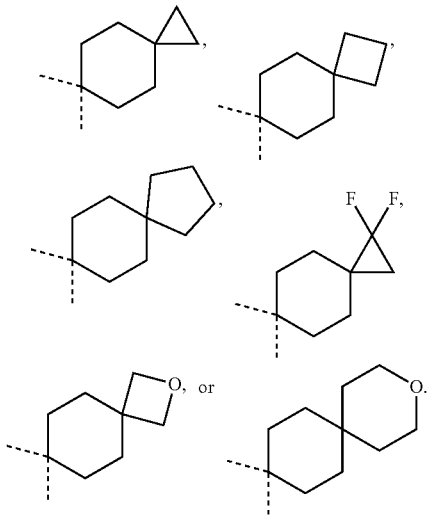

14) Another embodiment relates to compounds according to any one of embodiments 1) to 12), wherein R²ᵃ represents hydrogen; and R²ᵇ represents
- —C₂₋₄-alkyl (especially ethyl);
- benzyl;
- phenyl which is unsubstituted, mono- or di-substituted with methyl; or
- a 5-membered heteroaryl (especially 1H-pyrazole-3-yl) which is unsubstituted or mono-substituted with methyl.

15) Another embodiment relates to compounds according to any one of embodiments 1) to 12), wherein R²ᵃ and R²ᵇ both represent a methyl, ethyl, or n-propyl (especially methyl).

16) Another embodiment relates to compounds according to any one of embodiments 1) to 12), wherein R²ᵃ and R²ᵇ together with the carbon atom to which they are attached form a 4- to 6-membered ring selected from
- C₄₋₆-cycloalkylene, wherein said cycloalkyl independently is unsubstituted, mono-, or di-substituted, wherein the substituents independently are methyl or fluoro (especially cyclobutane-1,1-diyl, cyclopentane-1,1-diyl, cyclohexane-1,1-diyl, 3,3-difluorocyclobutane-1,1-diyl, 4,4-difluorocyclohexane-1,1-diyl; or, in addition, 4,4-dimethylcyclohexane-1,1-diyl);
- tetrahydro-2H-pyran-4,4-diyl, 2,2-dimethyltetrahydro-2H-pyran-4,4-diyl, or 2,2,6,6-tetramethyltetrahydro-2H-pyran-4,4-diyl (especially tetrahydro-2H-pyran-4,4-diyl); or
- piperidine-4,4-diyl, wherein the nitrogen of said piperidine is unsubstituted, or substituted with —C₁₋₃-alkyl, —CO—C₁₋₃-alkyl, —CO—O—C₁₋₃-alkyl, —CO—NH-cyclopropyl, —SO₂—C₁₋₃-alkyl, —SO₂-cyclopropyl, or —SO₂—NH—C₁₋₃-alkyl (especially said piperidine is unsubstituted or substituted with methyl, —CO-methyl, —CO-methoxy, —CO—NH-cyclopropyl, —SO₂-methyl, —SO₂-cyclopropyl, or —SO₂—NH-methyl).

17) Another embodiment relates to compounds according to any one of embodiments 1) to 16), wherein R³ represents methoxy.

18) Another embodiment relates to compounds according to any one of embodiments 1) to 16), wherein R³ represents hydroxy.

19) The invention, thus, relates to compounds of the Formula (I) as defined in embodiment 1), or to such compounds further limited by the characteristics of any one of embodiments 2) to 18), under consideration of their respective dependencies; to pharmaceutically acceptable salts thereof; and to the use of such compounds as further described herein below. For avoidance of any doubt, especially the following embodiments relating to the compounds of Formula (I) are thus possible and intended and herewith specifically disclosed in individualized form:

1, 2+1, 3+1, 3+2+1, 4+1, 4+2+1, 5+1, 5+2+1, 6+1, 6+2+1, 7+1, 7+2+1, 8+1, 8+2+1, 8+3+1, 8+3+2+1, 8+4+1, 8+4+2+1, 8+5+1, 8+5+2+1, 8+6+1, 8+6+2+1, 8+7+1, 8+7+2+1, 9+1, 9+2+1, 9+3+1, 9+3+2+1, 9+4+1, 9+4+2+1, 9+5+1, 9+5+2+1, 9+6+1, 9+6+2+1, 9+7+1, 9+7+2+1, 10+1, 10+2+1, 10+3+1, 10+3+2+1, 10+4+1, 10+4+2+1, 10+5+1, 10+5+2+1, 10+6+1, 10+6+2+1, 10+7+1, 10+7+2+1, 11+1, 11+2+1, 11+3+1, 11+3+2+1, 11+4+1, 11+4+2+1, 11+5+1, 11+5+2+1, 11+6+1, 11+6+2+1, 11+7+1, 11+7+2+1, 12+1, 12+2+1, 12+3+1, 12+3+2+1, 12+4+1, 12+4+2+1, 12+5+1, 12+5+2+1, 12+6+1, 12+6+2+1, 12+7+1, 12+7+2+1, 13+1, 13+2+1, 13+3+1, 13+3+2+1, 13+4+1, 13+4+2+1, 13+5+1, 13+5+2+1, 13+6+1, 13+6+2+1, 13+7+1, 13+7+2+1, 13+8+1, 13+8+2+1, 13+8+3+1, 13+8+3+2+1, 13+8+4+1, 13+8+4+2+1, 13+8+5+1, 13+8+5+2+1, 13+8+6+1, 13+8+6+2+1, 13+8+7+1, 13+8+7+2+1, 13+9+1, 13+9+2+1, 13+9+3+1, 13+9+3+2+1, 13+9+4+1, 13+9+4+2+1, 13+9+5+1, 13+9+5+2+1, 13+9+6+1, 13+9+6+2+1, 13+9+7+1, 13+9+7+2+1, 13+10+1, 13+10+2+1, 13+10+3+1, 13+10+3+2+1, 13+10+4+1, 13+10+4+2+1, 13+10+5+1, 13+10+5+2+1, 13+10+6+1, 13+10+6+2+1, 13+10+7+1, 13+10+7+2+1, 13+11+1, 13+11+2+1, 13+11+3+1, 13+11+3+2+1, 13+11+4+1, 13+11+4+2+1, 13+11+5+1, 13+11+5+2+1, 13+11+6+1, 13+11+6+2+1, 13+11+7+1, 13+11+7+2+1, 13+12+1, 13+12+2+1, 13+12+3+1, 13+12+3+2+1, 13+12+4+1, 13+12+4+2+1, 13+12+5+1, 13+12+5+2+1, 13+12+6+1, 13+12+6+2+1, 13+12+7+1, 13+12+7+2+1, 14+1, 14+2+1, 14+3+1, 14+3+2+1, 14+4+1, 14+4+2+1, 14+5+1, 14+5+2+1, 14+6+1, 14+6+2+1, 14+7+1, 14+7+2+1, 14+8+1, 14+8+3+1, 14+8+3+2+1, 14+8+4+1, 14+8+4+2+1, 14+8+5+1, 14+8+5+2+1, 14+8+6+1, 14+8+6+2+1, 14+8+7+1, 14+8+7+2+1, 14+9+1, 14+9+2+1, 14+9+3+1, 14+9+3+2+1, 14+9+4+1, 14+9+4+2+1, 14+9+5+1, 14+9+5+2+1, 14+9+6+1, 14+9+6+2+1, 14+9+7+1, 14+9+7+2+1, 14+10+1, 14+10+2+1, 14+10+3+1, 14+10+3+2+1, 14+10+4+1, 14+10+4+2+1, 14+10+5+1, 14+10+5+2+1, 14+10+6+1, 14+10+6+2+1, 14+10+7+1, 14+10+7+2+1, 14+11+1, 14+11+2+1, 14+11+3+1, 14+11+3+2+1, 14+11+4+1, 14+11+4+2+1, 14+11+5+1, 14+11+5+2+1, 14+11+6+1, 14+11+6+2+1, 14+11+7+1, 14+11+7+2+1, 14+12+1, 14+12+2+1, 14+12+3+1, 14+12+3+2+1, 14+12+4+1, 14+12+4+2+1, 14+12+5+1, 14+12+5+2+1, 14+12+6+1, 14+12+6+2+1, 14+12+7+1, 14+12+7+2+1, 15+1, 15+2+1, 15+3+1, 15+3+2+1, 15+4+1, 15+4+2+1, 15+5+1, 15+5+2+1, 15+6+1, 15+6+2+1, 15+7+1, 15+7+2+1, 15+8+1, 15+8+2+1, 15+8+3+1, 15+8+3+2+1, 15+8+4+1, 15+8+4+2+1, 15+8+5+1, 15+8+5+2+1, 15+8+6+1, 15+8+6+2+1, 15+8+7+1, 15+8+7+2+1, 15+9+1, 15+9+2+1, 15+9+3+1, 15+9+3+2+1, 15+9+4+1, 15+9+4+2+1, 15+9+5+1, 15+9+5+2+1, 15+9+6+1, 15+9+6+2+1, 15+9+7+1,

15+9+7+2+1, 15+10+1, 15+10+2+1, 15+10+3+1, 15+10+3+2+1, 15+10+4+1, 15+10+4+2+1, 15+10+5+1, 15+10+5+2+1, 15+10+6+1, 15+10+6+2+1, 15+10+7+1, 15+10+7+2+1, 15+11+1, 15+11+2+1, 15+11+3+1, 15+11+3+2+1, 15+11+4+1, 15+11+4+2+1, 15+11+5+1, 15+11+5+2+1, 15+11+6+1, 15+11+6+2+1, 15+11+7+1, 15+11+7+2+1, 15+12+1, 15+12+2+1, 15+12+3+1, 15+12+3+2+1, 15+12+4+1, 15+12+4+2+1, 15+12+5+1, 15+12+5+2+1, 15+12+6+1, 15+12+6+2+1, 15+12+7+1, 15+12+7+2+1, 16+1, 16+2+1, 16+3+1, 16+3+2+1, 16+4+1, 16+4+2+1, 16+5+1, 16+5+2+1, 16+6+1, 16+6+2+1, 16+7+1, 16+7+2+1, 16+8+1, 16+8+2+1, 16+8+3+1, 16+8+3+2+1, 16+8+4+1, 16+8+4+2+1, 16+8+5+1, 16+8+5+2+1, 16+8+6+1, 16+8+6+2+1, 16+8+7+1, 16+8+7+2+1, 16+9+1, 16+9+2+1, 16+9+3+1, 16+9+3+2+1, 16+9+4+1, 16+9+4+2+1, 16+9+5+1, 16+9+5+2+1, 16+9+6+1, 16+9+6+2+1, 16+9+7+1, 16+9+7+2+1, 16+10+1, 16+10+2+1, 16+10+3+1, 16+10+3+2+1, 16+10+4+1, 16+10+4+2+1, 16+10+5+1, 16+10+5+2+1, 16+10+6+1, 16+10+6+2+1, 16+10+7+1, 16+10+7+2+1, 16+11+1, 16+11+2+1, 16+11+3+1, 16+11+3+2+1, 16+11+4+1, 16+11+4+2+1, 16+11+5+1, 16+11+5+2+1, 16+11+6+1, 16+11+6+2+1, 16+11+7+1, 16+11+7+2+1, 16+12+1, 16+12+2+1, 16+12+3+1, 16+12+3+2+1, 16+12+4+1, 16+12+4+2+1, 16+12+5+1, 16+12+5+2+1, 16+12+6+1, 16+12+6+2+1, 16+12+7+1, 16+12+7+2+1, 17+1, 17+2+1, 17+3+1, 17+3+2+1, 17+4+1, 17+4+2+1, 17+5+1, 17+5+2+1, 17+6+1, 17+6+2+1, 17+7+1, 17+7+2+1, 17+8+1, 17+8+2+1, 17+8+3+1, 17+8+3+2+1, 17+8+4+1, 17+8+4+2+1, 17+8+5+1, 17+8+5+2+1, 17+8+6+1, 17+8+6+2+1, 17+8+7+1, 17+8+7+2+1, 17+9+1, 17+9+2+1, 17+9+3+1, 17+9+3+2+1, 17+9+4+1, 17+9+4+2+1, 17+9+5+1, 17+9+5+2+1, 17+9+6+1, 17+9+6+2+1, 17+9+7+1, 17+9+7+2+1, 17+10+1, 17+10+2+1, 17+10+3+1, 17+10+3+2+1, 17+10+4+1, 17+10+4+2+1, 17+10+5+1, 17+10+5+2+1, 17+10+6+1, 17+10+6+2+1, 17+10+7+1, 17+10+7+2+1, 17+11+1, 17+11+2+1, 17+11+3+1, 17+11+3+2+1, 17+11+4+1, 17+11+4+2+1, 17+11+5+1, 17+11+5+2+1, 17+11+6+1, 17+11+6+2+1, 17+11+7+1, 17+11+7+2+1, 17+12+1, 17+12+2+1, 17+12+3+1, 17+12+3+2+1, 17+12+4+1, 17+12+4+2+1, 17+12+5+1, 17+12+5+2+1, 17+12+6+1, 17+12+6+2+1, 17+12+7+1, 17+12+7+2+1, 17+13+1, 17+13+2+1, 17+13+3+1, 17+13+3+2+1, 17+13+4+1, 17+13+4+2+1, 17+13+5+1, 17+13+5+2+1, 17+13+6+1, 17+13+6+2+1, 17+13+7+1, 17+13+7+2+1, 17+13+8+1, 17+13+8+2+1, 17+13+8+3+1, 17+13+8+3+2+1, 17+13+8+4+1, 17+13+8+4+2+1, 17+13+8+5+1, 17+13+8+5+2+1, 17+13+8+6+1, 17+13+8+6+2+1, 17+13+8+7+1, 17+13+8+7+2+1, 17+13+9+1, 17+13+9+2+1, 17+13+9+3+1, 17+13+9+3+2+1, 17+13+9+4+1, 17+13+9+4+2+1, 17+13+9+5+1, 17+13+9+5+2+1, 17+13+9+6+1, 17+13+9+6+2+1, 17+13+9+7+1, 17+13+9+7+2+1, 17+13+10+1, 17+13+10+2+1, 17+13+10+3+1, 17+13+10+3+2+1, 17+13+10+4+1, 17+13+10+4+2+1, 17+13+10+5+1, 17+13+10+5+2+1, 17+13+10+6+1, 17+13+10+6+2+1, 17+13+10+7+1, 17+13+10+7+2+1, 17+13+11+1, 17+13+11+2+1, 17+13+11+3+1, 17+13+11+3+2+1, 17+13+11+4+1, 17+13+11+4+2+1, 17+13+11+5+1, 17+13+11+5+2+1, 17+13+11+6+1, 17+13+11+6+2+1, 17+13+11+7+1, 17+13+11+7+2+1, 17+13+12+1, 17+13+12+2+1, 17+13+12+3+1, 17+13+12+3+2+1, 17+13+12+4+1, 17+13+12+4+2+1, 17+13+12+5+1, 17+13+12+5+2+1, 17+13+12+6+1, 17+13+12+6+2+1, 17+13+12+7+1, 17+13+12+7+2+1, 17+14+1, 17+14+2+1, 17+14+3+1, 17+14+3+2+1, 17+14+4+1, 17+14+4+2+1, 17+14+5+1, 17+14+5+2+1, 17+14+6+1, 17+14+6+2+1, 17+14+7+1, 17+14+7+2+1, 17+14+8+1, 17+14+8+2+1, 17+14+8+3+1, 17+14+8+3+2+1, 17+14+8+4+1, 17+14+8+4+2+1, 17+14+8+5+1, 17+14+8+5+2+1, 17+14+8+6+1, 17+14+8+6+2+1, 17+14+8+7+1, 17+14+8+7+2+1, 17+14+9+1, 17+14+9+2+1, 17+14+9+3+1, 17+14+9+3+2+1, 17+14+9+4+1, 17+14+9+4+2+1, 17+14+9+5+1, 17+14+9+5+2+1, 17+14+9+6+1, 17+14+9+6+2+1, 17+14+9+7+1, 17+14+9+7+2+1, 17+14+10+1, 17+14+10+2+1, 17+14+10+3+1, 17+14+10+3+2+1, 17+14+10+4+1, 17+14+10+4+2+1, 17+14+10+5+1, 17+14+10+5+2+1, 17+14+10+6+1, 17+14+10+6+2+1, 17+14+10+7+1, 17+14+10+7+2+1, 17+14+11+1, 17+14+11+2+1, 17+14+11+3+1, 17+14+11+3+2+1, 17+14+11+4+1, 17+14+11+4+2+1, 17+14+11+5+1, 17+14+11+5+2+1, 17+14+11+6+1, 17+14+11+6+2+1, 17+14+11+7+1, 17+14+11+7+2+1, 17+14+12+1, 17+14+12+2+1, 17+14+12+3+1, 17+14+12+3+2+1, 17+14+12+4+1, 17+14+12+4+2+1, 17+14+12+5+1, 17+14+12+5+2+1, 17+14+12+6+1, 17+14+12+6+2+1, 17+14+12+7+1, 17+14+12+7+2+1, 17+15+1, 17+15+2+1, 17+15+3+1, 17+15+3+2+1, 17+15+4+1, 17+15+4+2+1, 17+15+5+1, 17+15+5+2+1, 17+15+6+1, 17+15+6+2+1, 17+15+7+1, 17+15+7+2+1, 17+15+8+1, 17+15+8+2+1, 17+15+8+3+1, 17+15+8+3+2+1, 17+15+8+4+1, 17+15+8+4+2+1, 17+15+8+5+1, 17+15+8+5+2+1, 17+15+8+6+1, 17+15+8+6+2+1, 17+15+8+7+1, 17+15+8+7+2+1, 17+15+9+1, 17+15+9+2+1, 17+15+9+3+1, 17+15+9+3+2+1, 17+15+9+4+1, 17+15+9+4+2+1, 17+15+9+5+1, 17+15+9+5+2+1, 17+15+9+6+1, 17+15+9+6+2+1, 17+15+9+7+1, 17+15+9+7+2+1, 17+15+10+1, 17+15+10+2+1, 17+15+10+3+1, 17+15+10+3+2+1, 17+15+10+4+1, 17+15+10+4+2+1, 17+15+10+5+1, 17+15+10+5+2+1, 17+15+10+6+1, 17+15+10+6+2+1, 17+15+10+7+1, 17+15+10+7+2+1, 17+15+11+1, 17+15+11+2+1, 17+15+11+3+1, 17+15+11+3+2+1, 17+15+11+4+1, 17+15+11+4+2+1, 17+15+11+5+1, 17+15+11+5+2+1, 17+15+11+6+1, 17+15+11+6+2+1, 17+15+11+7+1, 17+15+11+7+2+1, 17+15+12+1, 17+15+12+2+1, 17+15+12+3+1, 17+15+12+3+2+1, 17+15+12+4+1, 17+15+12+4+2+1, 17+15+12+5+1, 17+15+12+5+2+1, 17+15+12+6+1, 17+15+12+6+2+1, 17+15+12+7+1, 17+15+12+7+2+1, 17+16+1, 17+16+2+1, 17+16+3+1, 17+16+3+2+1, 17+16+4+1, 17+16+4+2+1, 17+16+5+1, 17+16+5+2+1, 17+16+6+1, 17+16+6+2+1, 17+16+7+1, 17+16+7+2+1, 17+16+8+1, 17+16+8+2+1, 17+16+8+3+1, 17+16+8+3+2+1, 17+16+8+4+1, 17+16+8+4+2+1, 17+16+8+5+1, 17+16+8+5+2+1, 17+16+8+6+1, 17+16+8+6+2+1, 17+16+8+7+1, 17+16+8+7+2+1, 17+16+9+1, 17+16+9+2+1, 17+16+9+3+1, 17+16+9+3+2+1, 17+16+9+4+1, 17+16+9+4+2+1, 17+16+9+5+1, 17+16+9+5+2+1, 17+16+9+6+1, 17+16+9+6+2+1, 17+16+9+7+1, 17+16+9+7+2+1, 17+16+10+1, 17+16+10+2+1, 17+16+10+3+1, 17+16+10+3+2+1, 17+16+10+4+1, 17+16+10+4+2+1, 17+16+10+5+1, 17+16+10+5+2+1, 17+16+10+6+1, 17+16+10+6+2+1, 17+16+10+7+1, 17+16+10+7+2+1, 17+16+11+1, 17+16+11+2+1, 17+16+11+3+1, 17+16+11+3+2+1, 17+16+11+4+1, 17+16+11+4+2+1, 17+16+11+5+1, 17+16+11+5+2+1, 17+16+11+6+1, 17+16+11+6+2+1, 17+16+11+7+1, 17+16+11+7+2+1, 17+16+12+1, 17+16+12+2+1, 17+16+12+3+1, 17+16+12+3+2+1, 17+16+12+4+1,

17+16+12+4+2+1, 17+16+12+5+1, 17+16+12+5+2+1, 17+16+12+6+1, 17+16+12+6+2+1, 17+16+12+7+1, 17+16+12+7+2+1.

In the list above the numbers refer to the embodiments according to their numbering provided hereinabove whereas "+" indicates the dependency from another embodiment. The different individualized embodiments are separated by commas. In other words, "13+9+5+1" for example refers to embodiment 13) depending on embodiment 9), depending on embodiment 5), depending on embodiment 1), i.e. embodiment "13+9+5+1" corresponds to the compounds of formula (I) according to embodiment 1) further limited by all the features of the embodiments 5), 9), and 13).

20) Another embodiment relates to compounds of Formula (I) according to embodiment 1), which are selected from the following compounds:

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-isobutyl-N-methylacetamide;

2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N,N,3-trimethylbutanamide;

2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N,N-diethyl-3-hydroxy-3-methylbutanamide;

2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-methyl-1-(2-methylazetidin-1-yl)butan-1-one;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-methyl-1-(3-methylazetidin-1-yl)butan-1-one;

1-(azetidin-1-yl)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-methylbutan-1-one;

2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxy-1-methylpiperidin-4-yl)-N-isobutyl-N-methylacetamide;

2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxy-1-methylpiperidin-4-yl)-N-methylacetamide;

N-benzyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxy-1-methylpiperidin-4-yl)-N-methylacetamide;

2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxy-1-methylpiperidin-4-yl)-1-(piperidin-1-yl)ethan-1-one;

2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxy-1-methylpiperidin-4-yl)-1-(indolin-1-yl)ethan-1-one;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N,N-dimethylacetamide;

2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N,N-diethyl-2-(4-hydroxytetrahydro-2H-pyran-4-yl)acetamide;

2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-1-(2-methylazetidin-1-yl)ethan-1-one;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-1-(3-methylazetidin-1-yl)ethan-1-one;

1-(azetidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)ethan-1-one;

(S)—N-benzyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-1-(piperidin-1-yl)ethan-1-one;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-1-(indolin-1-yl)ethan-1-one;

2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-1-(pyrrolidi n-1-yl)ethan-1-one;

(S)—N-(cyclopentylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methylacetamide;

2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-((tetrahydro-2H-pyran-4-yl)methyl)acetamide;

2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxytetrahydro-2H-pyran-4-yl)-N-((tetrahydro-2H-pyran-4-yl)methyl)acetamide;

2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-((1-methyl-1H-imidazol-4-yl)methyl)acetamide;

2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(2-(tetrahydro-2H-pyran-4-yl)ethyl)acetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(2-(tetrahydro-2H-pyran-4-yl)ethyl)acetamide;

N-(2-cyclopropylethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methylacetamide;

(S)—N-(cyclopropylmethyl)-2-(((2S,3R,4S,5R,6R)-3,5-dihydroxy-6-(hydroxymethyl)-4-(4-(3,4,5-trifluorophenyl)-

1H-1,2,3-triazol-1-yl)tetrahydro-2H-pyran-2-yl)thio)-2-(4-hydroxytetrahydro-2H-pyran-4-yl)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxytetrahydro-2H-pyran-4-yl)-N-methylacetamide;

2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(2,2,2-trifluoroethyl)acetamide;

2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(1-hydroxycyclohexyl)-N-methyl acetamide;

2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclohexyl)-1-(piperidin-1-yl)ethan-1-one;

(R)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclohexyl)-N-methyl-N-(2,2,2-trifluoroethyl)acetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclohexyl)-N-methyl-N-(2,2,2-trifluoroethyl)acetamide;

N-cyclobutyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclohexyl)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-(2-fluoro-2-methylpropyl)-2-(1-hydroxycyclohexyl)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclohexyl)-N-methyl-N-(pyridin-2-ylmethyl)acetamide;

(S)-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N,N-dimethylacetamide;

2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-N-methylacetamide;

(S)—N-cyclobutyl-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-methylacetamide;

(S)-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-1-(piperidin-1-yl)ethan-1-one;

(S)—N-(cyclopropylmethyl)-2-(4,4-difluoro-1-hydroxycyclohexyl)-2-(((2S,3R,4S,5R,6R)-3,5-di hydroxy-6-(hydroxymethyl)-4-(4-(3,4,5-trifluorophenyl)-1H-1,2,3-triazol-1-yl)tetrahydro-2H-pyran-2-yl)thio)-N-methylacetamide;

N-cyclopropyl-2-(4,4-difluoro-1-hydroxycyclohexyl)-2-(((2S,3R,4S,5R,6R)-3,5-di hydroxy-6-(hydroxymethyl)-4-(4-(3,4,5-trifluorophenyl)-1H-1,2,3-triazol-1-yl)tetrahydro-2H-pyran-2-yl)thio)-N-methylacetamide;

2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-(2-fluoro-2-methylpropyl)-N-methyl acetamide;

(S)-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-((1-fluorocyclopentyl)methyl)-N-methylacetamide;

2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-(3,3-dimethyl butyl)-N-methyl acetamide;

2-(4,4-difluoro-1-hydroxycyclohexyl)-1-(4,4-difluoropiperidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)ethan-1-one;

(S)-2-(4,4-difluoro-1-hydroxycyclohexyl)-1-(3,3-difluoroazetidin-1-yl)-2-(((2S,3R,4S,5R,6R)-3,5-di hydroxy-6-(hydroxymethyl)-4-(4-(3,4,5-trifluorophenyl)-1H-1,2,3-triazol-1-yl)tetrahydro-2H-pyran-2-yl)thio)ethan-1-one;

1-(azetidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclopentyl)ethan-1-one;

2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclopentyl)-N-methyl-N-(2,2,2-trifluoroethyl)acetamide;

N-cyclobutyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclopentyl)-N-methylacetamide;

2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclopentyl)-N-methyl-N-neopentyl acetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(1-hydroxycyclobutyl)-N-methyl acetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)-1-(piperidin-1-yl)ethan-1-one;

(S)—N-(cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)-N-methyl-N-(2,2,2-trifluoroethyl)acetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-(2-fluoro-2-methylpropyl)-2-(1-hydroxycyclobutyl)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)-N-methyl-N-neopentyl acetamide;

(S)-2-(3,3-difluoro-1-hydroxycyclobutyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-N-methylacetamide;

(S)—N-(cyclopropylmethyl)-2-(3,3-difluoro-1-hydroxycyclobutyl)-2-(((2S,3R,4S,5R,6R)-3,5-di hydroxy-6-(hydroxymethyl)-4-(4-(3,4,5-trifluorophenyl)-1H-1,2,3-triazol-1-yl)tetrahydro-2H-pyran-2-yl)thio)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N,3-diethyl-3-hydroxy-N-methylpentanamide;

N-Benzyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N,3-dimethylbutanamide;

2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-methyl-1-(piperidin-1-yl)butan-1-one;

(S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-methyl-1-(pyrrolidin-1-yl)butan-1-one;

2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N,3-dimethyl-N-((1-methyl-1H-imidazol-4-yl)methyl)butanamide;

N-(Cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N,3-dimethyl butanamide;

2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N-(2-methoxyethyl)-N,3-di methyl butanamide;

2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N,3-dimethyl-N-(2-morpholinoethyl)butanamide;

2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-3-hydroxy-N-methylpentanamide;

N-(Cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N-methylpentanamide;

2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-3-hydroxy-N-methyl-4-phenylbutanamide;

N-(Cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N-methyl-4-phenylbutanamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxy-1-(methylsulfonyl)piperidin-4-yl)-N-methyl acetamide;

(S)-2-(1-(cyclopropylsulfonyl)-4-hydroxypiperidin-4-yl)-2-(((2S,3R,4S,5R,6R)-3,5-di hydroxy-6-(hydroxymethyl)-4-(4-(3,4,5-trifluorophenyl)-1H-1,2,3-triazol-1-yl)tetrahydro-2H-pyran-2-yl)thio)-N-ethyl-N-methylacetamide;

N-Cyclopropyl-4-(1-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(ethyl(methyl)amino)-2-oxoethyl)-4-hydroxypiperidine-1-carboxamide; and Methyl 4-((S)-1-(((2S,3R,4S,5R,6R)-3,5-di hydroxy-6-(hydroxymethyl)-4-(4-(3,4,5-trifluorophenyl)-1H-1,2,3-triazol-1-yl)tetrahydro-2H-pyran-2-yl)thio)-2-(ethyl(methyl)amino)-2-oxoethyl)-4-hydroxypiperidine-1-carboxylate.

21) Another embodiment relates to compounds of Formula (I) according to embodiment 1), which are selected from the following compounds:

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-isobutyl-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N,N,3-tri methyl butanamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-3-hydroxy-N,3-dimethylbutanamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N,N-diethyl-3-hydroxy-3-methylbutanamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-methyl-1-((R)-2-methylazetidin-1-yl)butan-1-one;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-methyl-1-((S)-2-methylazetidin-1-yl)butan-1-one;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-methyl-1-(3-methylazetidin-1-yl)butan-1-one;

(S)-1-(azetidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-methyl butan-1-one;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxy-1-methylpiperidin-4-yl)-N-isobutyl-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxy-1-methyl piperidin-4-yl)-N-methylacetamide;

(S)—N-benzyl-2-(((2S,3R,4S,5R,6R)-3,5-di hydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxy-1-methylpiperidin-4-yl)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxy-1-methylpiperidin-4-yl)-1-(piperidin-1-yl)ethan-1-one;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxy-1-methylpiperidin-4-yl)-1-(indolin-1-yl)ethan-1-one;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N,N-dimethylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N,N-diethyl-2-(4-hydroxytetrahydro-2H-pyran-4-yl)acetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-1-((R)-2-methylazetidin-1-yl)ethan-1-one;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-1-((S)-2-methyl azetidin-1-yl)ethan-1-one;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-1-(3-methyl azetidin-1-yl)ethan-1-one;

(S)-1-(azetidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)ethan-1-one;

(S)—N-benzyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-1-(piperidin-1-yl)ethan-1-one;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-1-(indolin-1-yl)ethan-1-one;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(thiophen-2-ylmethyl)acetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-1-(pyrrolidin-1-yl)ethan-1-one;

(S)—N-(cyclopentylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-((tetrahydro-2H-pyran-4-yl)methyl)acetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxytetrahydro-2H-pyran-4-yl)-N-((tetrahydro-2H-pyran-4-yl)methyl)acetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-((1-methyl-1H-imidazol-4-yl)methyl)acetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(2-(tetrahydro-2H-pyran-4-yl)ethyl)acetamide;

(S)—N-(2-cyclopropylethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methylacetamide;

(S)—N-(cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxytetrahydro-2H-pyran-4-yl)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(2,2,2-trifluoroethyl)acetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(1-hydroxycyclohexyl)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclohexyl)-1-(piperidin-1-yl)ethan-1-one;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclohexyl)-N-methyl-N-(2,2,2-trifluoroethyl)acetamide;

(S)—N-cyclobutyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclohexyl)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-(2-fluoro-2-methylpropyl)-2-(1-hydroxycyclohexyl)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclohexyl)-N-methyl-N-(pyridin-2-ylmethyl)acetamide;

(S)-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N,N-dimethyl acetamide;

(S)-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-N-methylacetamide;

(S)—N-cyclobutyl-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-methylacetamide;

(S)-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-1-(piperidin-1-yl)ethan-1-one;

(S)—N-(cyclopropylmethyl)-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-methylacetamide;

(S)—N-cyclopropyl-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-methylacetamide;

(S)-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-(2-fluoro-2-methyl propyl)-N-methyl acetamide;

(S)-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-((1-fluorocyclopentyl)methyl)-N-methylacetamide;

(S)-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-(3,3-dimethyl butyl)-N-methyl acetamide;

(S)-2-(4,4-difluoro-1-hydroxycyclohexyl)-1-(4,4-difluoropiperidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)ethan-1-one;

(S)-2-(4,4-difluoro-1-hydroxycyclohexyl)-1-(3,3-difluoroazetidin-1-yl)-2-(((2S,3R,4S,5R,6R)-3,5-di hydroxy-6-(hydroxymethyl)-4-(4-(3,4,5-trifluorophenyl)-1H-1,2,3-triazol-1-yl)tetrahydro-2H-pyran-2-yl)thio)ethan-1-one;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(1-hydroxycyclopentyl)-N-methylacetamide;

(S)-1-(azetidin-1-yl)-2-(((2S,3R,4S,5R,6R)-3,5-di hydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclopentyl)ethan-1-one;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclopentyl)-N-methyl-N-(2,2,2-trifluoroethyl)acetamide;

(S)—N-cyclobutyl-2-(((2S,3R,4S,5R,6R)-3,5-di hydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclopentyl)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclopentyl)-N-methyl-N-neopentylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(1-hydroxycyclobutyl)-N-methylacetamide;

(S)-1-(azetidin-1-yl)-2-(((2S,3R,4S,5R,6R)-3,5-di hydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)ethan-1-one;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)-1-(piperidin-1-yl)ethan-1-one;

(S)—N-(cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)-N-methyl-N-(2,2,2-trifluoroethyl)acetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-(2-fluoro-2-methylpropyl)-2-(1-hydroxycyclobutyl)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)-N-methyl-N-neopentyl acetamide;

(S)-2-(3,3-difluoro-1-hydroxycyclobutyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-N-methylacetamide;

(S)-1-(azetidin-1-yl)-2-(3,3-difluoro-1-hydroxycyclobutyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)ethan-1-one;

(S)—N-(cyclopropylmethyl)-2-(3,3-difluoro-1-hydroxycyclobutyl)-2-(((2S,3R,4S,5R,6R)-3,5-di hydroxy-6-(hydroxymethyl)-4-(4-(3,4,5-trifluorophenyl)-1H-1,2,3-triazol-1-yl)tetrahydro-2H-pyran-2-yl)thio)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N, 3-diethyl-3-hydroxy-N-methylpentanamide;

(S)—N-(cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-ethyl-3-hydroxy-N-methylpentanamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-ethyl-N-(2-fluoro-2-methylpropyl)-3-hydroxy-N-methylpentanamide;

(S)—N-benzyl-2-(((2S,3R,4S,5R,6R)-3,5-di hydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N,3-dimethylbutanamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-methyl-1-(piperidin-1-yl)butan-1-one;

(S)-2-(((2S,3R,4S,5R,6R)-3,5-Di hydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-methyl-1-(pyrrolidin-1-yl)butan-1-one;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N,3-dimethyl-N-((1-methyl-1H-imidazol-4-yl)methyl)butanamide;

(S)—N-(cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N,3-dimethylbutanamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N,3-dimethyl-N-neopentylbutanamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N-(2-methoxyethyl)-N,3-dimethylbutanamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N,3-dimethyl-N-(2-morpholinoethyl)butanamide;

(2S,3R)-2-(((2S,3R,4S,5R,6R)-3,5-di hydroxy-6-(hydroxymethyl)-4-(4-(3,4,5-trifluorophenyl)-1H-1,2,3-triazol-1-yl)tetrahydro-2H-pyran-2-yl)thio)-N-ethyl-3-hydroxy-N-methylpentanamide;

(2S,3S)-2-(((2S,3R,4S,5R,6R)-3,5-di hydroxy-6-(hydroxymethyl)-4-(4-(3,4,5-trifluorophenyl)-1H-1,2,3-triazol-1-yl)tetrahydro-2H-pyran-2-yl)thio)-N-ethyl-3-hydroxy-N-methylpentanamide;
(2S,3R)-1-(azetidin-1-yl)-2-(((2S,3R,4S,5R,6R)-3,5-dihydroxy-6-(hydroxymethyl)-4-(4-(3,4,5-trifluorophenyl)-1H-1,2,3- triazol-1-yl)tetrahydro-2H-pyran-2-yl)thio)-3-hydroxypentan-1-one;
(2S,3S)-1-(azetidin-1-yl)-2-(((2S,3R,4S,5R,6R)-3,5-dihydroxy-6-(hydroxymethyl)-4-(4-(3,4,5-trifluorophenyl)-1H-1,2,3- triazol-1-yl)tetrahydro-2H-pyran-2-yl)thio)-3-hydroxypentan-1-one;
(2S,3R)—N-(cyclopropylmethyl)-2-(((2S,3R,4S,5R,6R)-3,5-di hydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N-methylpentanamide;
(2S,3S)—N-(cyclopropyl methyl)-2-(((2S,3R,4S,5R,6R)-3,5-di hydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N-methylpentanamide;
(2S,3R)-2-(((2S,3R,4S,5R,6R)-3,5-di hydroxy-6-(hydroxymethyl)-4-(4-(3,4,5-trifluorophenyl)-1H-1,2,3-triazol-1-yl)tetrahydro-2H-pyran-2-yl)thio)-N-ethyl-3-hydroxy-N-methyl-4-phenyl butanamide;
(2S,3S)-2-(((2S,3R,4S,5R,6R)-3,5-di hydroxy-6-(hydroxymethyl)-4-(4-(3,4,5-trifluorophenyl)-1H-1,2,3-triazol-1-yl)tetrahydro-2H-pyran-2-yl)thio)-N-ethyl-3-hydroxy-N-methyl-4-phenyl butanamide;
(2S,3R)-1-(azetidin-1-yl)-2-(((2S,3R,4S,5R,6R)-3,5-dihydroxy-6-(hydroxymethyl)-4-(4-(3,4,5-trifluorophenyl)-1H-1,2,3- triazol-1-yl)tetrahydro-2H-pyran-2-yl)thio)-3-hydroxy-4-phenylbutan-1-one;
(2S,3S)-1-(azetidin-1-yl)-2-(((2S,3R,4S,5R,6R)-3,5-dihydroxy-6-(hydroxymethyl)-4-(4-(3,4,5-trifluorophenyl)-1H-1,2,3- triazol-1-yl)tetrahydro-2H-pyran-2-yl)thio)-3-hydroxy-4-phenylbutan-1-one;
(2S,3R)—N-(cyclopropylmethyl)-2-(((2S,3R,4S,5R,6R)-3,5-di hydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N-methyl-4-phenylbutanamide;
(2S,3S)—N-(cyclopropyl methyl)-2-(((2S,3R,4S,5R,6R)-3,5-di hydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N-methyl-4-phenylbutanamide;
(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxy-1-(methylsulfonyl)piperidin-4-yl)-N-methylacetamide;
(S)-2-(1-(cyclopropylsulfonyl)-4-hydroxypiperidin-4-yl)-2-(((2S,3R,4S,5R,6R)-3,5-di hydroxy-6-(hydroxymethyl)-4-(4-(3,4,5-trifluorophenyl)-1H-1,2,3-triazol-1-yl)tetrahydro-2H-pyran-2-yl)thio)-N-ethyl-N-methylacetamide; and
Methyl 4-((S)-1-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(ethyl(methyl)amino)-2-oxoethyl)-4-hydroxypiperidine-1-carboxylate.

22) In addition to the compounds listed in embodiment 20), further compounds according to embodiment 1) are selected from the following compounds:
(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-3-hydroxy-N,3-dimethylbutanamide; and
(S)—N-Cyclopropyl-4-(1-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(ethyl(methyl)amino)-2-oxoethyl)-4-hydroxypiperidine-1-carboxamide.

23) In addition to the compounds listed in embodiment 21), further compounds according to embodiment 1) are selected from the following compounds:
(2S,3R)-2-(((2S,3R,4S,5R,6R)-3,5-di hydroxy-6-(hydroxymethyl)-4-(4-(3,4,5-trifluorophenyl)-1H-1,2,3-triazol-1-yl)tetrahydro-2H-pyran-2-yl)thio)-N-ethyl-3-hydroxy-N-methyl-3-(1-methyl-1H-pyrazol-3-yl)propanamide;
(2S,3S)-2-(((2S,3R,4S,5R,6R)-3,5-di hydroxy-6-(hydroxymethyl)-4-(4-(3,4,5-trifluorophenyl)-1H-1,2,3-triazol-1-yl)tetrahydro-2H-pyran-2-yl)thio)-N-ethyl-3-hydroxy-N-methyl-3-(1-methyl-1H-pyrazol-3-yl)propanamide;
(2S,3R)-1-1-(Azetidin-1-yl)-2-(((2S,3R,4S,5R,6R)-3,5-di hydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-(1-methyl-1H-pyrazol-3-yl)propan-1-one;
(2S,3S)-1-(Azetidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-(1-methyl-1H-pyrazol-3-yl)propan-1-one;
(2S,3R)—N-(cyclopropylmethyl)-2-(((2S,3R,4S,5R,6R)-3,5-di hydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N-methyl-3-(1-methyl-1H-pyrazol-3-yl)propanamide;
(2S,3S)—N-(cyclopropyl methyl)-2-(((2S,3R,4S,5R,6R)-3,5-di hydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N-methyl-3-(1-methyl-1H-pyrazol-3-yl)propanamide; and
(S)—N-Cyclopropyl-4-(1-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(ethyl(methyl)amino)-2-oxoethyl)-4-hydroxypiperidine-1-carboxamide.

24) In addition to the compounds listed in embodiment 20), further compounds according to embodiment 1) are selected from the following compounds:
N-(Cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxytetrahydro-2H-pyran-4-yl)acetamide;
(S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(oxetan-3-yl)acetamide;
(2R,3R,4S,5R,6S)-2-(Acetoxymethyl)-6-(((3)-2-(ethyl(methyl)amino)-1-(3-hydroxy-1-(methoxycarbonyl)azetidin-3-yl)-2-oxoethyl)thio)-4-(4-(3,4,5-trifluorophenyl)-1H-1,2,3-triazol-1-yl)tetrahydro-2H-pyran-3,5-diyl diacetate;
N-Cyclopropyl-4-((S)-2-(ethyl(methyl)amino)-1-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-oxoethyl)-4-hydroxypiperidine-1-carboxamide;
2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxytetrahydro-2H-pyran-4-yl)-N-phenylacetamide;
(S)-2-(((2S,3R,4S,5R,6R)-3,5-Dihydroxy-6-(hydroxymethyl)-4-(4-(3,4,5-trifluorophenyl)-1H-1,2,3-triazol-1-yl)

tetrahydro-2H-pyran-2-yl)thio)-2-(4-hydroxytetrahydro-2H-pyran-4-yl)-N-methyl-N-phenyl acetamide;

(S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(pyridin-2-yl)acetamide;

(S)-2-(((2S,3R,4S,5R,6R)-3,5-Di hydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(pyridin-3-yl)acetamide;

(S)-2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methyl-N-(pyridin-2-yl)acetamide;

N-Cyclobutyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxytetrahydro-2H-pyran-4-yl)acetamide;

N-Cyclobutyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methylacetamide;

(S)—N-Cyclopropyl-2-(4,4-difluoro-1-hydroxycyclohexyl)-N-ethyl-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide;

(R)—N-(Cyclopropylmethyl)-2-(4,4-difluoro-1-hydroxycyclohexyl)-N-ethyl-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide;

2-(4,4-Difluoro-1-hydroxycyclohexyl)-N-ethyl-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-((tetrahydro-2H-pyran-4-yl)methyl)acetamide;

N-Benzyl-2-(4,4-difluoro-1-hydroxycyclohexyl)-N-ethyl-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide;

2-(4,4-Difluoro-1-hydroxycyclohexyl)-N4(3,3-difluorocyclobutyl)methyl)-N-ethyl-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide;

2-(4,4-Difluoro-1-hydroxycyclohexyl)-N-ethyl-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-(tetrahydro-2H-pyran-4-yl)acetamide;

2-(((2S,3R,4S,5R,6R)-4-(4-(3,5-Difluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

N-Ethyl-2-(((2S,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)thio)-2-(4-hydroxytetrahydro-2H-pyran-4-yl)-N-methylacetamide;

2-(((2S,3R,4S,5R,6R)-4-(4-(3,5-Difluoro-4-methylphenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

2-(((2S,3R,4S,5R,6R)-4-(4-(4-Chloro-3,5-difluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

2-(((2S,3R,4S,5R,6R)-4-(4-(4-Bromothiazol-2-yl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

2-(((2S,3R,4S,5R,6R)-4-(4-(4-Bromo-3-fluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

2-(((2S,3R,4S,5R,6R)-4-(4-(3-Chloro-5-fluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

2-(((2S,3R,4S,5R,6R)-4-(4-(3-Chloro-4,5-difluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

2-(((2S,3R,4S,5R,6R)-4-(4-(3,4-Difluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

2-(((2S,3R,4S,5R,6R)-4-(4-(3,4-Dichloro-5-fluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

2-(((2S,3R,4S,5R,6R)-4-(4-(4-Bromo-3,5-difluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

2-(((2S,3R,4S,5R,6R)-4-(4-(3-Cyano-5-methylphenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

N-Ethyl-2-(((2S,3R,4S,5R,6R)-4-(4-(3-fluoro-5-methylphenyl)-1H-1,2,3-triazol-1-yl)-3,5-dihydroxy-6-(hydroxymethyl)tetrahydro-2H-pyran-2-yl)thio)-2-(4-hydroxytetrahydro-2H-pyran-4-yl)-N-methylacetamide;

(R)—N-Cyclopropyl-2-(4,4-difluoro-1-hydroxycyclohexyl)-2-(((2S,3R,4S,5R,6R)-4-(4-(6-fluoro-5-methylpyridin-3-yl)-1H-1,2,3-triazol-1-yl)-3,5-dihydroxy-6-(hydroxymethyl)tetrahydro-2H-pyran-2-yl)thio)-N-methylacetamide;

(S)—N-Cyclopropyl-2-(4,4-difluoro-1-hydroxycyclohexyl)-2-(((2S,3R,4S,5R,6R)-4-(4-(6-fluoro-5-methylpyridin-3-yl)-1H-1,2,3-triazol-1-yl)-3,5-dihydroxy-6-(hydroxymethyl)tetrahydro-2H-pyran-2-yl)thio)-N-methylacetamide;

(S)-2-(4,4-Difluoro-1-hydroxycyclohexyl)-N-(2-fluoro-2-methylpropyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide;

(S)-2-(4,4-Difluoro-1-hydroxycyclohexyl)-1-(4,4-difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)ethan-1-one;

N-(Cyclopropylmethyl)-2-(4,4-difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide;

2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N,N-dimethyl acetamide;

2-(4,4-Difluoro-1-hydroxycyclohexyl)-N-ethyl-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide;

2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methyl-N-(2,2,2-trifluoroethyl)acetamide;

2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-isopropyl-N-methylacetamide;

2-(4,4-Difluoro-1-hydroxycyclohexyl)-N-(3,3-dimethylbutyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide;

N-(2-Cyclopropylethyl)-2-(4,4-difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide;

2-(4,4-Difluoro-1-hydroxycyclohexyl)-N-(3,3-difluorocyclobutyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide;

2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methyl-N-(oxetan-3-yl)acetamide;

2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methyl-N-(tetrahydro-2H-pyran-4-yl)acetamide;

2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-1-morpholinoethan-1-one;

2-(4,4-Difluoro-1-hydroxycyclohexyl)-1-(4,4-dimethylpiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)ethan-1-one;

N-(Bicyclo[1.1.1]pentan-1-yl)-2-(4,4-difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide;

2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-(tetrahydro-2H-pyran-4-yl)acetamide;

2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-(pentan-3-yl)acetamide;

2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-isopropylacetamide;

2-(4,4-Difluoro-1-hydroxycyclohexyl)-N-(3,3-difluorocyclobutyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide;

2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-(2,2,2-trifluoroethyl)acetamide;

1-(4,4-Difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-(6-hydroxyspiro[2.5]octan-6-yl)ethan-1-one;

1-(4,4-Difluoropiperidin-1-yl)-2-(1-hydroxy-4,4-dimethylcyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)ethan-1-one;

(S)-1-(4,4-Difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-(7-hydroxyspiro[3.5]nonan-7-yl)ethan-1-one;

1-(4,4-Difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-(7-hydroxy-2-oxaspiro[3.5]nonan-7-yl)ethan-1-one;

(S)-1-(4,4-Difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-(8-hydroxyspiro[4.5]decan-8-yl)ethan-1-one;

(S)-1-(4,4-Difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-(9-hydroxy-3-oxaspiro[5.5]undecan-9-yl)ethan-1-one;

1-(4,4-Difluoropiperidin-1-yl)-2-(4-hydroxy-2,2-dimethyltetrahydro-2H-pyran-4-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)ethan-1-one;

2-(1,1-Difluoro-6-hydroxyspiro[2.5]octan-6-yl)-1-(4,4-difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)ethan-1-one; and 2-(4,4-Difluoro-1-hydroxycyclohexyl)-1-(4,4-difluoropiperidin-1-yl)-2-(((2S,3R,4S,5R,6R)-3-ethoxy-5-hydroxy-6-(hydroxymethyl)-4-(4-(3,4,5-trifluorophenyl)-1H-1,2,3-triazol-1-yl)tetrahydro-2H-pyran-2-yl)thio)ethan-1-one.

25) In addition to the compounds listed in embodiment 21), further compounds according to embodiment 1) are selected from the following compounds:

(S)—N-(Cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxytetrahydro-2H-pyran-4-yl)acetamide;

(S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(oxetan-3-yl)acetamide;

(2R,3R,4S,5R,6S)-2-(Acetoxymethyl)-6-(((S)-2-(ethyl(methyl)amino)-1-(3-hydroxy-1-(methoxycarbonyl)azetidin-3-yl)-2-oxoethypthio)-4-(4-(3,4,5-trifluorophenyl)-1H-1,2,3-triazol-1-yl)tetrahydro-2H-pyran-3,5-diyl diacetate;

N-Cyclopropyl-4-((S)-2-(ethyl(methyl)amino)-1-(((2S,3R, 4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-oxoethyl)-4-hydroxypiperidine-1-carboxamide;

(S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxytetrahydro-2H-pyran-4-yl)-N-phenylacetamide;

(S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-phenylacetamide;

(S)-2-(((2S,3R,4S,5R,6R)-3,5-Di hydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(pyridin-2-yl)acetamide;

(S)-2-(((2S,3R,4S,5R,6R)-3,5-Di hydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(pyridin-3-yl)acetamide;

(S)-2-(4,4-Difluoro-1-hydroxycyclohexyl)-2-(((2S,3R,4S, 5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methyl-N-(pyridin-2-yl) acetamide;

(S)—N-Cyclobutyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxytetrahydro-2H-pyran-4-yl)acetamide;

(S)—N-Cyclobutyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methylacetamide;

(S)—N-Cyclopropyl-2-(4,4-difluoro-1-hydroxycyclohexyl)-N-ethyl-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide;

(S)—N-(Cyclopropyl methyl)-2-(4,4-difluoro-1-hydroxycyclohexyl)-N-ethyl-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide;

(S)-2-(4,4-Difluoro-1-hydroxycyclohexyl)-N-ethyl-2-(((2S, 3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-((tetrahydro-2H-pyran-4-yl)methyl)acetamide;

(S)—N-Benzyl-2-(4,4-difluoro-1-hydroxycyclohexyl)-N-ethyl-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide;

(S)-2-(4,4-Difluoro-1-hydroxycyclohexyl)-N-((3,3-difluorocyclobutyl)methyl)-N-ethyl-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide;

(S)-2-(4,4-Difluoro-1-hydroxycyclohexyl)-N-ethyl-2-(((2S, 3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-(tetrahydro-2H-pyran-4-yl)acetamide;

(S)-2-(((2S,3R,4S,5R,6R)-4-(4-(3,5-Difluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

(S)—N-Ethyl-2-(((2S,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)thio)-2-(4-hydroxytetrahydro-2H-pyran-4-yl)-N-methylacetamide;

(S)-2-(((2S,3R,4S,5R,6R)-4-(4-(3,5-Difluoro-4-methylphenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

(S)-2-(((2S,3R,4S,5R,6R)-4-(4-(4-Chloro-3,5-difluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

(S)-2-(((2S,3R,4S,5R,6R)-4-(4-(4-Bromothiazol-2-yl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

(S)-2-(((2S,3R,4S,5R,6R)-4-(4-(4-Bromo-3-fluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

(S)-2-(((2S,3R,4S,5R,6R)-4-(4-(3-Chloro-5-fluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

(S)-2-(((2S,3R,4S,5R,6R)-4-(4-(3-Chloro-4,5-difluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

(S)-2-(((2S,3R,4S,5R,6R)-4-(4-(3,4-Difluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

(S)-2-(((2S,3R,4S,5R,6R)-4-(4-(3,4-Dichloro-5-fluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

(S)-2-(((2S,3R,4S,5R,6R)-4-(4-(4-Bromo-3,5-difluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

(S)-2-(((2S,3R,4S,5R,6R)-4-(4-(3-Cyano-5-methyl phenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

(S)—N-Ethyl-2-(((2S,3R,4S,5R,6R)-4-(4-(3-fluoro-5-methylphenyl)-1H-1,2,3-triazol-1-yl)-3,5-dihydroxy-6-(hydroxymethyl)tetrahydro-2H-pyran-2-yl)thio)-2-(4-hydroxytetrahydro-2H-pyran-4-yl)-N-methylacetamide;

(S)—N-Cyclopropyl-2-(4,4-difluoro-1-hydroxycyclohexyl)-2-(((2S,3R,4S,5R,6R)-4-(4-(6-fluoro-5-methylpyridin-3-yl)-1H-1,2,3-triazol-1-yl)-3,5-dihydroxy-6-(hydroxymethyl)tetrahydro-2H-pyran-2-yl)thio)-N-methylacetamide;

(S)-2-(4,4-Difluoro-1-hydroxycyclohexyl)-N-(2-fluoro-2-methylpropyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide;

(S)-2-(4,4-Difluoro-1-hydroxycyclohexyl)-1-(4,4-difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)ethan-1-one;

(S)—N-(Cyclopropylmethyl)-2-(4,4-difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide;

(S)-2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N,N-dimethylacetamide;

(S)-2-(4,4-Difluoro-1-hydroxycyclohexyl)-N-ethyl-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide;

(S)-2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methyl-N-(2,2,2-trifluoroethyl)acetamide;

(S)-2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-isopropyl-N-methylacetamide;

(S)-2-(4,4-Difluoro-1-hydroxycyclohexyl)-N-(3,3-dimethylbutyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide;

(S)—N-(2-Cyclopropylethyl)-2-(4,4-difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide;

(S)-2-(4,4-Difluoro-1-hydroxycyclohexyl)-N-(3,3-difluorocyclobutyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide;

(S)-2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methyl-N-(oxetan-3-yl)acetamide;

(S)-2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methyl-N-(tetrahydro-2H-pyran-4-yl)acetamide;

(S)-2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-1-morpholinoethan-1-one;

(S)-2-(4,4-Difluoro-1-hydroxycyclohexyl)-1-(4,4-dimethylpiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)ethan-1-one;

(S)-2-(4,4-Difluoro-1-hydroxycyclohexyl)-N-(4,4-dimethylcyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide;

(S)—N-(Bicyclo[1.1.1]pentan-1-yl)-2-(4,4-difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide;

(S)-2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide;

(S)-2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-(tetrahydro-2H-pyran-4-yl)acetamide;

(S)-2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-(pentan-3-yl)acetamide;

(S)-2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-isopropylacetamide;

(S)-2-(4,4-Difluoro-1-hydroxycyclohexyl)-N-(3,3-dimethylbutyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide;

(S)-2-(4,4-Difluoro-1-hydroxycyclohexyl)-N-(3,3-difluorocyclobutyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide;

(S)-2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-(2,2,2-trifluoroethyl)acetamide;

(S)-2-(4,4-Difluoro-1-hydroxycyclohexyl)-N-(4,4-dimethylcyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide;

(S)-1-(4,4-Difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-(6-hydroxyspiro[2.5]octan-6-yl)ethan-1-one;

(S)-1-(4,4-Difluoropiperidin-1-yl)-2-(1-hydroxy-4,4-dimethylcyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)ethan-1-one;

(S)-1-(4,4-Difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-(7-hydroxyspiro[3.5]nonan-7-yl)ethan-1-one;

(S)-1-(4,4-Difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-(7-hydroxy-2-oxaspiro[3.5]nonan-7-yl)ethan-1-one;

(S)-1-(4,4-Difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-(8-hydroxyspiro[4.5]decan-8-yl)ethan-1-one;

(S)-1-(4,4-Difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-(9-hydroxy-3-oxaspiro[5.5]undecan-9-yl)ethan-1-one;

(S)-1-(4,4-Difluoropiperidin-1-yl)-2-((R)-4-hydroxy-2,2-dimethyltetrahydro-2H-pyran-4-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)ethan-1-one;

(S)-1-(4,4-Difluoropiperidin-1-yl)-2-((3)-4-hydroxy-2,2-di methyltetrahydro-2H-pyran-4-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)ethan-1-one;

(2S)-2-(1,1-Difluoro-6-hydroxyspiro[2.5]octan-6-yl)-1-(4, 4-difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)ethan-1-one; and (S)-2-(4,4-Difluoro-1-hydroxycyclohexyl)-1-(4,4-difluoropiperidin-1-yl)-2-(((2S,3R,4S,5R,6R)-3-ethoxy-5-hydroxy-6-(hydroxymethyl)-4-(4-(3,4,5-trifluorophenyl)-1H-1,2,3-triazol-1-yl)tetrahydro-2H-pyran-2-yl)thio)ethan-1-one.

The compounds of Formula (I) according to embodiments 1) to 25) and their pharmaceutically acceptable salts can be used as medicaments, e.g. in the form of pharmaceutical compositions for enteral (such especially oral e.g. in form of a tablet or a capsule) or parenteral administration (including topical application or inhalation).

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of Formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention/prophylaxis or treatment of a disease or disorder mentioned herein comprising administering to a subject a pharmaceutically active amount of a compound of Formula (I) according to embodiments 1) to 25). In a sub-embodiment of the invention, the administered amount is comprised between 1 mg and 1000 mg per day.

For avoidance of any doubt, if compounds are described as useful for the prevention/prophylaxis or treatment of certain diseases, such compounds are likewise suitable for use in the preparation of a medicament for the prevention/prophylaxis or treatment of said diseases. Likewise, such compounds are also suitable in a method for the prevention/prophylaxis or treatment of such diseases, comprising administering to a subject (mammal, especially human) in need thereof, an effective amount of such compound.

26) Another embodiment relates to the compounds of formula (I) as defined in any one of embodiments 1) to 25) which are useful for the prevention/prophylaxis or treatment of diseases and disorders that are related to galectin-3 binding to natural ligands.

Such diseases and disorders that are related to Gal-3 binding to natural ligands are especially diseases and disorders in which inhibition of the physiological activity of Gal-3 is useful, such as diseases in which a Gal-3 receptor participates, is involved in the etiology or pathology of the disease, or is otherwise associated with at least one symptom of the disease.

Diseases or disorders that are related to galectin-3 binding to natural ligands may in particular be defined as including:

fibrosis of organs comprising:

all forms of lung/pulmonary fibrosis including all forms of fibrosing interstitial lung diseases, especially idiopathic pulmonary fibrosis (alternatively named cryptogenic fibrosing alveolitis); pulmonary fibrosis secondary to systemic inflammatory disease such as rheumatoid arthritis, scleroderma (systemic sclerosis, SSc), lupus (systemic lupus erythematosus, SLE), polymyositis, or mixed connective tissue disease (MCTD); pulmonary fibrosis secondary to sarcoidosis; iatrogenic pulmonary fibrosis including radiation-induced fibrosis; silicosis-induced pulmonary fibrosis; asbestos-induced pulmonary fibrosis; and pleural fibrosis;

renal/kidney fibrosis, including renal fibrosis caused by/associated with chronic kidney disease (CKD), (acute or chronic) renal failure, tubulointerstitial nephritis, and/or chronic nephropathies such as (primary) glomerulonephritis and glomerulonephritis secondary to systemic inflammatory diseases such as SLE or SSc, diabetes, focal segmental glomerular sclerosis, IgA nephropathy, hypertension, renal allograft, and Alport syndrome;

all forms of liver/hepatic fibrosis (associated or not with portal hypertension) including cirrhosis, alcohol-induced liver fibrosis, nonalcoholic steatohepatitis, biliary duct injury, primary biliary cirrhosis (also known as primary biliary cholangitis), infection- or viral-induced liver fibrosis (e.g. chronic HCV infection), and autoimmune hepatitis;

all forms of heart/cardiac fibrosis, including heart/cardiac fibrosis associated with cardiovascular diseases, heart failure, Fabry disease, CKD; diabetes, hypertension, or hypercholesterolemia;

gut fibrosis, including gut fibrosis secondary to SSc, and radiation-induced gut fibrosis;

skin fibrosis, including SSc and skin scarring;

head and neck fibrosis, including radiation-induced head and neck fibrosis;

eye/corneal fibrosis, including scarring (e.g. sequelae of laser-assisted in situ keratomileusis, or trabeculectomy);

hypertrophic scarring and keloids, including burn-induced or surgical hypertrophic scarring and keloids;

fibrosis sequelae of organ transplant (including corneal transplant);

and other fibrotic diseases including endometriosis, spinal cord fibrosis, myelofibrosis, perivascular and aterial fibrosis; as well as formation of scar tissue, Peyronie's disease, abdominal or bowel adhesions, bladder fibrosis, fibrosis of the nasal passages, and fibrosis mediated by fibroblasts;

(acute or chronic) liver diseases and disorders including acute and chronic viral hepatitis; cirrhosis caused by/associated with arthritis and vasculitis; metabolic liver diseases caused by/associated with arthritis, myocarditis, diabetes, or neurologic symptoms; cholestatic diseases caused by/associated with hyperlipidaemia, inflammatory bowel disease (IBD), or ulcerative colitis; liver tumors; autoimmune hepatitis and cirrhosis caused by/associated with celiac disease, autoimmune haemolytic anaemia, IBD, autoimmune thyroiditis, ulcerative colitis, diabetes, glomerulonephritis, pericarditis, autoimmune thyroiditis, hyperthyroidism, polymyositis, Sjörgen syndrome, panniculitis, alveolitis or alcoholic steatosis; cirrhosis associated with dementia; cirrhosis associated with peripheral neuropathy; cirrhosis caused by/associated with oral or oesophageal cancer; non-alcoholic fatty liver disease (especially non-alcoholic steatohepatitis) caused by/associated with obesity, metabolic syndrome or type 2 diabetes; hepatic blood vessel disorders (including Budd-Chiari syndrome, portal vein thrombosis, sinusoidal obstruction syndrome); acute and chronic liver failure (associated or not with portal hypertension); liver hypofunction;

acute kidney injury and chronic kidney disease (CKD) [especially CKD of stages 1 to 5 as defined by the Kidney Disease Improving Global Outcomes (KDIGO) Guidelines], in particular CKD (notably of these stages) caused by/associated with cardiac diseases (also referred to as cardio-renal syndrome type 1 and type 2), or caused by/associated with hypertension, or caused by/associated with diabetes (also referred to as diabetic kidney disease (DKD), including DKD associated with hypertension), wherein such diabetes especially is type 1 or type 2 diabetes), or caused by/associated with inflammatory diseases and disorders (such as glomerulonephritis and glomerulonephritis secondary to systemic inflammatory diseases such as SLE or SSc, tubulo-interstitial nephritis, vasculitis, sepsis, urinary tract infection), or caused by/associated with polycystic kidney disease, or caused by/associated with obstructive nephropathy (including calculi, benign prostatic hyperplasia, prostate cancer, retroperitoneal pelvic tumor), or caused by/associated with symptoms associated with neuropathic bladder disease); as well as acute and chronic renal failure;

cardiovascular diseases and disorders (including atherosclerosis caused by/associated with hypertension, hypercholesterolemia, diabetes, inflammation, obesity, elderly/age; peripheral arterial disease caused by/associated with hypertension, hypercholesterolemia, diabetes, elderly/age; deep venous thrombosis; pulmonary embolism caused by/associated with obesity or cancer; aortic aneurysm and dissection caused by/associated with elderly/age, hypertension, Marfan syndrome, congenital heart disorders, inflammatory or infectious disorders; cerebrovascular disease caused by/associated with hypertension, atrial fibrillation, hypercholesterolemia, diabetes, elderly/age; coronary heart disease caused by/associated with hypertension, hypercholesterolemia, diabetes, elderly/age, or CKD (especially CKD of stages 1 to 5 as defined by the Kidney Disease Improving Global Outcomes (KDIGO) Guidelines); rheumatic heart disease caused by/associated with bacterial infection; heart and vascular tumors; cardiomyopathy and arrythmias; valvular heart disease (including valvular calcification and degenerative aortic stenosis); inflammatory heart disease caused by/associated with infection, carditis, glomerulonephritis, cancer; heart failure (HF) defined as including especially congestive HF, including in particular systolic HF/HF with reduced ejection fraction (HFrEF), and diastolic HF/HF with preserved ejection fraction (HFpEF);

interstitial lung diseases and disorders (including smoking-related interstitial lung disease; interstitial lung disease associated with/caused by chronic obstructive pulmonary disease; interstitial pneumonia associated with collagen vascular disease (including usual interstitial pneumonia), or pneumonia);

cell proliferative diseases and cancers (including solid tumors, solid tumor metastasis, carcinoma, sarcoma, myeloma (and multiple myeloma), leukemia, lymphoma, mixed types of cancers, vascular fibroma, Kaposi's sarcoma, chronic lymphocytic leukemia (CLL), spinal cord tumors and invasive metastasis of cancer cells);

inflammatory and autoimmune diseases and disorders including chronic and acute inflammatory and autoimmune diseases and disorders (in particular including sepsis, Q-fever, asthma, rheumatoid arthritis, multiple sclerosis, SLE, SSc, polymyositis, plaque psoriasis (including psoriasis caused by/associated with NASH), atopic dermatitis, inflammatory renal/kidney diseases such as nephropathy (including diabetic nephropathy, glomerulonephritis, tubulointerstitial nephritis), inflammatory cardiac/heart diseases, inflammatory lung/lung related diseases; inflammatory liver/liver related diseases; diabetes (type 1 or type 2) and diabetes related diseases such as diabetic vasculopathy, diabetic nephropathy, diabetic retinopathy, diabetic peripheral neuropathy or skin related condition; viral encephalitis; and COVID-19 and sequelae thereof);

gastrointestinal tract diseases and disorders (including irritable bowel syndrome (IBS), inflammatory bowel disease (IBD), gastritis, and abnormal pancreatic secretion);

pancreatic diseases and disorders (including pancreatitis, e.g. associated with cystic fibrosis);

abnormal angiogenesis-associated diseases and disorders (including arterial obstruction);

brain-associated diseases and disorders (including stroke and cerebral haemorrhage);

neuropathic pain and peripheral neuropathy;

ocular diseases and disorders (including dry eye disease (dry eye syndrome), macular degeneration (AMD associated with age, diabetes related disease (diabetic retinopathy), proliferative vitreoretinopathy (PVR), cicatricial pemphigoid, and glaucoma (including glaucoma associated with elevated intraocular pressure, and ocular scarring after glaucoma filtration surgery), and corneal angiogenesis/neovascularization); and transplant rejection comprising rejection of transplanted organs such as kidney, liver, heart, lung, pancreas, cornea, and skin; graft-versus-host diseases brought about by hematopoietic stem cell transplantation; chronic allograft rejection and chronic allograft vasculopathy; and sequelae of such transplant rejection.

27) A further embodiment relates to the compounds of formula (I) for use according to embodiment 26) wherein said compounds are for use in the prevention/prophylaxis or treatment of fibrosis of organs including liver/hepatic fibrosis, renal/kidney fibrosis, lung/pulmonary fibrosis, heart/cardiac fibrosis, eye/corneal fibrosis, and skin fibrosis; as well as gut fibrosis, head and neck fibrosis, hypertrophic scarring and keloids; and fibrosis sequelae of organ transplant.

28) A further embodiment relates to the compounds of formula (I) for use according to embodiment 26) wherein said compounds are for use in the prevention/prophylaxis or treatment of cardiovascular diseases and disorders.

29) A further embodiment relates to the compounds of formula (I) for use according to embodiment 26) wherein said compounds are for use in the prevention/prophylaxis or treatment of acute kidney injury and chronic kidney disease (CKD).

30) A further embodiment relates to the compounds of formula (I) for use according to embodiment 26) wherein said compounds are for use in the prevention/prophylaxis or treatment of (acute or chronic) liver diseases and disorders.

31) A further embodiment relates to the compounds of formula (I) for use according to embodiment 26) wherein said compounds are for use in the prevention/prophylaxis or treatment of interstitial lung diseases and disorders.

32) A further embodiment relates to the compounds of formula (I) for use according to embodiment 26) wherein said compounds are for use in the prevention/prophylaxis or treatment of ocular diseases and disorders.

33) A further embodiment relates to the compounds of formula (I) for use according to embodiment 26) wherein said compounds are for use in the prevention/prophylaxis or treatment of cell proliferative diseases and cancers.

34) A further embodiment relates to the compounds of formula (I) for use according to embodiment 26) wherein said compounds are for use in the prevention/prophylaxis or treatment of chronic or acute inflammatory and autoimmune diseases and disorders.

35) A further embodiment relates to the compounds of formula (I) for use according to embodiment 26) wherein said compounds are for use in the prevention/prophylaxis or treatment of gastrointestinal tract diseases and disorders.

36) A further embodiment relates to the compounds of formula (I) for use according to embodiment 26) wherein said compounds are for use in the prevention/prophylaxis or treatment of pancreatic diseases and disorders.

37) A further embodiment relates to the compounds of formula (I) for use according to embodiment 26) wherein said compounds are for use in the prevention/prophylaxis or treatment of abnormal angiogenesis-associated diseases and disorders.

38) A further embodiment relates to the compounds of formula (I) for use according to embodiment 26) wherein said compounds are for use in the prevention/prophylaxis or treatment of brain-associated diseases and disorders.

39) A further embodiment relates to the compounds of formula (I) for use according to embodiment 26) wherein said compounds are for use in the prevention/prophylaxis or treatment of neuropathic pain and peripheral neuropathy.

40) A further embodiment relates to the compounds of formula (I) for use according to embodiment 26) wherein said compounds are for use in the treatment of transplant rejection.

Preparation of Compounds of Formula (I):

The compounds of Formula (I) can be prepared by well-known literature methods, by the methods given below, by the methods given in the experimental part below or by analogous methods. Optimum reaction conditions may vary with the particular reactants or solvents used, but such conditions can be determined by a person skilled in the art by routine optimization procedures. In some cases, the order of carrying out the following reaction schemes, and/or reaction steps, may be varied to facilitate the reaction or to avoid unwanted reaction products. In the general sequence of reactions outlined below, the generic groups $R^1$, $R^{2a}$, $R^{2b}$, $R^3$ and $Ar^1$ are as defined for Formula (I). Other abbreviations used herein are explicitly defined or are as defined in the experimental section. In some instances, the generic groups $R^1$, $R^{2a}$, $R^{2b}$, $R^3$ and $Ar^1$ might be incompatible with the assembly illustrated in the schemes below and so will require the use of protecting groups (Pg). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as necessary are in place. In some cases, the final product may be further modified, for example, by manipulation of substituents to give a new final product. These manipulations may include, but are not limited to, reduction, oxidation, alkylation, acylation, hydrolysis and transition-metal catalyzed cross-coupling reactions which are commonly known to those skilled in the art. The compounds obtained may also be converted into salts, especially pharmaceutically acceptable salts, in a manner known per se.

Compounds of Formula (I) of the present invention can be prepared according to the general sequence of reactions outlined below. Only a few of the synthetic possibilities leading to compounds of Formula (I) are described.

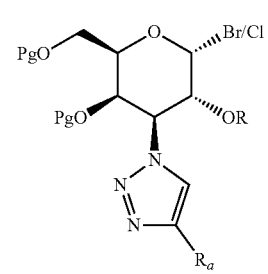

Structure 1

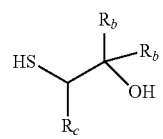

Structure 2

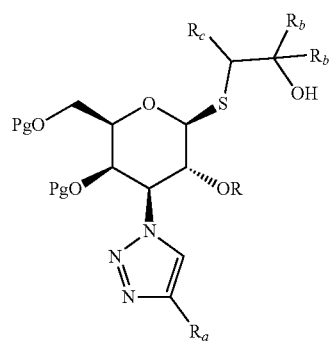

Structure 3

Compounds of Formula (I) are prepared e.g. by reacting a compound of Structure 1 where R is either hydrogen, a suitable protective group (Pg) or $R^1$ (as defined in Formula (I)) with a compound of Structure 2 in a solvent such as EA/water under phase transfer catalytic conditions in presence of tetrabutyl ammonium bromide or tetrabutyl ammonium hydrogensulfate and a base such as $Na_2CO_3$ (Chem. Comm. 2006, 2379). Alternatively compound of Structure 1 can react with a compound of Structure 2 under anhydrous conditions in THF or DMF in presence of NaH to give a compound of Structure 3. In Structures 1 and 3, the term Pg represents a protective group such as an acetyl, a chloroacetyl, a benzoyl, or a benzyl group or a 4-clorobenzyl, which are well known to the person skilled in the art. The hydroxy groups in position 4 and 6 of Structure 1 can be protected with cyclic protective groups such as isopropylidene, benzylidene or bis-tert-butyl silyl groups. R is either hydrogen, a suitable protective group (Pg) or $R^1$ (as defined in Formula (I)). In the case wherein Pg represents an acyl protective group, such a protective group can be cleaved following the reaction of a compound of Structure 1 with a compound of Structure 2 under standard conditions, e.g. by water or an alcohol in the presence or absence of additional solvents such as THF, dioxane, etc. and in the presence of a base such as NaOH, or LiOH. In the case wherein such a protective group represents a benzyl group, the protective group can be cleaved e.g. by hydrogen in the presence of a catalyst such as Pd/C, PtO in methanol, ethyl acetate, THF, etc. or mixtures thereof, or by BBr$_3$ in a solvent such as DCM. In the case where Pg is a cyclic protective group such as isopropylidene, benzylidene or bis-tert-butyl silyl groups and R is either hydrogen, a suitable protective group (Pg) or R$^1$ (as defined in Formula (I)), the compounds of Structure 3 can be deprotected under acidic conditions using aqueous acetic acid or TFA.

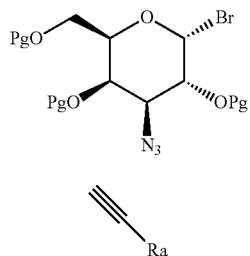

Structure 4

Structure 5

The compounds of Structure 1 can be prepared e.g. by reacting a compound of Structure 4 with a compound of Structure 5 in the presence of CuI and DIPEA in solvents such as THF or DMF(*Click Chemistry in Glycoscience: New Development and Strategies*, 1st Edition, 2013, John Wiley& Sons), alternatively the reaction can be run on a commercial continuous-flow reactor (Vapourtec) using a copper coil in a solvent such as THF. Compound of Structure 5 are either commercially available or can be prepared according to procedures known to a person skilled in the art (*Synthesis* 2011, 22, 3604-3611). Compounds of Structure 4 can be prepared in 3 steps from gluco furanose through methods well known to a person skilled in the art (*Carbohydrate Research* 1994, 251, 33-67).

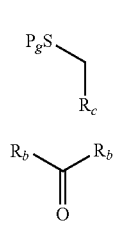

Structure 6

Structure 7

The compounds of Structure 2 can be prepared by reacting a compound of Structure 6 in presence of a strong base such as LDA or n-BuLi in solvents such as THF, diethylether, toluene, with a compound of Structure 7 at low temperatures. (*Chem Lett* 1977, 471-474). In Structure 6, the term Pg represents a suited protective group for the thiol, such as an acyl or a tetrahydropyrane. In the case wherein such a protective group represents an acyl protective group, such a protective group can be cleaved following the reaction of compound of Structure 6 with a compound of Structure 7 under standard conditions, e.g. by water or an alcohol in the presence or absence of additional solvents such as THF, dioxane, etc. and in the presence of a base such as NaOH, LiOH, or 25% NH$_4$OH. In the case wherein such a protective group represents a tetrahydopyrane group, the protective group can be cleaved following the reaction of a compound of Structure 6 with a compound of Structure 7 e.g. by AgNO$_3$ in a solvent mixture such as THF/water, followed by treatment of the silver salt with NaSH in a solvent mixture such as THF/DCM/water (*Tetrahedron* 59 2003,3853-3861), alternatively a combination of boron trifluoride, 2-mercaptoethanol in a solvent such as DCM can be used (*Chem Lett* 1996, 999-1000).

Structure 6A

In case Rc is an ester group the compound of Structure 2 can be also prepared from a compound of Structure 6A whereby no protecting group for the thiol is needed (*Chem Lett* 1977, 471-474). Compounds of Structure 7 and compounds of Structure 6A are commercially available.

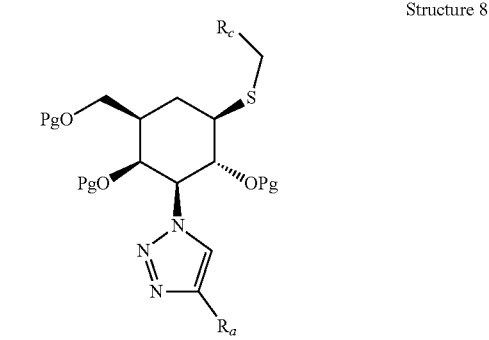

Structure 8

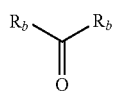

Structure 7

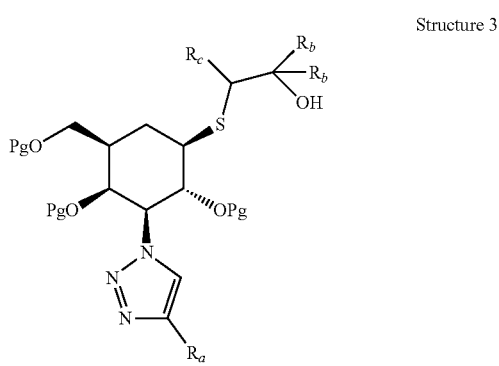

Structure 3

Compounds of Structure 3 can be obtained by reacting compounds of Structure 8 and compounds of Structure 7 in presence of a strong base such as LDA or n-BuLi in solvents such as THF, diethylether, toluene, at low temperatures such as −78° C. (*Chem Lett* 1977, 471-474).

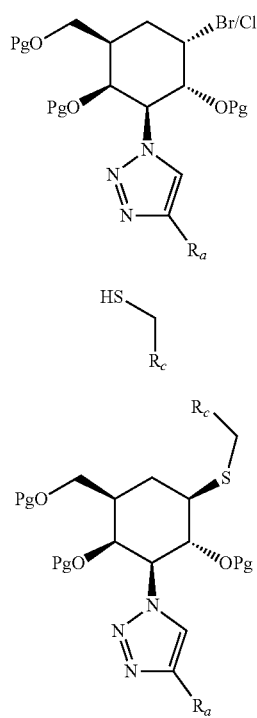

Structure 1

Structure 9

Structure 8

Compounds of Structure 8 can be synthesized by reacting compounds of Structure 1 with compounds of Structure 9 under the conditions described earlier for reaction of compound of Structure 2 and Structure 3, eg under phase transfer catalytic conditions in presence of tetrabutyl ammonium bromide or tetrabutyl ammonium hydrogensulfate and a base such as $Na_2CO_3$ (*Chem. Comm.* 2006, 2379) or under anhydrous conditions, in THF or DMF in presence of NaH. Compounds of Structure 9 are commercially available.

Whenever the compounds of Formula (I) are obtained in the form of mixtures of stereoisomers, the stereoisomers can be sometimes separated by preparative HPLC or more often by HPLC over a chiral stationary phase such as a Daicel ChiralCel OJ-H (5-10 μm) column, or a Daicel ChiralPak IH (5 μm) or AS-H (5 μm) or IB (5 μm) column. Typical conditions of chiral HPLC are an isocratic mixture of eluent A ($CO_2$) and eluent B (DCM/MeOH, 0.1% $Et_2NH$ in EtOH, MeOH, EtOH), at a flow rate of 0.8 to 160 mL/min.

Experimental Part

The following examples illustrate the invention but do not at all limit the scope thereof.

All temperatures are stated in ° C. Commercially available starting materials are used as received without further purification. Unless otherwise indicated, the reactions take place at rt under a nitrogen atmosphere and are run in a flame dried round-bottomed flask equipped with a magnetic stir bar. Compounds are purified by flash chromatography on silica gel (Kieselgel 60, 60 Å, 35-70 μM), by prep TLC (TLC-plates from Merck, Silica gel 60 $F_{254}$) or by preparative HPLC/MS or Flashmaster (Büchi or ISCO). Compounds described in the invention are characterized by $^1$H-NMR (Bruker Avance II, 400 MHz Ultra Shield™ or Brooker Avance III HD, Ascend 500 MHz; chemical shifts are given in ppm relative to the solvent used; multiplicities: s=singlet, d=doublet, t=triplet, q=quadruplet, quint=quintuplet, hex=hexet, hept=heptet, m=multiplet, br=broad, coupling constants are given in Hz) and/or by LCMS (retention time $t_R$ is given in min; molecular weight obtained for the mass spectrum is given in g/mol) or chiral HPLC (retention time $t_R$ is given in min) using the conditions listed below.

Abbreviations (as Used Herein)

ABTS 2,2'-Azino-bis(3-ethylbenzothiazoline-6-sulfonic acid
AcOH acetic acid
$AgNO_3$ silver nitrate
$AgO_2$ silveroxide
aq. aqueous
Bu butyl (such as in nBuLi=n-butyl lithium)
CC column chromatography on silica
conc. concentrated
CSA 10-camphor-sulfonic acid
CuI copper iodide
DBU 1,8-diazabicyclo[5.4.0]undec-7-ene
DCM dichloromethane
DEAD diethyl azodicarboxylate
DIPEA N-ethyl diisopropyl amine
DMAP 4-dimethylamino pyridine
DMF dimethylformamide
DMSO dimethylsulfoxide
EA ethyl acetate
EtI ethyl iodide
*E. coli. Escherichia coli*
EDC HCl N-(3-dimethylaminopropyl)-N'-ethylcarbodiimide hydrochloride
eq (molar) equivalent(s)
Et ethyl
EtOH ethanol
$Et_2O$ diethyl ether
FC flash chromatography
h hour(s)
HATU 1-[Bis(dimethylamino)methylene]-1H-1,2,3-triazolo[4,5-b]pyridinium 3-oxid hexafluorophosphate
$HClO_4$ perchloric acid
Hept heptane
HOBt 1-hydroxybenzotriazole hydrate
HPLC high performance liquid chromatography
$K_2CO_3$ potassium carbonate
$KMnO_4$ potassium permanganate
LAH lithium aluminium hydride
LDA lithium diisopropylamide
LC liquid chromatography
M molarity [mol L$^{-1}$]
Me methyl
MeCN acetonitrile
MeI methyl iodide
MeOH methanol
$MgSO_4$ magnesium sulfate
MS mass spectroscopy
min. minute(s)
N normality
$Na_2CO_3$ sodium carbonate
$NaHCO_3$ sodium hydrogen carbonate
NaHMDS sodium bis-trimethylsilyl-amide or sodium hexamethyldisilazide
NaOAc sodium acetate
NaOMe sodium methoxide
NaOtBu sodium tert. (tertiary) butoxide
NaSH sodiumhydrogen sulfide
NBS N-bromosuccinimide
$NH_4Cl$ ammonium chloride
OD optical density
o/n over night
org. organic p-ABSA p-acetamidobenzenesulfonyl azide
Pd(Ph$_3$)$_4$ tetrakis(triphenylphosphine)palladium(0)
PPh$_3$ triphenylphosphine
Ph phenyl
PTSA p-Toluenesulfonic acid
rt room temperature
sat. saturated
SBr$_2$ thionylbromide
TBAB tetrabutylammonium bromide
TBAHS tetrabutyl ammonium hydrogensulfate
TBME tert-butylmethylether
TBTU O-benzotriazol-1-yl-N,N,N',N'-tetramethyluronium tetrafluoroborate
tBu tert-butyl=tertiary butyl
TEA triethylamine
TFA trifluoroacetic acid
THF tetrahydrofuran
TMEDA tetramethylethylenediamine
TMSCl trimethylsilyl chloride
TMS-SMe trimethyl(methylthio)silane
TMSOTf trimethylsilyl trifluoromethanesulfonate
T3P propylphosphonic anhydride
t$_R$ retention time Characterization Methods Used:

Values of inhibitory activity of compounds are determined in the biological assay described below. If not explicitly mentioned otherwise, the inhibition data refer to the binding of biotinylated human Gal-3 (hGal-3).

The LC-MS retention times are obtained using the following elution conditions:

A) LC-MS (A):

Zorbax RRHD SB-Aq, 1.8 μm, 2.1×50 mm column thermostated at 40° C. The two elution solvents are as follows: solvent A=water+0.04% TFA; solvent B=acetonitrile. The eluent flow rate is 4.5 mL/min and the characteristics of the eluting mixture proportion in function of the time t from start of the elution are summarized in the table below (a linear gradient being used between two consecutive time points):

|  | t (min) | | | | |
| --- | --- | --- | --- | --- | --- |
|  | 0 | 0.01 | 1.20 | 1.90 | 2.10 |
| Solvent A (%) | 95 | 95 | 5 | 5 | 95 |
| Solvent B (%) | 5 | 5 | 95 | 95 | 5 |

Detection: UV at 210 nm.

B) LC-MS (B):

Zorbax RRHD SB-Aq, 1.8 μm, 3.0×50 mm column thermostated at 40° C. The two elution solvents are as follows: solvent A=water+0.04% TFA; solvent B=acetonitrile. The eluent flow rate is 1.6 mL/min and the characteristics of the eluting mixture proportion in function of the time t from start of the elution are summarized in the table below (a linear gradient being used between two consecutive time points):

|  | t (min) | | | | |
| --- | --- | --- | --- | --- | --- |
|  | 0 | 0.01 | 1.20 | 1.90 | 2.00 |
| Solvent A (%) | 95 | 95 | 5 | 5 | 95 |
| Solvent B (%) | 5 | 5 | 95 | 95 | 5 |

Detection: UV at 210 nm.

C) LC-MS (C):

Waters BEH C18, 2.5 μm, 2.1×50 mm column thermostated at 40° C. The two elution solvents are as follows: solvent A=water+0.04% TFA; solvent B=acetonitrile. The eluent flow rate is 0.8 mL/min and the characteristics of the eluting mixture proportion in function of the time t from start of the elution are summarized in the table below (a linear gradient being used between two consecutive time points):

|  | t (min) | | | | |
| --- | --- | --- | --- | --- | --- |
|  | 0 | 1.2 | 1.9 | 2.1 | 0 |
| Solvent A (%) | 95 | 5 | 5 | 95 | 95 |
| Solvent B (%) | 5 | 5 | 95 | 95 | 5 |

Detection: UV at 210 nm.

D) Chiral Analytical HPLC (I):

Epimers of an epimers mixture are characterized by chiral analytical HPLC. Conditions vary for each epimers mixture. Several columns have been used, all have the same size: 4.6×250 mm, 5 μm. Elution is done at isocratic conditions: Eluent A is always $CO_2$, eluent B is either an organic solvent or a mixture thereof. Runs last from 2.5 to 5 min.

Column type, B solvent and the length of the run is mentioned for each epimer mixture in the corresponding Tables shown herewith.

E) Chiral Analytical HPLC (E):

Chiralpak OJ-H, 5 μm, 4.6×250 mm, column thermostated at 40° C. The two elution solvents are as follows: solvent A=$CO_2$; solvent B=MeOH. The eluent flow rate is 4.0 mL/min over 5 min. Elution: Isocratic 10% of the solvent B and 90% of the solvent A. Detection: 210 nm.

F) Chiral Analytical HPLC (F):

Chiralcel OJ-H, 5 μm, 4.6×250 mm, column thermostated at 40° C. The two elution solvents are as follows: solvent A=$CO_2$; solvent B=MeOH. The eluent flow rate is 4.0 mL/min over 5 min. Elution: Isocratic 15% of the solvent B and 85% of the solvent A. Detection: ELSD.

G) Chiral Analytical HPLC (G):

Chiralpak IC, 5 μm, 4.6×250 mm, column thermostated at 40° C. The two elution solvents are as follows: solvent A=$CO_2$; solvent B=EtOH. The eluent flow rate was 4.0 mL/min over 5 min. Elution: Isocratic 35% of the solvent B and 65% of the solvent A. Detection: 210 nm.

H) Chiral Analytical HPLC (H):

Chiralcel OJ-H, 5 μm, 4.6×250 mm, column thermostated at 40° C. The two elution solvents are as follows: solvent A=$CO_2$; solvent B=MeOH. The eluent flow rate is 4.0 mL/min over 3.5 min. Elution: Isocratic 15% of the solvent B and 85% of the solvent A. Detection: 210 nm.

J) Chiral Analytical HPLC (J): (I was Fine No?)

Chiralpak IH, 5 μm, 4.6×250 mm, column thermostated at 40° C. The two elution solvents are as follows: solvent A=$CO_2$; solvent B=MeCN/EtOH (1/1). The eluent flow rate is 4.0 mL/min over 5 min. Elution: Isocratic 20% of the solvent B and 80% of the solvent A. Detection: 210 nm.

K) Chiral Analytical HPLC (K): (and then J Here, Etc?)

Chiralcel OJ-H, 5 μm, 4.6×250 mm, column thermostated at 40° C. The two elution solvents are as follows: solvent A=$CO_2$; solvent B=MeCN/EtOH (1/1). The eluent flow rate is 4.0 mL/min over 5 min. Elution: Isocratic 30% of the solvent B and 70% of the solvent A. Detection: 210 nm.

Non-Chiral Preparative Methods Used:

The purifications by preparative LC-MS are performed using the conditions described hereafter.

L) Preparative LC-MS (I):

A Waters column (Waters XBridge C18, 10 μm OBD, 30×75 mm) is used. The two elution solvents are as follows: solvent A=water+0.5% of a solution of 25% $NH_4OH$ in water; solvent B=acetonitrile. The eluent flow rate is 75 mL/min and the characteristics of the eluting mixture proportion in function of the time t from start of the elution are summarized in the tables below (a linear gradient being used between two consecutive time points):

|  | t (min) | | | | | |
| --- | --- | --- | --- | --- | --- | --- |
|  | 0 | 0.01 | 4.0 | 6.0 | 6.2 | 6.6 |
| Solvent A (%) | 90 | 90 | 5 | 5 | 90 | 90 |
| Solvent B (%) | 10 | 10 | 95 | 95 | 10 | 10 |

Detection 210 nm.

M) Preparative LC-MS (II):

A Waters column (Waters XBridge C18, 10 μm OBD, 30×75 mm) is used. The two elution solvents are as follows: solvent A=water+HCOOH 0.5%; solvent B=acetonitrile. The eluent flow rate is 75 mL/min and the characteristics of the eluting mixture proportion in function of the time t from start of the elution are summarized in the tables below (a linear gradient being used between two consecutive time points):

|  | t (min) | | | | | |
| --- | --- | --- | --- | --- | --- | --- |
|  | 0 | 0.01 | 4.0 | 6.0 | 6.2 | 6.6 |
| Solvent A (%) | 90 | 90 | 5 | 5 | 90 | 90 |
| Solvent B (%) | 10 | 10 | 95 | 95 | 10 | 10 |

Detection 210 nm.

Chiral Preparative HPLC Methods Used:

The separation of epimers are performed by preparative chiral column chromatography using the conditions described hereafter.

N) Chiral Preparative HPLC (I):

ChiralPack OJ-H, 5 μm, 30×250 mm is used, column thermostated at 40° C. The two elution solvents are as follows:

solvent A=$CO_2$; solvent B=MeOH. The eluent flow rate is 160 mL/min. The elution is done using 90% of the solvent A and 10% of the solvent B. The injection V=2.5 mL, 10 mg/mL MeOH.

O) Chiral Preparative HPLC (II):

ChiralPack OJ-H, 5 μm, 30×250 mm is used, column thermostated at 40° C. The two elution solvents are as follows: solvent A=$CO_2$; solvent B=MeOH. The eluent flow rate is 160 mL/min. The elution is done using 85% of the solvent A and 15% of the solvent B. The injection V=1.0 mL, 5 mg/mL MeOH.

P) Chiral Preparative HPLC (III):

ChiralPack IC, 5 μm, 30×250 mm is used, column thermostated at 40° C. The two elution solvents are as follows: solvent A=$CO_2$; solvent B=EtOH. The eluent flow rate is 160 mL/min. The elution is done using 65% of the solvent A and 35% of the solvent B. The injection V=1.0 mL, 10 mg/mL EtOH.

Q) Chiral Preparative HPLC (IV):

ChiralCel OJ-H, 5 μm, 30×250 mm is used, column thermostated at 40° C. The two elution solvents are as follows: solvent A=$CO_2$; solvent B=MeOH. The eluent flow rate is 160 mL/min. The elution is done using 85% of the solvent A and 15% of the solvent B. The injection V=3.5 mL.

R) Chiral Preparative HPLC (V):

Chiralpak IH, 5 μm, 30×250 mm is used, column thermostated at 40° C. The two elution solvents are as follows: solvent A=$CO_2$; solvent B=MeCN/EtOH (1/1). The eluent flow rate is 160 mL/min. The elution is done using 80% of the solvent A and 20% of the solvent B. The injection V=2.0 mL, 8 mg/mL, MeCN/EtOH=1/1.

S) Chiral Preparative HPLC (VI):

ChiralCel OJ-H, 5 μm, 30×250 mm is used, column thermostated at 40° C. The two elution solvents are as follows: solvent A=$CO_2$; solvent B=MeCN/EtOH (1/1). The eluent flow rate is 160 mL/min. The elution is done using 70% of the solvent A and 30% of the solvent B. The injection V=3.5 mL.

Preparation of the Intermediates

Following Intermediates are prepared for the synthesis of the compounds.

Intermediate 1

(3R,4S,5R,6R)-6-(Acetoxymethyl)-4-azidotetrahydro-2H-pyran-2,3,5-triyl triacetate (3R,4S,5R,6R)-6-(acetoxymethyl)-4-azidotetrahydro-2H-pyran-2,3,5-triyl triacetate is synthesized from (3aR,5S,6S,6aR)-5-((R)-2,2-dimethyl-1,3-dioxolan-4-yl)-2,2-dimethyltetrahydrofuro[2,3-d][1,3]dioxol-6-ol following the literature procedures from Ref: *Carbohydrate Research* 1994, 251, 33-67 and references cited therein.

Intermediate 2

(2R,3R,4S,5R,6R)-2-(Acetoxymethyl)-4-azido-6-brom ° tetra hydro-2H-pyran-3,5-diyl diacetate(3R,4S,5R,6R)-6-(acetoxymethyl)-4-azidotetrahydro-2H-pyran-2,3,5-triyl triacetate To a solution of Intermediate 1 (8.0 g, 21.4 mmol) in DCM (250.0 mL) and EA (25.0 mL) is added titanium(IV) bromide (2.4 g, 64.3 mmol, 3.0 eq). The reaction mixture is stirred at rt for 48 h, quenched with NaOAc (25.0 g, 30.4 mmol, 1.4 eq) and stirred at rt for 1 h. The mixture is partitioned between $H_2O$ and DCM, the layers are separated and the aq. layer is extracted with DCM (3×). The combined organic layer is dried over $Na_2SO_4$, filtered and solvent removed in vacuo to give a pale yellow oil. The crude material is purified by Flash Master (Buchi, 120 g column, product added dry on isolute, Hept/EA 100/0 to 8/2, Rf(Hept/EA 8/2)=0.57, not UV-active, stained with $KMnO_4$) to yield the title compound as a colorless oil (11.4 g, 92%). LC-MS (A) $t_R$=0.91 min; [M+H]$^+$: 394.00. $^1$H NMR (400 MHz, CDCl3) δ: 6.73 (d, J=3.7 Hz, 1H), 5.52 (d, J=2.9 Hz, 1H), 4.97 (dd, $J_1$=3.7 Hz, $J_2$=10.5 Hz, 1H), 4.44 (t, J=6.4 Hz, 1H), 4.21 (dd, $J_1$=6.0 Hz, $J_2$=11.5 Hz, 1H), 4.18 (dd, $J_1$=3.3 Hz, $J_2$=10.5 Hz, 1H), 4.07 (dd, $J_1$=7.0 Hz, $J_2$=11.5 Hz, 1H), 2.20 (s, 3H), 2.19 (s, 3H), 2.10 (s, 3H).

Intermediate 3

(2R,3R,4S,5R,6R)-2-(Acetoxymethyl)-6-bromo-4-(4-(3,4,5-trifluorophenyl)-1H-1,3-triazol-1-yl)tetrahydro-2H-pyran-3,5-diyl diacetate To a solution of Intermediate 2 (11.4 g, 28.3 mmol) in DMF (306.0 mL) are added 3,4,5-trifluorophenylacetylene (4.55 g, 28.3 mmol, 1.0 eq), CuI (1.6 g, 8.48 mmol, 0.3 eq) and DIPEA (14.5 mL, 84.8 mmol, 3.0 eq). The reaction mixture is stirred at 44° C. for 17 h. The mixture is cooled to rt, diluted with EA and filtered. The org. layer is washed with aq. sat. $NH_4Cl$ (2×20 mL), brine, dried over $Na_2SO_4$, filtered and solvent concentrated under reduced pressure to afford a beige solid. The crude material is purified by Flash Master (ISCO, product added on isolute on the column, 220 g column, Hept/EA 85/15 to 50/50, EA in Hept (15→50% EA), Rf(Hept/EA 1/1)=0.52, UV-active and stained with $KMnO_4$) to recover Intermediate 3 as a white powder (11.1 g, 72%). LC-MS (A) $t_R$=1.04 min; [M+H]$^+$: 552. $^1$H NMR (400 MHz, CDCl3) δ: 7.82 (s, 1H), 7.46 (dd, $J_1$=6.5 Hz, $J_2$=8.1 Hz, 2H), 6.91 (d, J=3.8 Hz, 1H), 5.84 (dd, $J_1$=3.8 Hz, $J_2$=11.3 Hz, 1H), 5.64 (d, J=1.7 Hz, 1H), 5.34 (dd, $J_1$=3.0 Hz, $J_2$=11.4 Hz, 1H), 4.66 (t, J=6.4 Hz, 1H), 4.26 (dd, $J_1$=6.3 Hz, $J_2$=11.5 Hz, 1H), 4.16 (dd, $J_1$=6.5 Hz, $J_2$=11.5 Hz, 1H), 2.09 (s, 6H), 1.98 (s, 3H).

Intermediate 4

1-((3R,4S,5R,6R)-2-Bromo-3,5-bis((4-chlorobenzyl)oxy)-6-(((4-chlorobenzyl)oxy)methyl)tetrahydro-2H-pyran-4-yl)-4-(3,4,5-trifluorophenyl)-1H-1,2,3-triazole

1. (2R,3R,4S,5R,6S)-2-(Acetoxymethyl)-4-azido-6-(methylthio)tetrahydro-2H-pyran-3,5-diyl diacetate TMS-SMe (2.2 mL, 15.3 mmol, 2.85 eq) and molecular sieves (4 Å, 4.0 g). are added to a solution of Intermediate 1 (2.0 g, 5.4 mmol) in DCM (26.0 mL) at rt. TMS-OTf (0.9 mL, 4.9 mmol, 0.9 eq) is added and the solution stirred at rt for 17 h. The reaction mixture is quenched with aq. 5% $Na_2CO_3$ sol. (10.0 mL) and stirred for 2 h at rt before DCM (10.0 mL) and some water are added. The phases are separated, the aq. phase is extracted with DCM (1×10.0 mL). The combined organic layer is dried over $Na_2SO_4$, filtered and concentrated in vacuo to recover the crude, that is purified by column chromatography on silica gel (18×2.5 cm, product added on isolute, 13 mL fractions, Hept/EA 99/1 to 3/7, Rf(Hept/EA 1/1)=0.62) to afford the title compound (1.7 g, 89%) as white crystals; LC-MS: $t_R$=0.86 min, [M+1$^+$=no mass; $^1$H NMR (400 MHz, CDCl3) δ: 5.48 (d, J=3.3 Hz, 1H), 5.24 (t, J=10.0 Hz, 1H), 4.38 (d, J=9.8 Hz, 1H), 4.1-4.17 (m, 2H), 3.94 (td, $J_1$=6.5 Hz, $J_2$=1.1 Hz, 1H), 3.69 (dd, $J_1$=10.1 Hz, $J_2$=3.3 Hz, 1H), 2.21 (s, 3H), 2.19 (s, 3H), 2.18 (s, 3H), 2.09 (s, 3H).

2. (2R,3R,4S,5R,6S)-2-(Acetoxymethyl)-6-(methylthio)-4-(4-(3,4,5-trifluorophenyl)-1H-1,2,3-triazol-1-yl)tetrahydro-2H-pyran-3,5-diyl diacetate To a solution of (2R,3R,4S,5R,6S)-2-(acetoxymethyl)-4-azido-6-(methylthio)tetrahydro-2H-pyran-3,5-diyl diacetate (7.5 g, 20.7 mmol) in DMF (140.0 mL) are added 3,4,5-trifluorophenylacetylene (5.0 g, 31 mmol, 1.5 eq), CuI (1.18 g, 6.2 mmol, 0.3 eq) and DIPEA (10.6 mL, 62.0 mmol, 3.0 eq). The reaction mixture is stirred at 45° C. over 17 h, then cooled to rt, diluted with EA and filtered. The org. layer is washed with aq. sat. $NH_4Cl$, brine, dried over $Na_2SO_4$, filtered and concentrated under reduced pressure to afford the crude as a beige solid. The crude material is purified by Flash Master (ISCO, 120 g column, Flow 85 mL/min, Hept/EA 40/640 to 0/100, Rf(Hept/EA 1/1)=0.29, UV-active and stained with $KMnO_4$) to recover the desired product as a white powder (9.2 g, 86%). LC-MS: $t_R$=1.0 min, [M+1$^+$= 518.09. $^1$H NMR (400 MHz, CDCl$_3$) δ: 7.81 (s, 1H), 7.44 (m, 2H), 5.77 (dd, $J_1$=9.5 Hz, $J_2$=11.0 Hz), 5.63 (d, J=3.3 Hz), 5.19 (dd, $J_1$=11.1 Hz, $J_2$=3.2 Hz, 1H), 4.59 (d, J=9.5 Hz, 1H), 4.18 (m, 3H), 2.29 (s, 3H), 2.09 (s, 3H), 2.08 (s, 3H), 1.97 (s, 3H).

3. (2R,3R,4S,5R,6S)-2-(Hydroxymethyl)-6-(methylthio)-4-(4-(3,4,5-trifluorophenyl)-1H-1,2,3-triazol-1-yl)tetrahydro-2H-pyran-3,5-diol NaOMe (1.5 g, 27.4 mmol, 1.5 eq) is added at rt to a suspension of (2R,3R,4S,5R,6S)-2-(acetoxymethyl)-6-(methylthio)-4-(4-(3,4,5-trifluorophenyl)-1H-1,2,3-triazol-1-yl)tetrahydro-2H-pyran-3,5-diyl diacetate (9.5 g, 18.3 mmol) in MeOH (400.0 mL) and stirring is continued for 3 h at rt. The mixture is neutralized with aq. 1N HCl and the solvent removed in vacuo. Trituration from TBME yielded (2R,3R,4S,5R,6S)-2-(hydroxymethyl)-6-(methylthio)-4-(4-(3,4,5-trifluorophenyl)-1H-1,2,3-triazol-1-yl)tetrahydro-2H-pyran-3,5-diol as a beige powder (7.22 g, >99%). LC-MS: $t_R$=0.66 min, [M+1$^+$=391.96. $^1$H NMR (400 MHz, CDCl$_3$) δ: 8.8, (s, 1H), 7.84 (m, 2H), 4.81 (dd, $J_1$=3.3 Hz, $J_2$=10.5 Hz, 1H), 4.75 (t, J=11.3 Hz, 1H), 4.46 (d, J=9.3 Hz, 1H), 4.09 (m, 1H), 3.93 (dd, $J_1$=2.5 Hz, $J_2$=6.3 Hz, 1H), 3.723 (t, J=6.3 Hz, 1H), 3.52 (m, 1H), 2.17 (s, 3H).

4. 1-((2R,3R,4S,5R,6S)-3,5-bis((4-Chlorobenzyl)oxy-2-04-chlorobenzyl)oxy)methyl)-6-(methylthio)tetrahydro-2H-pyran-4-yl)-4-(3,4,5-trifluorophenyl)-1H-1,2,3-triazole To a cooled (0° C.) solution of (2R,3R,4S,5R,6S)-2-(hydroxymethyl)-6-(methylthio)-4-(4-(3,4,5-trifluorophenyl)-1H-1,2,3-triazol-1-yl)tetrahydro-2H-pyran-3,5-diol (1.0 g, 2.6 mmol) in DMF (20.0 mL) is added NaH (55% dispersion in oil, 0.39 g, 8.9 mmol, 3.5 eq) and the mixture is stirred at 0° C. for 30 min. 4-Chlorobenzyl bromide (1.9 g, 8.9 mmol, 3.5 eq) is added, the cooling bath removed and the reaction mixture stirred at rt over 17 h. The mixture is diluted with EA and extracted with aq. sat $NH_4Cl$. The org. layer is washed with brine, dried over $MgSO_4$, filtered and concentrated under reduced pressure. The residue is purified by preparative HPLC/MS(I) to recover the title compound as a white powder (1.8 g, 92%). LC-MS: $t_R$=1.3 min, [M+1$^+$ =764.12.

5. 143R,4S,5R,6R)-2-Bromo-3,5-bis((4-chlorobenzyl)oxy)-6-(((4-chlorobenzyl)oxy)methyl)tetrahydro-2H-pyran-4-yl)-4-(3,4,5-trifluorophenyl)-1H-1,2,3-triazole (Intermediate 4)

NBS (0.67 g, 3.76 mmol, 2.0 eq) is added to a solution of 14(2R,3R,4S,5R,6S)-3,5-bis((4-chlorobenzyl)oxy)-2-(((4-chlorobenzyl)oxy)methyl)-6-(methylthio)tetrahydro-2H-pyran-4-yl)-4-(3,4,5-trifluorophenyl)-1H-1,2,3-triazole (2.0 g, 1.88 mmol) in THF (130.0 mL). The reaction mixture is stirred at rt for 4 h, then quenched with water and extracted with EA (2×). The combined org. layer is washed with brine, dried over $Na_2SO_4$, filtered and concentrated under reduced pressure to recover the crude Intermediate 4 as a yellow oil (1.7 g, >99%) that is used without further purification. LC-MS: $t_R$=1.30 min, [M+1]$^+$=797.61.

Intermediate 5

1-((2R,3R,4S,5R)-3,5-bis(Benzyloxy)-2-((benzyloxy)methyl)-6-bromotetrahydro-2H-pyran-4-4-4-(3,4,5-trifluorophenyl)-1H-1,2,3-triazole Intermediate 5 is synthesized from Intermediate 1 and benzyl bromide as the protecting group, according to the procedures described for Intermediate 4. LC-MS: $t_R$=1.26 min, [M+1]$^+$=694.09.

Intermediate 6

N-Isobutyl-2-mercapto-N-methylacetamide

1. S-(2-(Isobutyl(methyl)amino)-2-oxoethyl)ethanethioate

N-Methylisobutylamin (0.28 mL, 2.32 mmol, 1.2 eq), 4-DMAP (0.025 g, 0.2 mmol, 0.1 eq), TEA (1.4 mL, 10 mmol, 5.0 eq) and T3P (50% in DCM, 6.0 mL, 1.5 eq) are added to a cooled (0° C.) solution of 2-(acetylthio)acetic acid (95%, 0.3 g, 2.0 mmol) in DCM (20.0 mL). The reaction mixture is stirred at rt for 30 min, partitioned between aq. 1N NaOH and EA and the layers are separated. The aqueous layer is extracted with EA, the combined organic layer is dried over Na$_2$SO$_4$, filtered and solvent removed in vacuo. The residue is purified by preparative HPLC/MS (I). S-(2-(isobutyl(methyl)amino)-2-oxoethyl) ethanethioate is extracted from the collected fractions with EA, dried over Na$_2$SO$_4$, filtered and solvent concentrated in vacuo to give the title compound (0.40 g, 98%) as a colorless oil. LC-MS (A): $t_R$=0.71 min; [M+H]$^+$: 204.09. $^1$H NMR (400 MHz, CDCl$_3$) δ: 8.05 (s, 1H), 3.87 (d, J=5.5 Hz, 2H), 3.22 (dd, J$_1$=7.5 Hz, J$_2$=16.5 Hz, 2H), 3.09 (s, 1.5 H), 2.97 (s, 1.5 H), 2.40 (d, J=2.8 Hz, 2H), 1.94-2.07 (m, 1H), 0.98 (d, J=6.8 Hz, 3H), 0.91 (d, J=6.8 Hz 3H).

2. N-isobutyl-2-mercapto-N-methylacetamide (Intermediate 6)

Aq. 1N NaOH (1.48 mL, 1.5 eq) is added to a cooled (0° C.) solution of S-(2-(isobutyl(methyl)amino)-2-oxoethyl) ethanethioate (0.20 g, 1.0 mmol, 1.0 eq) in MeOH (8.0 mL). The reaction mixture is stirred at rt for 10 min, then quenched with aq. 1N HCl, and the solvent is removed in vacuo. The residue is extracted with EA, the phases are separated and the organic phase dried over Na$_2$SO$_4$, filtered and solvent removed in vacuo to recover the crude N-isobutyl-2-mercapto-N-methylacetamide as a colorless oil (0.10 g, 63%), that is used without further purification. LC-MS (A): $t_R$=0.66 min; [M+H]$^+$: 162.2.

Intermediate 7

Intermediate 7 is prepared by using adapted procedures from the literature (Ref: *Chem Lett* 1977, 471-474 and references cited therein).

tert-Butyl 3-hydroxy-2-mercapto-3-methylbutanoate (Intermediate 7)

To a cooled (–78° C.) solution of tert-butyl 2-sulfanylacetate (1.5 g, 10.0 mmol) and TMEDA (3.4 mL, 22.3 mmol, 2.2 eq) in THF (50.0 mL), is added dropwise LDA (2.0 M in THF/Hept/ethylbenzene, 11.2 mL, 2.2 eq). The solution is stirred at –78° C. for 30 min, acetone (0.9 mL, 12.1 mmol, 1.2 eq) is then added and stirring continued at –78° C. for 30 min. The reaction mixture is quenched with aq. sat. NH$_4$Cl at –78° C., warmed to rt, and diluted with EA. The 2 phases are separated, the organic phase is dried over Na$_2$SO$_4$, filtered and solvent concentrated in vacuo to recover the crude tert-butyl 3-hydroxy-2-mercapto-3-methylbutanoate as a yellow oil (2.5 g, >99%), that is used without further purification. LC-MS (A): $t_R$=0.78 min; [M+H]$^+$: 207.09.

Intermediate 8 tert-Butyl 2-(4-hydroxy-1-methylpiperidin-4-yl)-2-mercaptoacetate (Intermediate 8)

Intermediate 8 is synthesized from tert-butyl 2-sulfanylacetate and 1-methylpiperidin-4-one according to the procedures described for the synthesis of Intermediate 7. LC-MS(A) $t_R$=0.52 min, [M+1]$^+$=262.10.

Intermediate 9 tert-Butyl 2-(4-hydroxytetrahydro-2H-pyran-4-4-2-mercaptoacetate (Intermediate 9)

Intermediate 9 is synthesized from tert-butyl 2-sulfanylacetate and tetrahydro-4H-pyran-4-one according to the procedure described for the synthesis of Intermediate 7. LC-MS(A) $t_R$=0.75 min, [M+1]$^+$=249.03.

Intermediate 10

(2R,3R,4S,5R,6S)-2-(Acetoxymethyl)-6-((2-(ethyl(methyl)amino)-1-(4-hydroxypiperidin-4-yl)-2-oxoethyl)thio)-4-(4-(3,4,5-trifluorophenyl)-1H-1,2,3-triazol-1-yl)tetrahydro-2H-pyran-3,5-diyl diacetate 1. 1,1,1-Trichloro-2-methylpropan-2-yl 4-oxopiperidine-1-carboxylate Piperidin-4-one hydrochloride (0.50 g, 3.5 mmol) is dissolved in DCM (25.0 mL), added are 2,2,2-trichloro-1,1-dimethylethyl chloroformate (0.87 g, 3.5 mmol, 1.0 eq) followed by DIPEA (1.8 mL, 10.5 mmol, 3.0 eq) and the reaction mixture is stirred at rt for 17 h. DIPEA (1.0 mL, 5.8 mmol) is added again and the reaction mixture stirred for 5 h, then partitioned between DCM and water. The layers are separated and the aqueous layer is extracted with DCM (3×). The combined organic layer is dried over MgSO$_4$, filtered and the solvent removed in vacuo to give an orange oil that is purified by preparative HPLC/MS (I) to recover 1,1,1-trichloro-2-methylpropan-2-yl 4-oxopiperidine-1-carboxylate as a white powder (0.434 g, 41%). LC-MS (A): $t_R$=0.91 min; [M+H]$^+$: 301.87.

2. 1,1,1-Trichloro-2-methylpropan-2-yl 4-(2-(tert-butoxy)-1-mercapto-2-oxoethyl)-4-hydroxypiperidine-1-carboxylate To a cooled (–78° C.) solution of tert-butyl 2-sulfanylacetate (0.12 g, 0.81 mmol) and TMEDA (0.27 mL, 0.81 mmol, 2.2 eq) in THF (10.0 mL), is added dropwise an LDA solution (1.0 M THF/heptane/ethylbenzene, 1.78 mL, 2.2 eq). The solution is stirred at –78° C. for 10 min. 1,1,1-Trichloro-2-methylpropan-2-yl 4-oxopiperidine-1-carboxylate (0.27 g, 1.38 mmol, 1.2 eq) is added at –78° C. After 15 min the reaction mixture is quenched with aq. sat. NH$_4$Cl at –78° C., then it is allowed to warm to t, diluted with EA and the phases are separated. The organic phase is dried over Na₂SO₄, filtered and solvent removed in vacuo to recover the crude as a brown oil (0.456 g, >99%), that is not further purified. LC-MS (A): $t_R$=1.11 min; [M+H]⁺: 449.84.

3. (2R,3R,4S,5R,6S)-2-(Acetoxymethyl)-6-((2-(tert-butoxy)-1-(4-hydroxy-1-(((1,1,1-trichloro-2-methyl-propan-2-yl)oxy)carbonyl)piperidin-4-yl)-2-oxo-ethyl)thio)-4-(4-(3,4,5-trifluorophenyl)-1H-1,2,3-triazol-1-yl)tetrahydro-2H-pyran-3,5-diyl diacetate To a solution of Intermediate 3 (1.3 g, 0.50 mmol) and 1,1,1-trichloro-2-methylpropan-2-yl 4-(2-(tert-butoxy)-1-mercapto-2-oxoethyl)-4-hydroxypiperidine-1-carboxylate (0.152 g, 0.50 mmol, 1.0 eq) in EA (12.5 mL) is added TBAB (0.04 g, 0.25 eq). Aq. 1M Na₂CO₃ (6.0 mL) is then added until the reaction mixture has become a clear solution that is stirred at rt for 17 h. The reaction mixture is diluted with EA (10.0 mL) followed by water (10.0 mL) and brine (10.0 mL). The phases are separated and the aq. layer is extracted with EA (30.0 mL). The combined organic phase is dried over Na₂SO₄, filtered and solvent removed in vacuo. The residue is purified by preparative HPLC/M S (I) to recover the title compound (0.23 g, 54%) as a beige solid. LC-MS (A): $t_R$=1.20 min; [M+H]⁺: 919.23.

4. 2-(((2S,3R,4S,5R,6R)-3,5-Diacetoxy-6-(acetoxymethyl)-4-(4-(3,4,5-trifluorophenyl)-1H-1,2,3-triazol-1-yl)tetrahydro-2H-pyran-2-yl)thio)-2-(4-hydroxy-1-(((1,1,1-trichloro-2-methylpropan-2-yl)oxy)carbonyl)piperidin-4-yl)acetic acid To a solution of (2R,3R,4S,5R,6S)-2-(acetoxymethyl)-6-(((2-(tert-butoxy)-1-(4-hydroxy-1-(((1,1,1-trichloro-2-methylpropan-2-yl)oxy)carbonyl)piperidin-4-yl)-2-oxoethypthio)-4-(4-(3,4,5-trifluorophenyl)-1H-1,2,3-triazol-1-yl)tetrahydro-2H-pyran-3,5-diyl diacetate (2.32 g, 2.52 mmol) in DCM (13.0 mL) is added TFA (3.25 mL, 42.4 mmol, 17.0 eq) at rt. The reaction mixture is stirred at rt. After 2 h TFA (0.33 mL, 4.24 mmol, 1.7 eq) is added and the mixture is stirred for 72 h. The mixture is carefully neutralized with aq. 1M NaOH, diluted with DCM and the layers are separated. The aqueous layer is extracted with DCM (3×), the combined organic layer is dried over Na₂SO₄, filtered and solvent removed in vacuo to recover the title compound (2.25 g, >99%) as a beige powder, that is not further purified. LC-MS (A): $t_R$=1.07 min; [M+H]⁺: 862.82.

5. (2R,3R,4S,5R,6S)-2-(Acetoxymethyl)-6-((2-(ethyl(methyl)amino)-1-(4-hydroxy-1-(((1,1,1-trichloro-2-methylpropan-2-yl)oxy)carbonyl)piperidin-4-yl)-2-oxoethyl)thio)-4-(4-(3,4,5-trifluorophenyl)-1H-1,2,3-triazol-1-yl)tetrahydro-2H-pyran-3,5-diyl diacetate To a cooled (0° C.) solution of 2-(((2S,3R,4S,5R,6R)-3,5-diacetoxy-6-(acetoxymethyl)-4-(4-(3,4,5-trifluorophenyl)-1H-1,2,3-triazol-1-yl)tetrahydro-2H-pyran-2-yl)thio)-2-(4-hydroxy-1-(((1,1,1-trichloro-2-methylpropan-2-yl)oxy)carbonyl)piperidin-4-yl)acetic acid (1.0 g, 1.16 mmol) in DMF (20.0 mL) are added N-ethyl methyl amine (0.2 mL, 2.31 mmol, 2.0 eq), and HATU (0.48 g, 1.22 mmol, 1.05 eq). The reaction mixture is stirred at rt for 2 h, 4 drops of DIPEA are added and stirring is continued for 35 min. The reaction mixture is partitioned between aq. 1N NaOH and DCM, the layers are separated and the aqueous layer is extracted with DCM. The combined organic layer is dried over Na₂SO₄, filtered and solvent removed in vacuo. The residue is purified by preparative HPLC/MS (II) to recover the title compound as a colorless oil (0.60 g, 57%). LC-MS (A): $t_R$=1.16 min; [M+H]⁺: 904.12.

6. (2R,3R,4S,5R,6S)-2-(Acetoxymethyl)-6-((2-(ethyl(methyl)amino)-1-(4-hydroxypiperidin-4-yl)-2-oxoethyl)thio)-4-(4-(3,4,5-trifluorophenyl)-1H-1,2,3-triazol-1-yl)tetra hydro-2H-pyran-3,5-diyl diacetate To a solution of (2R,3R,4S,5R,6S)-2-(acetoxymethyl)-6-((2-(ethyl(methyl)amino)-1-(4-hydroxy-1-(((1,1,1-trichloro-2-methylpropan-2-yl)oxy)carbonyl)piperidin-4-yl)-2-oxoethypthio)-4-(4-(3,4,5-trifluorophenyl)-1H-1,2,3-triazol-1-yl)tetrahydro-2H-pyran-3,5-diyl diacetate (0.56 g, 0.6 mmol) in THF (45.0 mL) and glacial acetic acid (0.84 mL) is added zinc powder (0.40 g, 6.15 mmol, 10.0 eq). The reaction mixture is stirred at rt for 1.5 h, filtered, diluted with EA followed by water and the layers are separated. The aqueous layer is extracted with EA, the combined organic layer is washed with brine, dried over Na₂SO₄, filtered and solvent removed in vacuo to recover a beige solid. The crude is purified by preparative HPLC/MS (I) to afford the title compound as a beige powder (0.32 g, 74%). LC-MS (A): $t_R$=0.78 min; [M+H]⁺: 702.19.

Intermediate 10I ((2R,3R,4S,5R,6S)-3-Acetoxy-6-((2-(ethyl(methyl)amino)-1-(4-hydroxypiperidin-4-4-2-oxoethyl)thio)-5-methoxy-4-(4-(3,4,5-trifluorophenyl)-1H-1,2,3-triazol-1-yl)tetrahydro-2H-pyran-2-yl)methyl acetate The title compound is prepared in analogy to Intermediate 10, in Step 3. Intermediate 14 is used. Intermediate 10I is obtained as a solid (0.317 g). LC-MS(A) $t_R$=0.80 min, [M+H]⁺=736.47.

Intermediate 10AR (2R,3R,4S,5R,6S)-2-(Acetoxymethyl)-6-(((R)-2-(ethyl(methyl)amino)-1-(3-hydroxyazetidin-3-yl)-2-oxoethyl)thio)-4-(4-(3,4,5-trifluorophenyl)-1H-1,2,3-triazol-1-yl)tetrahydro-2H-pyran-3,5-diyl diacetate 1. 1,1,1-Trichloro-2-methylpropan-2-yl 3-(2-(ethyl(methyl)amino)-1-mercapto-2-oxoethyl)-3-hydroxyazetidine-1-carboxylate The title compound is prepared from N-ethyl-N-methyl-2-((tetrahydro-2H-pyran-2-yl)thio)acetamide and 1,1,1-trichloro-2-methylpropan-2-yl 3-oxoazetidine-1-carboxylate in analogy to Intermediate 12 as a beige solid (0.11 g). LC-MS(A) $t_R$=0.93 min, [M+H]⁺=405.05.

2. (2R,3R,4S,5R,6S)-2-(Acetoxymethyl)-6-(((R)-2-(ethyl(methyl)amino)-1-(3-hydroxy-1-(((1,1,1-trichloro-2-methylpropan-2-yl)oxy)carbonyl)azetidin-3-yl)-2-oxoethyl)thio)-4-(4-(3,4,5-trifluorophenyl)-1H-1,2,3-triazol-1-yl)tetrahydro-2H-pyran-3,5-diyl diacetate The title compound is prepared from 1,1,1-trichloro-2-methylpropan-2-yl 3-(2-(ethyl(methyl)amino)-1-mercapto-2-oxoethyl)-3-hydroxyazetidine-1-carboxylate and Intermediate 3 in analogy to Intermediate 10 Step. 3. Purification of the crude by preparative HPLC/MS(I) yielded the isolation of the R-epimer as a beige solid (0.027 g). LC-MS(A) $t_R$=1.09 min, [M+H]$^+$=878.23.

3. (2R,3R,4S,5R,6S)-2-(acetoxymethyl)-6-(((R)-2-(ethyl(methyl)amino)-1-(3-hydroxyazetidin-3-yl)-2-oxoethyl)thio)-4-(4-(3,4,5-trifluorophenyl)-1H-1,2,3-triazol-1-yl)tetrahydro-2H-pyran-3,5-diyl diacetate (Intermediate 10AR)

To a solution of (2R,3R,4S,5R,6S)-2-(acetoxymethyl)-6-(((R)-2-(ethyl(methyl)amino)-1-(3-hydroxy-1-(((1,1,1-trichloro-2-methyl propan-2-yl)oxy)carbonyl)azetidin-3-yl)-2-oxoethyl)thio)-4-(4-(3,4,5-trifluorophenyl)-1H-1,2,3-triazol-1-yl)tetrahydro-2H-pyran-3,5-diyl diacetate (0.26 g, 0.03 mmol) in THF (1.7 mL) and AcOH (0.0042 mL) is added zinc powder (0.019 g, 10.0 eq). The reaction mixture is stirred at rt over 15 h, filtered and partitioned between EA and water. The layers are separated, the aqueous layer is extracted with EA, the combined organic layer is washed with brine, dried over Na$_2$SO$_4$, filtered and solvent removed in vacuo to recover the title compound as a pale yellow solid (0.025 g) as the crude and is not further purified. LC-MS(A) $t_R$=0.77 min, [M+H]$^+$=674.21.

Intermediate 10AS (2R,3R,4S,5R,6S)-2-(Acetoxymethyl)-6-(((S)-2-(ethyl(methyl)amino)-1-(3-hydroxyazetidin-3-yl)-2-oxoethyl)thio)-4-(4-(3,4,5-trifluorophenyl)-1H-1,2,3-triazol-1-yl)tetrahydro-2H-pyran-3,5-diyl diacetate Intermediate 10AS is obtained as described for Intermediate 10AR. The S epimer is as well separated and isolated during the preparative HPLC/MS(I) purification of Step 2. of Intermediate 10AR.

1. (2R,3R,4S,5R,6S)-2-(Acetoxymethyl)-6-(((S)-2-(ethyl(methyl)amino)-1-(3-hydroxy-1-(((1,1,1-trichloro-2-methylpropan-2-yl)oxy)carbonyl)azetidin-3-yl)-2-oxoethyl)thio)-4-(4-(3,4,5-trifluorophenyl)-1H-1,2,3-triazol-1-yl)tetrahydro-2H-pyran-3,5-diyl diacetate The title compound is prepared in analogy to Intermediate 10AR Step 2. as a beige solid (0.026 g). LC-MS(A) $t_R$=1.10 min, [M+H]$^+$=878.23.

2. (2R,3R,4S,5R,6S)-2-(Acetoxymethyl)-6-(((S)-2-(ethyl(methyl)amino)-1-(3-hydroxyazetidin-3-yl)-2-oxoethyl)thio)-4-(4-(3,4,5-trifluorophenyl)-1H-1,2,3-triazol-1-yl)tetrahydro-2H-pyran-3,5-diyl diacetate The title compound is obtained in analogy to Intermediate 10AR as the a beige solid (crude, 0.019 g) and is not further purified. LC-MS(A) $t_R$=0.77 min, [M+H]$^+$=674.12.

Intermediate 11

N-Cyclobutyl-2-(1-hydroxycyclohexyl)-2-mercapto-N-methylacetamide

1. S-(2-(Cyclobutyl(methyl)amino)-2-oxoethyl)ethanethioate

To a solution of 2-(acetylthio)acetic acid 95% (1.0 g, 6.71 mmol) in DMF (8.0 mL) is added HATU (2.8 g, 7.04 mmol, 1.05 eq) and the mixture is cooled to 0° C. Cyclobutyl-methyl-amine (0.65 g, 7.38 mmol, 1.1 eq) and DIPEA (1.29 mL, 7.38 mmol, 1.7 eq) in DMF(2.0 mL) are added and the mixture is stirred at rt for 15 h. The reaction mixture is concentrated to half of its original volume, filtered and purified by prep HPLC(II) to recover the title product (1.05 g, 78%) as a pale yellow oil. LC-MS(A) $t_R$=0.68 min, [M+H]$^+$=202.15.

2. N-Cyclobutyl-2-mercapto-N-methylacetamide

To a solution of S-(2-(cyclobutyl(methyl)amino)-2-oxoethyl)ethanethioate (1.05 g, 5.22 mmol) in MeOH (10.0 mL) is added NH$_4$Cl (0.87 mL) and stirring is continued at rt for 4 h. The reaction mixture is acidified with aq 1N HCl, the solvent removed in vacuo, and extracted with EA (2×). The combined organic layer is dried over Na$_2$SO$_4$, filtered and concentrated in vacuo to recover the title compound as pale purple oil (0.905 g, >99%). LC-MS(A) $t_R$=0.61 min, [M+H]$^+$=160.18.

3. N-cyclobutyl-2-(1-hydroxycyclohexyl)-2-mercapto-N-methylacetamide

A spatula tip of molecular sieves(4 Å) is added to a solution of N-cyclobutyl-2-mercapto-N-methylacetamide (0.831 g, 5.22 mmol) in THF (25.0 mL). The solution is cooled to −78° C. and TMEDA (1.74 mL, 11.5 mmol, 2.2 eq) is added followed by dropwise addition of LDA (1.0 M in THF/heptane/ethylbenzene, 11.5 mL, 2.2 eq). The solution is stirred at −78° C. for 20 min, then cyclohexanone (0.65 mL, 1.2 eq) is added and after 30 min the reaction mixture is quenched with aq. sat. NH$_4$Cl at −78° C. The mixture is allowed to warm to rt and EA is added. The 2 phases are separated and the organic phase is dried over Na$_2$SO$_4$, filtered and concentrated in vacuo. Purification of the crude by prep HPLC(II) yielded the desired product as a colorless oil (0.420 g, 31%). LC-MS(A) $t_R$=0.89 min, [M+H]$^+$=257.93.

Intermediate 12

N-Ethyl-2-(4-hydroxytetrahydro-2H-pyran-4-0)-2-mercapto-N-methylacetamide

1. Ethyl 2-((tetrahydro-2H-pyran-2-yl)thio)acetate 3,4-Dihydro-2H-pyran (1.1 mL, 11.5 mmol) is slowly added to a cooled (0° C.) mixture of ethyl thioglycolate (1.3 mL, 11.5 mmol, 1.0 eq) in HCl 37% (0.5 mL). The reaction mixture is stirred at 0° C. for 2 h, then quenched with Et$_2$O. The organic layer is washed with aq.10% NaHCO$_3$, dried over Na$_2$SO$_4$, filtered and solvent removed in vacuo to yield the crude. Purification by Flash Master (ISCO, product linked on isolute, 24 g column, Hept/EA 100/0 to 0/100) yielded the title product as a beige oil (1.94 g, 82%). LC-MS (A): $t_R$=0.79 min; [M+H]$^+$: 205.17.

2. 2-((Tetrahydro-2H-pyran-2-yl)thio)acetic acid

To a cooled (0° C.) solution of ethyl 2-((tetrahydro-2H-pyran-2-yl)thio)acetate (1.8 g, 6.8 mmol) in EtOH (40.0 mL) is added aq. 2N NaOH (8.5 mL, 17.0 mmol, 2.5 eq). The reaction mixture is stirred at 0° C. for 30 min, acidified with aq. 2N HCl and concentrated in vacuo, then partitioned between EA and water. The organic layer is washed with water, dried over Na$_2$SO$_4$, filtered and solvent removed in vacuo to give the crude, that is purified by preparative HPLC/MS (II) to give the title compound as a colorless oil (1.01 g, 80%). LC-MS (A): $t_R$=0.54 min; [M+H]$^+$: 177.22.

3. N-Ethyl-N-methyl-2-((tetrahydro-2H-pyran-2-yl)thio)acetamide

To a solution of 2-((tetrahydro-2H-pyran-2-yl)thio)acetic acid (0.50 g, 2.84 mmol, 1.0 eq) in DMF (8.0 mL) is added HATU (1.20 g, 2.98 mmol, 1.05 eq) and the mixture is cooled to 0° C. A solution of N-ethylmethylamine 97% (0.3 mL, 3.4 mmol, 1.2 eq) and DIPEA (0.6 mL, 3.12 mmol, 1.7 eq) in DMF (1.0 mL) are added and the mixture is stirred at rt for 15 h. The reaction mixture is directly purified by preparative HPLC/MS(I) to give the title compound as a beige oil (0.56 g, 92%). LC-MS (A): $t_R$=0.67 min; [M+H]$^+$: 218.24.

4. N-Ethyl-2-(4-hydroxytetrahydro-2H-pyran-4-yl)-N-methyl-2-((tetrahydro-2H-pyran-2-yl)thio)acetamide To a cooled solution (−78° C.) of N-ethyl-N-methyl-2-((tetrahydro-2H-pyran-2-yl)thio)acetamide (0.27 g, 1.24 mmol) in THF (12.0 mL) are added molecular sieves (4 Å) and TMEDA (0.41 mL, 2.73 mmol, 2.2 eq), followed by dropwise addition of an LDA solution (1.0 M in THF/Hept/ethylbenzene, 2.73 mL, 2.73 mmol, 2.2 eq), while keeping the solution below −70° C. The solution is stirred at −78° C. for 20 min, then tetrahydro-4H-pyran-4-one (0.14 mL, 1.49 mmol, 1.2 eq) is added and the stirring is continued at −78° C. for 1 h. The reaction mixture is quenched with aq. sat. NH$_4$Cl at −78° C., warmed to rt, diluted with EA, the phases are separated and the aq. phase is extracted with EA (3×). The combined organic layer is dried over Na$_2$SO$_4$, filtered and solvent removed in vacuo to give an oil, that is purified by preparative HPLC/MS(II) to give the title compound as a yellow oil (0.27 g, 67%). LC-MS (A): $t_R$=0.69 min; [M+H]$^+$: 318.18.

5. N-Ethyl-2-(4-hydroxytetrahydro-2H-pyran-4-yl)-2-mercapto-N-methylacetamide (Intermediate 12)

To a solution of N-ethyl-2-(4-hydroxytetrahydro-2H-pyran-4-yl)-N-methyl-2-((tetrahydro-2H-pyran-2-yl)thio) acetamide (0.27 mg, 0.83 mmol, 1.0 eq) in THF (8.0 mL) are added AgNO$_3$ (0.29 g, 1.69 mmol, 2.0 eq) and water (8.0 mL). The reaction mixture is stirred for 20 min, then diluted with DCM (45.0 mL), NaSH (466.0 mg, 8.32 mmol, 10.0 eq) is added and the mixture is stirred vigorously for 30 min at rt. The resulting black precipitate is removed by filtration and washed (2×) with DCM. The layers of the filtrate are separated, the organic layer is washed with aq. sat. NH$_4$Cl, dried over Na$_2$SO$_4$, filtered and solvent removed in vacuo to give an oil, that is purified by preparative HPLC/MS (II) to give the title product as a yellow solid (0.14 g, 73%). LC-MS (A): $t_R$=0.56 min; [M+H]$^+$: 234.18. $^1$H NMR (400 MHz, CDCl3) δ: 3.82-3.74 (m, 4H), 3.50-3.39 (m, 1.5 H), 3.33-3.18 (m, 1.5 H), 3.05 (s, 1.5 H), 2.93 (s, 1.5 H), 2.38-2.17 (m, 1H), 2.13-2.02 (bd, J=13.5 Hz, 1H), 1.70-1.46 (m, 2H), 1.42-1.32 (m, 1H), 1.26-1.19 (bt, J=6.5 Hz, 1.5 H), 1.17-1.1 (bt, J=7.0 Hz, 1.5 H).

Intermediate 13

(2R,3R,4S,5R,6S)-2-(Acetoxymethyl)-4-azido-6-((2-(ethyl(methyl)amino)-1-(4-hydroxytetrahydro-2H-pyran-4-yl)-2-oxoethyl)thio)tetrahydro-2H-pyran-3,5-diyl diacetate (Intermediate 13)

To a solution of Intermediate 12 (0.14 g, 0.61 mmol, 1.0 eq) in aq. 10% Na$_2$CO$_3$ (6.0 mL) is added TBAHS (1.30 g, 3.65 mmol, 6.0 eq). To this mixture is added Intermediate 2 (0.29 g, 1.03 mmol, 1.2 eq) in EA (12.0 mL) and the mixture is stirred at rt for 48 h, diluted with EA, water and brine. The phases are separated and the aq. layer is extracted with EA (3×). The combined organic phase is dried over Na$_2$SO$_4$, filtered and solvent removed in vacuo. The resulting crude is purified by preparative HPLC/MS (I) to give the title compound as a beige powder (0.20 g, 61%). LC-MS (A): $t_R$=0.81 min; [M+H]$^+$: 547.2

Intermediate 14

((2R,3R,4S,5R,6R)-3-Acetoxy-6-bromo-5-methoxy-4-(4-(3,4,5-trifluorophenyl)-1H-1,2,3-triazol-1-yl)tetrahydro-2H-pyran-2-yl)methyl acetate Intermediate 14 is prepared from (2R,3R,4S,5R,6S)-2-(hydroxymethyl)-6-(methylthio)-4-(4-(3,4,5-trifluorophenyl)-1H-1,2,3-triazol-1-yl)tetrahydro-2H-pyran-3,5-diol Intermediate 4 Step 3.

1. (4aR,6S,7R,8R,8aR)-2,2-Dimethyl-6-(methylthio)-8-(4-(3,4,5-trifluorophenyl)-1H-1,2,3-triazol-1-yl)hexahydropyrano[3,2-d][1,3]dioxin-7-ol 2,2-Dimethoxypropane (14.1 mL, 115.0 mmol, 3.0 eq), and CSA (4.38 g, 18.9 mmol, 0.5 eq) are added to a solution of Intermediate 4 Step3. (14.76 g, 37.7 mmol), in DMF (200.0 mL). The reaction mixture is heated at 50° C. for 1 h, cooled to rt and quenched with EA and brine. The phases are separated and the aq. layer is extracted with EA (3×). The combined organic layer is dried over Na$_2$SO$_4$, filtered and solvent removed in vacuo to give the crude, that is purified by Flash Master (ISCO, product added on isolute, 120 g column, Hept/EA 95/5 to 55/45) The title compound is obtained as a beige solid (9.85 g, 61%). LC-MS (A): $t_R$=0.91 min; [M+H]$^+$: 432.14

2. 1-((4aR,6S,7R,8S,8aR)-7-Methoxy-2,2-dimethyl-6-(methylthio)hexahydropyrano[3,2-d][1,3]dioxin-8-yl)-4-(3,4,5-trifluorophenyl)-1H-1,2,3-triazole To a solution of (4aR,6S,7R,8R,8aR)-2,2-dimethyl-6-(methylthio)-8-(4-(3,4,5-trifluorophenyl)-1H-1,2,3-triazol-1-yl)hexahydropyrano[3,2-d][1,3]dioxin-7-ol (9.85 g, 22.8 mmol) in DMF (200.0 mL) are added molecular sieves (4 Å), followed by Ag$_2$O (26.46 g, 114.00 mmol, 5.0 eq). The reaction mixture is stirred for 15 min at rt, then MeI (7.34 mL, 114.0 mmol, 5.0 eq) is added and stirring at rt is continued for 15 h. The mixture is filtered, diluted with EA, followed by water, the phases are separated and the aqueous layer is extracted with EA (2×). The combined organic layer is dried over Na$_2$SO$_4$, filtered and solvent removed in vacuo to give a beige solid, that is purified by Flash Master (ISCO, product added on isolute, 120 g column, Hept/EA 90/10 to 30/70 Rf(Hept/EA 1/1)=0.52, UV-active). The title compound is obtained as a white powder (6.18 g, 61%). LC-MS (A): $t_R$=0.99 min; [M+H]$^+$: 446.21.

3. (2R,3R,4S,5R,6S)-2-(Hydroxymethyl)-5-methoxy-6-(methylthio)-4-(4-(3,4,5-trifluorophenyl)-1H-1,2,3-triazol-1-yl)tetrahydro-2H-pyran-3-ol To a solution of 1-((4aR,6S,7R,8S,8aR)-7-methoxy-2,2-dimethyl-6-(methylthio)hexahydropyrano[3,2-d][1,3]dioxin-8-yl)-4-(3,4,5-trifluorophenyl)-1H-1,2,3-triazole (6.18 g, 13.9 mmol) in THF (200.0 mL) is added a mixture of (AcOH/water 1/1, 600.0 mL) and the solution is stirred at 65° C. for 15 h. The reaction mixture is diluted with EA, followed by aq. sat. NaHCO$_3$. The layers are separated, the aq. layer is extracted with EA (2×). The combined organic layer is dried over Na$_2$SO$_4$, filtered and solvent removed in vacuo to recover the title compound as a beige solid (29.00 g, >99%), that is used without further purification. LC-MS (A): t$_R$=0.80 min; [M+H]$^+$: 405.96.

4. ((2R,3R,4S,5R,6S)-3-Acetoxy-5-methoxy-6-(methylthio)-4-(4-(3,4,5-trifluorophenyl)-1H-1,2,3-triazol-1-yl)tetrahydro-2H-pyran-2-yl)methyl acetate To a cooled (0° C.) solution of (2R,3R,4S,5R,6S)-2-(hydroxymethyl)-5-methoxy-6-(methylthio)-4-(4-(3,4,5-trifluorophenyl)-1H-1,2,3-triazol-1-yl)tetrahydro-2H-pyran-3-ol (5.64 g, 13.9 mmol) in pyridine (99.0 mL) is added Ac$_2$O (8.0 mL, 83.4 mmol, 6.0 eq). The reaction mixture is stirred at rt for 2 h, then concentrated under reduced pressure. The resulting residue is partitioned between EA and water, the phases are separated and the organic layer is washed with water, dried over Na$_2$SO$_4$, filtered and solvent removed in vacuo to give a beige solid. Purification by Flash master (ISCO, product added on isolute, 120 g column, Hept/EA 95/5 to 30/70) yielded the title compound as a white solid (5.66 g, 83%). LC-MS (A): t$_R$=1.00 min; [M+H]$^+$: 490.07.

5. ((2R,3R,4S,5R,6RS)-3-Acetoxy-6-bromo-5-methoxy-4-(4-(3,4,5-trifluorophenyl)-1H-1,2,3-triazol-1-yl)tetrahydro-2H-pyran-2-yl)methyl acetate (Intermediate 14)

NBS (4.00 g, 22.4 mmol, 2.0 eq) is added to a solution of ((2R,3R,4S,5R,6S)-3-acetoxy-5-methoxy-6-(methylthio)-4-(4-(3,4,5-trifluorophenyl)-1H-1,2,3-triazol-1-yl)tetrahydro-2H-pyran-2-yl)methyl acetate (5.66 g, 11.2 mmol) in DCM (165.0 mL). The reaction mixture is stirred at rt for 15 h, quenched with water and diluted with DCM. The layers are separated and the aq. layer is extracted with DCM (2×). The combined organic layer is washed with brine, dried over Na$_2$SO$_4$, filtered and solvent removed in vacuo to give the crude. Purification by Flash Master (ISCO, product added on isolute, 80 g column, Hept/EA 100/0 to 30/70) yielded the title compound as a beige solid (1.72 g, 29%). LC-MS (A): t$_R$=1.01 min; [M+H]$^+$: 524.02. $^1$H NMR (500 MHz, CDCl$_3$) δ: 7.82 (s, 1H), 7.45 (dd, J$_1$=7.3 Hz, J$_2$=7.3 Hz, 2H), 6.87 (d, J=3.6 Hz, 1H), 5.60 (d, J=2.3 Hz, 1H), 5.01 (dd, J$_1$=10.7 Hz, J$_2$=2.9 Hz, 1H), 4.63 (t, J=6.6 Hz, 1H), 4.48 (dd, J$_1$=10.7 Hz, J$_2$=3.6 Hz, 1H), 4.24 (dd, J$_1$=11.3 Hz, J$_2$=6.4 Hz, 1H), 4.18 (dd, J$_1$=11.3 Hz, J$_2$=6.4 Hz, 1H), 3.39 (s, 3H), 2.10 (s, 3H), 2.08 (s, 3H).

Intermediate 15

((2R,3R,4S,5R,6R)-3-Acetoxy-6-bromo-5-ethoxy-4-(4-(3,4,5-trifluorophenyl)-1H-1,2,3-triazol-1-yl)tetrahydro-2H-pyran-2-yl)methyl acetate Intermediate 15 is prepared from Intermediate 1 according to the procedures described for Intermediate 14. In Step 5. EtI is added to the reaction mixture. Intermediate 15 is obtained as a white powder. LC-MS (A): t$_R$=1.03 min; [M+H]$^+$: 538.15.

PREPARATION OF THE REFERENCE EXAMPLES

Reference Example 1

Example 2.53.203

2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-N,3-dimethylbutanamide 1. (2R,3R,4S,5R,6S)-2-(Acetoxymethyl)-6-((1-(tert-butoxy)-3-methyl-1-oxobutan-2-yl)thio)-4-(4-(3,4,5-trifluorophenyl)-1H-1,2,3-triazol-1-yl)tetrahydro-2H-pyran-3,5-diyl diacetate TBAB (0.073 g, 0.23 mmol, 0.25 eq) is added to a solution of Intermediate 3 (0.50 g, 0.9 mmol) and tert-butyl 3-methyl-2-sulfanylbutanoate (0.24 g, 1.27 mmol, 1.4 eq) in EA (10.0 mL). Aq. 1M Na$_2$CO$_3$ is then added (2.0 mL) and the mixture is stirred at rt for 17 h. TBAB (1 spatula tip), tert-butyl 3-methyl-2-sulfanylbutanoate (5 drops) and aq. 1M Na$_2$CO$_3$ (1.0 mL) are added again. After 4 h of stirring at rt, the reaction mixture is diluted with EA (25.0 mL), followed by water (25.0 mL), and brine (25.0 mL). The phases are separated and the aq. layer is extracted with EA (50.0 mL). The combined organic phase is dried over Na$_2$SO$_4$, filtered and solvent removed in vacuo. The residue is purified by preparative HPLC/MS (I) to recover the title compound (0.2 g, 32%) as a beige solid, that is used without further purification. LC-MS (A): t$_R$=1.16 min; [M+H]$^+$: 660.31.

2. 2-(((2S,3R,4S,5R,6R)-3,5-Diacetoxy-6-(acetoxymethyl)-4-(4-(3,4,5-trifluorophenyl)-1H-1,2,3-triazol-1-yl)tetrahydro-2H-pyran-2-yl)thio)-3-methylbutanoic acid To a solution of (2R,3R,4S,5R,6S)-2-(acetoxymethyl)-6-((1-(tert-butoxy)-3-methyl-1-oxobutan-2-yl)thio)-4-(4-(3,4,5-trifluorophenyl)-1H-1,2,3-triazol-1-yl)tetrahydro-2H-pyran-3,5-diyl diacetate (0.2 g, 0.3 mmol) in DCM (45.0 mL) is added TFA (0.38 mL, 5.0 mmol, 17 eq) at rt. The reaction mixture is stirred at rt for 72 h, then neutralized with aq. 1N NaOH, diluted with DCM and the layers are separated. The aq. layer is extracted with DCM (3×). The combined organic layer is dried over Na$_2$SO$_4$, filtered and solvent removed in vacuo to recover the title compound (0.17 g, 96%) as a beige powder, that is not further purified. LC-MS (A): t$_R$=0.98 min; [M+H]$^+$: 604.28.

3. (2R,3R,4S,5R,6S)-2-(Acetoxymethyl)-6-((1-(ethyl(methyl)amino)-3-methyl-1-oxobutan-2-yl)thio)-4-(4-(3,4,5-trifluorophenyl)-1H-1,2,3-triazol-1-yl)tetrahydro-2H-pyran-3,5-diyl diacetate HATU (0.035 g, 0.087 mmol, 1.05 eq), followed by a solution of N-ethylmethylamine (97%, 0.015 mL, 0.17 mmol, 2.0 eq) and DIPEA (0.032 mL, 0.182 mmol, 2.2 eq) in DMF (2.0 mL) are added to a cooled (0° C.) solution of 2-(((2S, 3R,4S,5R,6R)-3,5-diacetoxy-6-(acetoxymethyl)-4-(4-(3,4,5-trifluorophenyl)-1H-1,2,3-triazol-1-yl)tetrahydro-2H-pyran-2-yl)thio)-3-methylbutanoic acid (0.05 g, 0.08 mmol) in DMF (2.0 mL). The reaction mixture is stirred at rt for 1.5 h, then it is partitioned between aq. 1N NaOH and DCM. The layers are separated, the aqueous layer is extracted with DCM, the combined organic layer is dried over $Na_2SO_4$, filtered and solvent removed in vacuo. The residue is purified by preparative HPLC/MS (I) to recover the title compound as a beige solid (0.044 g, 82%). LC-MS (A): $t_R$=1.03 min; $[M+H]^+$: 645.15.

4. 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-N,3-dimethylbutanamide (Reference Example 1)

$K_2CO_3$ (0.002 g, 0.012 mmol, 0.2 eq) is added at rt to a solution of (2R,3R,4S,5R,6S)-2-(acetoxymethyl)-6-((1-(ethyl(methyl)amino)-3-methyl-1-oxobutan-2-yl)thio)-4-(3,4,5-trifluorophenyl)-1H-1,2,3-triazol-1-yl)tetrahydro-2H-pyran-3,5-diyl diacetate (0.042 g, 0.06 mmol) in MeOH (20.0 mL). The reaction mixture is stirred at rt for 2 h, quenched with MeCN, followed by water and the mixture is directly purified by preparative HPLC/M S (I) to recover the title compound as a beige solid (0.032 g, 94%). LC-MS (A): $t_R$=0.085 min; $[M+H]^+$: 545.32.

Reference Example 2

Example 2.56.203S (S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-N-methyl-2-(tetrahydro-2H-pyran-4-yl)acetamide

1. Methyl 2-bromo-2-(tetrahydro-2H-pyran-4-yl)acetate

Methyl 2-(tetrahydro-2H-pyran-4-yl)acetate (5.0 g, 31.6 mmol) is dissolved in THF (60.0 mL) and cooled to −75° C. NaHMDS (1M in THF, 35.0 mL, 35.0 mmol, 1.1 eq) is added dropwise and the reaction mixture stirred for 30 min at −75° C. TMSCl (4.0 mL, 31.6 mmol, 1.0 eq) is added dropwise and stirring is continued for 1 h at −75° C. NBS (5.62 g, 31.6 mmol, 1.0 eq) is added, the cooling bath is removed and the mixture is stirred at rt for 1 h. It is then diluted with EA, the layers are separated, the organic layer is washed with water, dried over $Na_2SO_4$, filtered and solvent removed under reduced pressure. The residue is purified by CC on silica gel eluting with (Hept:/EA 3/1) to give methyl 2-bromo-2-(tetrahydro-2H-pyran-4-yl)acetate (5.8 g, 78%). $^1$H NMR (400 MHz, CDCl3) δ: 4.03 (d, J=9.3 Hz, 1H), 4.00 (m, 2H), 3.81 (s, 3H), 3.42 (m, 2H), 2.15 (m, 1H), 1.99 (m, 1H), 1.64 (m, 1H), 1.41 (m, 2H).

2. Methyl 2-(acetylthio)-2-(tetrahydro-2H-pyran-4-yl)acetate

To a solution of methyl 2-bromo-2-(tetrahydro-2H-pyran-4-yl)acetate (5.8 g, 24.5 mmol) in acetone (80.0 mL) is added potassium acetate (3.36 g, 29.5 mmol, 1.2 eq) at rt and stirring is continued for 1 h at rt. The reaction mixture is filtered and the filtrate is diluted with EA, washed with brine. The layers are separated and the organic layer is washed with water, dried over $Na_2SO_4$, filtered and solvent removed under reduced pressure to yield the title compound, that is not further purified. LC-MS (C): $t_R$=0.74 min; $[M+H]^+$: 233.19.

3. Methyl 2-mercapto-2-(tetrahydro-2H-pyran-4-yl)acetate

Sodium metal (0.20 g, 8.6 mmol) is dissolved in MeOH (100.0 mL), methyl 2-(acetylthio)-2-(tetrahydro-2H-pyran-4-yl)acetate (5.4 g, 23.2 mmol) is added and the reaction mixture is stirred at rt for 4 h. The reaction mixture is quenched with aq 10% citric acid, the layers are separated and the aq. layer is extracted with DCM (3×). The organic layer is washed with water, dried over $Na_2SO_4$, filtered and solvent removed under reduced pressure. The residue is purified by preparative HPLC/M S to yield methyl 2-mercapto-2-(tetrahydro-2H-pyran-4-yl)acetate (1.6 g, 36%). LC-MS (C): $t_R$=0.70 min; $[M+H]^+$: 191.36.

4. Methyl 2-(((2S,3R,4S,5R,6R)-3,5-bis(benzyloxy)-6-((benzyloxy)methyl)-4-(4-(3,4,5-trifluorophenyl)-1H-1,2,3-triazol-1-yl)tetrahydro-2H-pyran-2-yl)thio)-2-(tetrahydro-2H-pyran-4-yl)acetate To a solution of Intermediate 5 (3.05 g, 2.95 mmol) and methyl 2-mercapto-2-(tetrahydro-2H-pyran-4-yl)acetate (0.84 g, 4.43 mmol, 1.5 eq) in EA (65.0 mL) is added TBAB (0.24 g, 0.74 mmol, 0.25 eq), followed by aq. 1M $Na_2CO_3$ (15.0 mL) and the reaction mixture is stirred at rt for 30 min. 2-Mercapto-2-(tetrahydro-2H-pyran-4-yl)acetate (0.56 g, 3.0 mmol, 1.0 eq) is added again and stirring is continued at rt for 1 h. The reaction mixture is diluted with water (25.0 mL), the layers are separated and the aq. layer is extracted with EA (2×). The combined organic phase is dried over $Na_2SO_4$, filtered and concentrated in vacuo to recover the crude product that is purified by CC on silica gel eluting with EA/Hept 50/50, to give the title compound (1.3 g, 55%). LC-MS (C): $t_R$=1.36 min; $[M+H]^+$:804.47.

5. 2-(((2S,3R,4S,5R,6R)-3,5-bis(Benzyloxy)-6-((benzyloxy)methyl)-4-(4-(3,4,5-trifluorophenyl)-1H-1,2,3-triazol-1-yl)tetrahydro-2H-pyran-2-yl)thio)-2-(tetrahydro-2H-pyran-4-yl)acetic acid To a solution of methyl 2-(((2S,3R,4S,5R,6R)-3,5-bis(benzyloxy)-6-((benzyloxy)methyl)-4-(4-(3,4,5-trifluorophenyl)-1H-1,2,3-triazol-1-yl)tetrahydro-2H-pyran-2-yl)thio)-2-(tetrahydro-2H-pyran-4-yl)acetate (1.3 g, 1.62 mmol) in THF (25.0 ml) and EtOH (15.0 mL) is added aq. 1M NaOH (15.0 mL) and it is stirred at rt for 1.5 h. The reaction mixture is quenched with aq. 1 M HCl (pH=5), the layers are separated and the aq. layer is extracted with EA (2×). The combined organic phase is dried over $Na_2SO_4$, filtered and concentrated in vacuo to recover the crude that is purified by preparative HPLC/M S to yield the title compound (0.65 g, 51%). LC-MS (C): $t_R$=1.29 min; $[M+H]^+$:790.21.

6. 2-(((2S,3R,4S,5R,6R)-3,5-bis(Benzyloxy)-6-((benzyloxy)methyl)-4-(4-(3,4,5-trifluorophenyl)-1H-1,2,3-triazol-1-yl)tetrahydro-2H-pyran-2-yl)thio)-N-ethyl-N-methyl-2-(tetrahydro-2H-pyran-4-yl)acetamide 2-(((2S,3R,4S,5R,6R)-3,5-bis(Benzyloxy)-6-((benzyloxy)methyl)-4-(4-(3,4,5-trifluorophenyl)-1H-1,2,3-triazol-1-yl)tetrahydro-2H-pyran-2-yl)thio)-2-(tetrahydro-2H-pyran-4-yl)acetic acid (0.63 g, 0.8 mmol) is dissolved in DMF (15.0 ml) and the solution cooled to 0° C. DIPEA (0.27 mL, 0.755 mmol, 2.0 eq) is added followed by ethylmethylamine (0.14 mL, 1.6 mmol, 2.0 eq), then HATU (0.33 g, 0.84 mmol, 1.0 eq) and stirring is continued at rt for 1 h. The reaction mixture is diluted with water and a spatula of NaCl is added, the layers are separated, and the aq. layer is extracted with EA (2×). The combined organic phase is dried over $Na_2SO_4$, filtered and concentrated in vacuo to recover the crude product that is purified by CC on silica gel eluting with EA/Hept 50/50 to 100/0 to give the title compound (0.6 g, 91%). LC-MS (C): $t_R$=1.33 min; [M+H]$^+$:831.52.

7. 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-N-methyl-2-(tetrahydro-2H-pyran-4-yl)acetamide To a cooled (0° C.) solution of 2-(((2S,3R,4S,5R,6R)-3,5-bis(benzyloxy)-6-((benzyloxy)methyl)-4-(4-(3,4,5-trifluorophenyl)-1H-1,2,3-triazol-1-yl)tetrahydro-2H-pyran-2-yl)thio)-N-ethyl-N-methyl-2-(tetrahydro-2H-pyran-4-yl)acetamide (0.55 g, 0.66 mmol) in DCM (20.0 mL) is added BBr$_3$ (1M in DCM, 4.0 mL). The reaction mixture is stirred at 0° C. for 10 min, then quenched by the addition of ice-water. The layers are separated, and the aq. layer is extracted with DCM (2x). The combined organic phase is dried over Na$_2$SO$_4$, filtered and concentrated in vacuo to recover the crude product that is purified by preparative HPLC/MS (I) to give the title compound (0.035 g, 9%). LC-MS (C): $t_R$=0.72 min; [M+H]$^+$:562.21.

8. (S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-N-methyl-2-(tetrahydro-2H-pyran-4-yl)acetamide (Reference Example 2)

Separation of the epimers of Example 2.56.203S. (0.035 g) by chiral preparative HPLC(I) yielded the title compound (0.004 g). LC-MS (C): $t_R$=0.72 min; [M+H]$^+$: 562.21. Chiral analytical HPLC (E): $t_R$=2.36 min.

LC-MS and Gal-3 inhibition data from Reference Examples 1 and 2 are listed in Table 1 below. The LC-MS conditions used were LC-MS (A) for Reference Example 1 and LC-(MS (C) for Reference Example 2.

TABLE 1

| Example | Name | $t_R$ min | [M + H]$^+$ | IC$_{50}$ [uM] |
|---|---|---|---|---|
| 2.53.203. Ref. 1 | 2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-N,3-dimethylbutanamide | 0.79 | 519.14 | 7.8 |
| 2.56.203S. Ref. 2 | (S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-N-methyl-2-(tetrahydro-2H-pyran-4-yl)acetamide | 0.74 | 562.21 | 6.86 |

Preparation of the Compounds of Structure 1 and Examples Thereof

Example 2.41.200

2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-isobutyl-N-methylacetamide

1. 2-(((2S,3R,4S,5R,6R)-3,5-bis((4-Chlorobenzyl)oxy)-6-(((4-chlorobenzyl)oxy)methyl)-4-(4-(3,4,5-trifluorophenyl)-1H-1,2,3-triazol-1-yl)tetrahydro-2H-pyran-2-yl)thio)-N-isobutyl-N-methylacetamide Intermediate 4 (0.60 g, 0.44 mmol) and N-isobutyl-2-mercapto-N-methylacetamide (Intermediate 6) (0.10 g, 0.44 mmol, 1.0 eq) are dissolved in EA (12.5 mL). TBAB (0.036 g, 0.11 mmol, 0.25 eq) in aq. 1M Na$_2$CO$_3$ (6.25 mL) is added and stirring is continued for 17 h. The reaction mixture is diluted with EA (25.0 mL), water (25.0 mL) and brine (25.0 mL), the phases are separated and the aq. layer is extracted with EA (50.0 mL). The combined organic phase is dried over Na$_2$SO$_4$, filtered and concentrated in vacuo. The material is purified by preparative HPLC/MS (I) to recover the title compound (0.064 g, 16%) as a beige solid. LC-MS (A): $t_R$=1.30 min; [M+H]$^+$: 877.23.

2. 2-(((2S,3R,4S,5R,6R)-3,5-bis((4-Chlorobenzyl)oxy)-6-(((4-chlorobenzyl)oxy)methyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-isobutyl-N-methylacetamide To a cooled (−78° C.) solution of 2-(((2S,3R,4S,5R,6R)-3,5-bis((4-chlorobenzyl)oxy)-6-(((4-chlorobenzyl)oxy)methyl)-4-(4-(3,4,5-trifluorophenyl)-1H-1,2,3-triazol-1-yl)tetrahydro-2H-pyran-2-yl)thio)-N-isobutyl-N-methylacetamide (0.03 g, 0.03 mmol) and TMEDA (0.01 mL, 0.07 mmol, 2.2 eq) in THF (1.8 mL), is added dropwise LDA (1.0 M in THF/Hept/ethylbenzene, 0.07 mL, 0.07 mmol, 2.2 eq). The solution is stirred at −78° C. for 1 h, tetrahydro-4H-pyran-4-one (0.004 mL, 0.004 mmol, 1.2 eq) is added at −78° C. After 1 h the reaction mixture is quenched at −78° C. with aq. sat. NH$_4$C$_1$, warmed to rt and diluted with EA and toluene. The phases are separated, the organic phase is dried over Na$_2$SO$_4$, filtered and solvent removed in vacuo. The crude is purified by preparative HPLC/MS (I) to recover the title compound (0.022 g, 75%) as a beige solid. LC-MS (A): $t_R$=1.31 min; [M+H]$^+$: 979.31.

3. 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-isobutyl-N-methylacetamide (2.41.200.)

To a cooled (0° C.) solution of 2-(((2S,3R,4S,5R,6R)-3,5-bis((4-chlorobenzyl)oxy)-6-(((4-chlorobenzyl)oxy)methyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-isobutyl-N-methylacetamide (0.022 g, 0.023 mmol) in DCM (5.0 mL) is added BBr$_3$ (1M in DCM, 0.14 mL, 6.0 eq). The reaction mixture is stirred at 0° C. for 2 h, quenched with dropwise addition of water at 0° C. The mixture is extracted with DCM (2x), the layers are separated and the combined org. layer is washed with brine, dried over Na$_2$SO$_4$, filtered and concentrated under reduced pressure. The crude is purified by preparative HPLC/MS (I) to recover the title compound (0.003 g, 24%) as a beige powder. LC-MS (A): $t_R$=0.79 min; [M+H]$^+$: 605.49.

Example 2.41.200R (R)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-isobutyl-N-methylacetamide (2.41.200R.)

Separation of the epimers of Example 2.41.200. (0.022 g) by chiral preparative HPLC (II) yielded the title compound (0.013 g) as a beige solid. Chiral analytical HPLC (F): $t_R$=1.44 min; [M+H]$^+$: 605.41. $^1$H NMR (400 MHz, MeOD)

δ: 8.6, (s, 1H), 7.65 (m, 2H), 4.9-4.82 (m, 2H), 4.24-4.13 (m, 3H), 3.91-3.83 (m, 1H), 3.82-3.73 (m, 6H), 3.35-3.18 (m, 2H), 3.29 (s, 2.5H), 2.97 (s, 0.5H), 1.92-2.13 (m, 2H), 1.83-1.73 (m, 1H), 1.67-1.55 (m, 1H), 1.6-0.92 (m, 6H).

Example 2.41.200S (S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetra hydro-2H-pyran-2-yl)thio)-2-(4-hydroxytetrahydro-2H-pyran-4-4-N-isobutyl-N-methylacetamide Separation of the epimers of Example 2.41.200. (0.022 g) by chiral preparative HPLC (II) yielded Example 2.41.200S. (0.013 g) as a beige solid. Chiral analytical HPLC (F): $t_R$=2.02 min; [M+H]$^+$: 605.41.

LC-MS and Gal-3 inhibition data of Example 2.41.200. are listed in Table 2 below. The LC-MS conditions used were LC-MS (A). Chiral HPLC (conditions and retention time) and inhibition data of the epimers R and S of Example 2.41.200. are also listed.

2. 2-(((2S,3R,4S,5R,6R)-3,5-bis((4-Chlorobenzyl)oxy)-6-(((4-chlorobenzyl)oxy)methyl)-4-(4-(3,4,5-trifluorophenyl)-1H-1,2,3-triazol-1-yl)tetrahydro-2H-pyran-2-yl)thio)-3-hydroxy-3-methylbutanoic acid TFA (0.23 mL, 3.0 mmol, 5.0 eq) is added at rt to a solution of tert-butyl 2-(((2S,3R,4S,5R,6R)-3,5-bis((4-chlorobenzyl)oxy)-6-(((4-chlorobenzyl)oxy)methyl)-4-(4-(3,4,5-trifluorophenyl)-1H-1,2,3-triazol-1-yl)tetrahydro-2H-pyran-2-yl)thio)-3-hydroxy-3-methylbutanoate (0.55 g, 0.6 mmol) in DCM (50.0 mL) and stirred at rt for 17 h. TFA (0.23 mL, 1.55 mmol, 5.0 eq) is added again and stirred at rt for additional 48 h. The mixture is carefully neutralized with aq. 1M NaOH, diluted with DCM and the layers are separated. The aqueous layer is extracted with DCM (3×). The combined organic layer is dried over $Na_2SO_4$, filtered and solvent removed in vacuo to recover the crude title compound as a beige solid (0.48 g, 93%), that is used without further purification. LC-MS (A): $t_R$=1.21 min; [M+H]$^+$: 868.10.

TABLE 2

| Example | Name | $t_R$ [min] | [M + H]$^+$ | Chiral HPLC | $t_R$ chiral [min] | IC$_{50}$ [uM] |
|---|---|---|---|---|---|---|
| 2.41.200. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-isobutyl-N-methylacetamide | 0.79 | 605.41 | | | 0.06 |
| 2.41.200R. | (R)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-isobutyl-N-methylacetamide | 0.79 | 605.41 | Chiralcel OJ-H B: 15% MeOH 5 min run | 1.47 | 4.01 |
| 2.41.200S. | (S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-isobutyl-N-methylacetamide | 0.79 | 605.41 | Chiralcel OJ-H B: 15% MeOH 5 min run | 2.02 | 0.05 |

Example 2.31.201

2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N,N,3-trimethylbutanamide 1. tert-Butyl 2-(((2S,3R,4S,5R,6R)-3,5-bis((4-Chlorobenzyl)oxy)-6-(((4-chlorobenzyl)oxy)methyl)-4-(4-(3,4,5-trifluorophenyl)-1H-1,2,3-triazol-1-yl)tetrahydro-2H-pyran-2-yl)thio)-3-hydroxy-3-methylbutanoate Intermediate 4 (1.6 g, 1.2 mmol) and tert-butyl 3-hydroxy-2-mercapto-3-methylbutanoate (Intermediate 7) (0.35 g, 1.7 mmol, 1.4 eq) are dissolved in EA (12.5 mL) and TBAB (0.89 g, 1.55 mmol, 0.25 eq) in aq. 1M $Na_2CO_3$ (6.2 mL) is added. The mixture is stirred for 17 h and diluted with EA (25.0 mL), water (25.0 mL) and brine (25.0 mL). The phases are separated and the aq. layer is extracted with EA (50.0 mL). The combined organic phase is dried over $Na_2SO_4$, filtered and solvent removed in vacuo. The residue is purified by preparative HPLC/MS(II) to recover the title compound as a beige solid (0.55 g, 49%). LC-MS (A): $t_R$=1.33 min; [M+H]$^+$: 922.15.

3. 2-(((2S,3R,4S,5R,6R)-3,5-bis((4-Chlorobenzyl)oxy)-6-(((4-chlorobenzyl)oxy)methyl)-4-(4-(3,4,5-trifluorophenyl)-1H-1,2,3-triazol-1-yl)tetrahydro-2H-pyran-2-yl)thio)-3-hydroxy-N,N,3-trimethylbutanamide To a solution of crude 2-(((2S,3R,4S,5R,6R)-3,5-bis((4-chlorobenzyl)oxy)-6-(((4-chlorobenzyl)oxy)methyl)-4-(4-(3,4,5-trifluorophenyl)-1H-1,2,3-triazol-1-yl)tetrahydro-2H-pyran-2-yl)thio)-3-hydroxy-3-methylbutanoic acid (0.8 g, 0.09 mmol) in DMF (1.0 mL) at rt are successively added EDC HCl (0.044 mg, 0.23 mmol, 2.5 eq), HOBT (0. 017 g, 0.11 mmol, 1.2 eq), 4-DMAP (0.003 g, 0.023 mmol, 0.25 eq), DIPEA (0.047 mL, 0.277 mmol, 3.0 eq) and dimethyl amine (0.008 g, 0.185 mmol, 2.0 eq). The reaction mixture is stirred at rt for 4 h, then dimethylamine (0.002 g, 0.0046 mmol, 0.5 eq), DIPEA (0.008 mL, 0.07 mmol, 0.5 eq), a spatula tip of each HOBT, EDC HCl and 4-DMAP are added again. After additional 2 h at rt the reaction mixture is partitioned between aq. 1N NaOH and EA, the layers are separated and the aqueous layer is extracted with EA. The combined organic layer is dried over $Na_2SO_4$, filtered and solvent removed in vacuo. The crude is purified by preparative HPLC/MS (I) to recover the title compound (0.018 g, 22%) as a beige solid. LC-MS (A): $t_R$=1.25 min; [M+H]$^+$: 895.56.

4. 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N,N,3-trimethylbutanamide (2.31.201.)

To a cooled (0° C.) solution of 2-(((2S,3R,4S,5R,6R)-3,5-bis((4-chlorobenzyl)oxy)-6-(((4-chlorobenzyl)oxy)methyl)-4-(4-(3,4,5-trifluorophenyl)-1H-1,2,3-triazol-1-yl)tetrahydro-2H-pyran-2-yl)thio)-3-hydroxy-N,N,3-trimethylbutanamide (0.018 g, 0.02 mmol) in DCM (2.0 mL) is added $BBr_3$ solution (1M in DCM, 0.2 mL, 10.0 eq). The reaction mixture is stirred at 0° C. for 1.5 h, then quenched through dropwise addition of water at 0° C. The layers are separated, the aq. layer is extracted with DCM (2×), the combined org. layer is washed with brine, dried over $Na_2SO_4$, filtered and concentrated under reduced pressure. The residue is purified by preparative HPLC/MS (I) to recover the title compound as a beige powder (0.008 g, 73%). LC-MS (A): $t_R$=0.67 min; $[M+H]^+$: 521.41.

Example 2.31.203R (R)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-3-hydroxy-N,3-dimethylbutanamide 0.31.203R.)

Example 2.31.203. is prepared as described for Example 2.31.201. Separation of the epimer of Example 2.31.203.

(0.097 g) by chiral preparative HPLC (III) yielded the title compound (0.029 g) as a white powder. Chiral analytical HPLC (G): $t_R$=1.43 min.

Example 2.31.203S (S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-0)thio)-N-ethyl-3-hydroxy-N,3-dimethylbutanamide Separation of th. epimer of Example 2.31.203. (0.097 g) by chiral preparative HPLC (III) in analogy to Example 2.31.203R. yielded the title compound (0.047 g) as a white powder. Chiral analytical HPLC (G): $t_R$=2.1 min.

Following examples are prepared starting from either Intermediate 4 or Intermediate 5 and Intermediate 7, according to the procedures described for Example 2.31.201. LC-MS and Gal-3 inhibition data are listed in Table 3 below. The LC-MS conditions used are LC-MS (A). Chiral analytical HPLC (I) (conditions and retention time) and inhibition data of the epimers R and S of selected Examples are also listed.

TABLE 3

| Example | Name | $t_R$ [min] | $[M + H]^+$ | Chiral HPLC | $t_R$ chiral [min] | $IC_{50}$ [uM] |
|---|---|---|---|---|---|---|
| 2.31.201. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N,N,3-trimethylbutanamide | 0.67 | 521.41 | | | 0.27 |
| 2.31.203. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-3-hydroxy-N,3-dimethylbutanamide | 0.71 | 535.22 | | | 0.21 |
| 2.31.203R. | (R)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-3-hydroxy-N,3-dimethylbutanamide | 0.73 | 535.05 | Chiralpak IC B: 35% EtOH 5 min run | 1.43 | 3.88 |
| 2.31.203S. | (S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-3-hydroxy-N,3-dimethylbutanamide | 0.72 | 535.05 | Chiralpak IC B: 35% EtOH 5 min run | 2.1 | 0.07 |
| 2.31.202. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N,N-diethyl-3-hydroxy-3-methylbutanamide | 0.75 | 549.17 | | | 0.16 |
| 2.31.204. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-methyl-1-(2-methylazetidin-1-yl)butan-1-one | 0.70 | 548.29 | | | 0.14 |
| 2.31.205R.* | (R)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-methyl-1-(3-methylazetidin-1-yl)butan-1-one | 0.70 | 548.27 | Chiralcel OJH B: 10% EtOH 5 min run | 2.77 | 2.13 |
| 2.31.205S.* | (S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-methyl-1-(3-methylazetidin-1-yl)butan-1-one | 0.70 | 548.27 | Chiralcel OJH B: 10% EtOH 5 min run | 2.00 | 0.27 |
| 2.31.206. | 1-(Azetidin-1-yl)-2-(((2S,3R,4S,5R,6R)-3,5-dihydroxy-6-(hydroxymethyl)-4-(4-(3,4,5-trifluorophenyl)-1H-1,2,3-triazol-1- | 0.66 | 533.39 | | | 0.20 |

TABLE 3-continued

| Example | Name | $t_R$ [min] | [M + H]⁺ | Chiral HPLC | $t_R$ chiral [min] | IC$_{50}$ [uM] |
|---|---|---|---|---|---|---|
| | yl)tetrahydro-2H-pyran-2-yl)thio)-3-hydroxy-3-methylbutan-1-one | | | | | |

*Epimers are separated during the purification on preparative HPLC/MS(I) or HPLC/MS(II).

Following examples are prepared starting from Intermediate 4 or Intermediate 5 and either Intermediate 8 or Intermediate 9, according to the procedures described for Example 2.31.201. LC-MS and Gal-3 inhibition data are listed in Table 4 below. The LC-MS conditions used are LC-MS (A). Chiral analytical HPLC (I) (conditions and retention time) and inhibition data of the epimers R and S of selected Examples are also listed.

TABLE 4

| Example | Name | $t_R$ [min] | [M + H]⁺ | Chiral HPLC | $t_R$ chiral [min] | IC$_{50}$ [uM] |
|---|---|---|---|---|---|---|
| 2.40.200. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxy-1-methylpiperidin-4-yl)-N-isobutyl-N-methylacetamide | 0.61 | 589.81 | | | 0.08 |
| 2.40.203. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxy-1-methylpiperidin-4-yl)-N-methylacetamide | 0.68 | 618.04 | | | 0.08 |
| 2.40.207. | N-Benzyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxy-1-methylpiperidin-4-yl)-N-methylacetamide | 0.71 | 652.01 | | | 0.09 |
| 2.40.208. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxy-1-methylpiperidin-4-yl)-1-(piperidin-1-yl)ethan-1-one | 0.66 | 616.03 | | | 0.03 |
| 2.40.209. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxy-1-methylpiperidin-4-yl)-1-(indolin-1-yl)ethan-1-one | 0.71 | 649.91 | | | 0.12 |
| 2.41.201. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N,N-dimethylacetamide | 0.66 | 563.36 | | | 0.18 |
| 2.41.201R. | (R)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N,N-dimethylacetamide | 0.66 | 563.36 | Chiralcel OJ-H B: 20% MeOH 3 min run | 1.26 | 4.1 |
| 2.41.201S. | (S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N,N-dimethylacetamide | 0.66 | 563.36 | Chiralcel OJ-H B: 20% MeOH 3 min run | 1.65 | 0.06 |
| 2.41.202. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N,N-diethyl-2-(4-hydroxytetrahydro-2H-pyran-4-yl)acetamide | 0.75 | 590.93 | | | 0.05 |
| 2.41.204. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-1-(2-methylazetidin-1-yl)ethan-1-one | 0.69 | 589.33 | | | 0.21 |
| 2.41.205R.* | (R)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-1-(3-methylazetidin-1-yl)ethan-1-one | 0.69 | 589.34 | Chiralpak IB B: 25% (1/1) MeCN/EtOH 5 min run | 3.2 | 1.00 |
| 2.41.205S.* | (S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-1-(3-methylazetidin-1-yl)ethan-1-one | 0.7 | 589.34 | Chiralpak IB B: 25% (1/1) MeCN/EtOH 5 min run | 2.83 | 0.12 |

TABLE 4-continued

| Example | Name | $t_R$ [min] | $[M + H]^+$ | Chiral HPLC | $t_R$ chiral [min] | $IC_{50}$ [uM] |
|---|---|---|---|---|---|---|
| 2.41.206. | 1-(Azetidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)ethan-1-one | 0.65 | 575.35 | | | 0.26 |
| 2.41.207. | N-Benzyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methylacetamide | 0.82 | 639.1 | | | 0.07 |
| 2.41.207R. | (R)-N-Benzyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methylacetamide | 0.82 | 639.1 | Chiralpak ID B: 35% 2ProOH 5 min run | 2.71 | 8.23 |
| 2.41.207S. | (S)-Benzyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methylacetamide | 0.82 | 639.1 | Chiralpak ID B: 35% 2ProOH 5 min run | 3.47 | 0.04 |
| 2.41.208. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-1-(piperidin-1-yl)ethan-1-one | 0.75 | 603.16 | | | 0.09 |
| 2.41.208R. | (R)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-1-(piperidin-1-yl)ethan-1-one | 0.75 | 603.16 | Chiralcel OJ-H B: 25% MeOH 5 min | 1.07 | 1.65 |
| 2.41.208S. | (S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-1-(piperidin-1-yl)ethan-1-one | 0.75 | 603.16 | Chiralcel OJ-H B: 25% MeOH 5 min run | 1.67 | 0.02 |
| 2.41.209. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-1-(indolin-1-yl)ethan-1-one | 0.83 | 636.98 | | | 0.15 |
| 2.41.209R. | (R)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-1-(indolin-1-yl)ethan-1-one | 0.83 | 636.98 | Chiralpak ID B: 45% EtOH 5 min run | 1.26 | 1.31 |
| 2.41.209S. | (S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-1-(indolin-1-yl)ethan-1-one | 0.83 | 636.98 | Chiralpak ID B: 45% EtOH 5 min run | 1.75 | 0.1 |
| 2.41.210. | 2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(thiophen-2-ylmethyl)acetamide | 0.81 | 645.06 | | | 0.44 |
| 2.41.211. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-1-(pyrrolidin-1-yl)ethan-1-one | 0.69 | 589.11 | | | 0.13 |
| 2.41.212. | (R)-N-(cyclopentylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methylacetamide | 0.85 | 631.03 | | | 0.08 |
| 2.41.212R. | (S)-N-(cyclopentylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methylacetamide | 0.85 | 631.03 | Chiralcel OJ-H B: 15% MeOH 5 min run | 1.76 | 6.35 |
| 2.41.212S. | (S)-N-Cyclopentylmethyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methylacetamide | 0.85 | 631.03 | Chiralcel OJ-H B: 15% MeOH 5 min run | 2.75 | 0.01 |

TABLE 4-continued

| Example | Name | $t_R$ [min] | [M + H]+ | Chiral HPLC | $t_R$ chiral [min] | $IC_{50}$ [uM] |
|---|---|---|---|---|---|---|
| 2.41.213. | 2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-((tetrahydro-2H-pyran-4-yl)methyl)acetamide | 0.72 | 647.01 | | | 0.08 |
| 2.41.214. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxytetrahydro-2H-pyran-4-yl)-N-((tetrahydro-2H-pyran-4-yl)methyl)acetamide | 0.76 | 661.03 | | | 0.03 |
| 2.41.215. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-((1-methyl-1H-imidazol-4-yl)methyl)acetamide | 0.6 | 643.02 | | | 0.06 |
| 2.41.216. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(2-(tetrahydro-2H-pyran-4-yl)ethyl)acetamide | 0.75 | 661 | | | 0.06 |
| 2.41.216R. | (R)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(2-(tetrahydro-2H-pyran-4-yl)ethyl)acetamide | 0.75 | 661 | Chiralcel OJ-H B: 15% MeOH 5 min run | 1.89 | 1.53 |
| 2.41.216S. | (S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(2-(tetrahydro-2H-pyran-4-yl)ethyl)acetamide | 0.75 | 661 | Chiralcel OJ-H B: 15% MeOH 5 min run | 3.5 | 0.02 |
| 2.41.217. | N-(2-Cyclopropylethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methylacetamide | 0.8 | 617.01 | | | 0.06 |
| 2.41.218. | N-(Cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methylacetamide | 0.76 | 603.02 | | | 0.8 |
| 2.41.218R. | (R)-N-(Cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methylacetamide | 0.76 | 603.02 | Chiralcel OJ-H B: 15% MeOH 5 min run | 1.7 | 2.25 |
| 2.41.218S. | (S)-N-(Cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methylacetamide | 0.76 | 603.02 | Chiralcel OJ-H B: 15% MeOH 5 min run | 2.81 | 0.02 |

*Epimers are separated during the purification on preparative HPLC/MS(I) or HPLC/MS(II).

Example 2.41.203

2-(((2S,3R,4S,5R,6R)-3,5-Dihydroxy-6-(hydroxymethyl)-4-(4-(3,4,5-trifluorophenyl)-1H-1,2,3-triazol-1-yl)tetra hydro-2H-pyran-2-yl)thio)-N-ethyl-2-(4-hydroxytetrahydro-2H-pyran-4-yl)-N-methylacetamide 1. (2R,3R,4S,5R,6S)-2-(Acetoxymethyl)-6-((2-(tert-butoxy)-1-(4-hydroxytetrahydro-2H-pyran-4-yl)-2-oxoethyl)thio)-4-(4-(3,4,5-trifluorophenyl)-1H-1, 2, 3-triazol-1-yl)tetra hydro-2H-pyran-3,5-diyl diacetate TBAB (0. 22 g, 0.681 mmol, 0.25 eq) is added to a solution of Intermediate 3 (1.5 g, 2.73 mmol) and tert-butyl 2-(4-hydroxytetrahydro-2H-pyran-4-yl)-2-mercaptoacetate (Intermediate 8) (0. 95 g 1.4 eq) in EA (35.0 mL) followed by aq. 1M $Na_2CO_3$ (8.0 mL). The mixture is stirred at rt for 17 h, diluted with EA (25.0 mL), water (25.0 mL) and brine (25.0 mL). The phases are separated and the aq. layer is extracted with EA (50.0 mL). The combined organic phase is dried over $Na_2SO_4$, filtered and concentrated in vacuo. The residue is purified by Flash Master (ISCO; compound linked on isolute and eluted with EA/Hept 0/100 to 70/30) to recover the title compound as a beige powder (1.8 g, 91%). LC-MS (A): $t_R$=1.04-1.05 min; [M+H]$^+$: 717.92.

2. 2-(((2S,3R,4S,5R,6R)-3,5-Diacetoxy-6-(acetoxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)acetic acid To a solution of (2R,3R,4S,5R,6S)-2-(acetoxymethyl)-6-(((2-(tert-butoxy)-1-(4-hydroxytetrahydro-2H-pyran-4-yl)-2-oxoethyl)thio)-4-(4-(3,4,5-trifluorophenyl)-1H-1,2,3-triazol-1-yl)tetrahydro-2H-pyran-3,5-diyl diacetate (3.8 g, 4.32 mmol) in DCM (80.0 mL) is added TFA (4.9 mL, 17.0 eq) at rt. The reaction mixture is stirred at rt for 17 h, carefully quenched by the addition of aq. 2N NaOH (until pH=7), diluted with DCM and the layers separated. The aqueous layer is extracted with EA (3×). The combined organic layer is dried over $Na_2SO_4$, filtered and solvent removed in vacuo to recover the title compound as a beige powder (3.8 g, >99%), that is used without further purification. LC-MS (A): $t_R$=0.86 min; [M+H]$^+$: 662.29.

3. (2R,3R,4S,5R,6S)-2-(Acetoxymethyl)-6-((2-(ethyl(methyl)amino)-1-(4-hydroxytetrahydro-2H-pyran-4-yl)-2-oxoethyl)thio)-4-(4-(3,4,5-trifluorophenyl)-1H-1,2,3-triazol-1-yl)tetrahydro-2H-pyran-3,5-diyl diacetate 2-(((2S,3R,4S,5R,6R)-3,5-Diacetoxy-6-(acetoxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)acetic acid (4.0 g, 6.0 mmol) is dissolved in DMF (40.0 mL). HATU (2.53 g, 6.32 mmol, 1.05 eq) followed by a solution of N-ethylmethylamine (0.8 mL, 9.03 mmol, 1.5 eq) and DIPEA (1.8 mL, 10.2 mmol, 1.7 eq) in DMF (10.0 mL) are added. The reaction mixture is stirred at rt for 17 h, then partitioned between EA and water. The organic phase is washed with water and the combined aq. phase is extracted with EA. The combined organic phase is dried over $Na_2SO_4$, filtered and concentrated in vacuo to recover the crude that is purified by Flash Master (ISCO, Column 80 g, compound linked on isolute and eluted with EA/Hept 35/65 to 100/0.

The title compound is obtained as a beige powder (2.28 g, 54%). LC-MS (A): $t_R$=0.96 min; [M+H]$^+$: 703.16.

4. 2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxytetrahydro-2H-pyran-4-yl)-N-methylacetamide (2.41.203.)

To a solution of (2R,3R,4S,5R,6S)-2-(acetoxymethyl)-6-(((2-(ethyl(methyl)amino)-1-(4-hydroxytetrahydro-2H-pyran-4-yl)-2-oxoethypthio)-4-(4-(3,4,5-trifluorophenyl)-1H-1,2,3-triazol-1-yl)tetrahydro-2H-pyran-3,5-diyl diacetate (0.72 g, 1.02 mmol) in MeOH (10.0 mL) is added $K_2CO_3$ (0.028 g, 0.2 eq) at rt. The reaction mixture is stirred at rt, diluted with MeCN and water and directly purified by preparative HPLC/MS(I) to recover the title compound as a beige powder (0.5 g, 85%). LC-MS (A): $t_R$=0.71 min; [M+H]$^+$: 577.98.

Example 2.41.203R (R)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxytetrahydro-2H-pyran-4-yl)-N-methylacetamide Separation of the epimers of Example 2.41.203. (2.77 g) by chiral preparative HPLC/MS (IV) yielded the title compound (0.88 g) as a white powder. Chiral analytical HPLC (H): $t_R$=1.53 min; [M+H]$^+$: 605.41. $^1$H NMR (400 MHz, MeOD) δ: 8.53 (s, 0.4H), 8.51 (s, 0.6H), 7.65 (m, 2H), 4.87 (m, 1H), 4.82 (d, J1=9.5 Hz, 1.0 H), 4.2 (t, 10.5 Hz, 1H), 4.16 (s, 1H), 4.4 (d, J=2.5 Hz, 1H), 3.95-3.71 (m, 7H), 3.55-3.4 (m, 2H), 3.28 (s, 1.8H), 2.7 (s, 1.2H), 2.13-1.92 (m, 2H), 1.83-1.73 (m, 1H), 1.62-1.55 (m, 1H), 1.3 (t, J=7.0 Hz, 1.3 H), 1.15 (t, J=7.0 Hz, 1.8 H).

Example 2.41.203S (S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxytetrahydro-2H-pyran-4-yl)-N-methylacetamide[1,3-di-deoxy-1-((N-ethyl-2-(4-hydroxytetrahydro-2H-pyran-4-yl)-N-methylacetamide)-(S)-thio)-3-[4-(3,4,5-trifluorophenyl)-1H-1,2,3-triazol-1-yl]-β-D-qalactopyranoside]

Separation of the epimers of Example 2.41.203. (2.77 g) by chiral preparative HPLC/MS (IV) yielded the title compound (0.163 g) as a white powder. Chiral analytical HPLC (H): $t_R$=2.4 min; [M+H]$^+$: 605.41. $^1$H NMR (400 MHz, MeOD) δ: 8.58 (s, 0.6H), 8.56 (s, 0.4H), 7.65 (m, 2H), 4.9-4.85 (m, 1H), 4.78 (d, J=9.5 Hz, 0.5H), 4.74 (d, J=9.3 Hz, 0.5H), 4.25 (t, 10.5 Hz, 1H), 4.21 (s, 0.5H), 4.16 (s, 0.5H), 4.13 (m, 1H), 3.85-3.71 (m, 7H), 3.6-3.4 (m, 2H), 3.25 (s, 1.8H), 3.0 (s, 1.2H), 2.13-1.92 (m, 2H), 1.83-1.73 (m, 1H), 1.62-1.55 (m, 1H), 1.3 (t, J=7.3 Hz, 1.3 H), 1.14 (t, J=7.0 Hz, 1.8 H).

Following examples are prepared starting from tert-butyl sulfanyl acetate, the corresponding cyclic ketones (Intermediate 8, 9, and analogous) and Intermediate 3, according to the procedures described for Example 2.41.201. LC-MS and Gal-3 inhibition data are listed in Table 5 below. The LC-MS conditions used are LC-MS (A). Chiral analytical HPLC (I) (conditions and retention time) and inhibition data of the epimers R and S of selected Examples are also listed.

TABLE 5

| Example | Name | $t_R$ [min] | [M + H]+ | Chiral HPLC | $t_R$ chiral [min] | IC$_{50}$ [uM] |
|---|---|---|---|---|---|---|
| 2.41.203. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxytetrahydro-2H-pyran-4-yl)-N-methylacetamide | 0.7 | 577.05 | | | 0.09 |
| 2.41.203R. | (R)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxytetrahydro-2H-pyran-4-yl)-N-methylacetamide | 0.7 | 577.05 | Chiralcel OJ-H B: 15% MeOH 5 min run | 1.53 | 4.43 |
| 2.41.203S. | (S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxytetrahydro-2H-pyran-4-yl)-N-methylacetamide | 0.7 | 577.05 | Chiralcel OJ-H B: 15% MeOH 5 min run | 2.4 | 0.03 |
| 2.41.219. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(2,2,2-trifluoroethyl)acetamide | 0.78 | 631.16 | | | 0.11 |
| 2.41.236. | N-(Cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxytetrahydro-2H-pyran-4-yl)acetamide | 0.8 | 618.1 | | | 4.47 |
| 2.41.235. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(oxetan-3-yl)acetamide | 0.66 | 605.4 | | | 0.06 |
| 2.41.235R. | (R)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(oxetan-3-yl)acetamide | | | Chiracel OJ-H B: 20% (1/1) ACN/EtOH 5 min run | 1.71 | 2.4 |
| 2.41.235S. | (S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(oxetan-3-yl)acetamide | | | Chiracel OJ-H B: 20% (1/1) ACN/EtOH 5 min run | 1.26 | 0.04 |
| 2.39.203. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(1-hydroxycyclohexyl)-N-methylacetamide | 0.81 | 575.3 | | | 0.07 |
| 2.39.208. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclohexyl)-1-(piperidin-1-yl)ethan-1-one | 0.87 | 601.3 | | | 0.02 |
| 2.39.219R.* | (R)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclohexyl)-N-methyl-N-(2,2,2-trifluoroethyl)acetamide | 0.89 | 629.20 | Chiralpak IB B: 30% EtOH 5 min run | 1.4 | 0.27 |
| 2.39.219S.* | (S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclohexyl)-N-methyl-N-(2,2,2-trifluoroethyl)acetamide | 0.89 | 629.20 | Chiralpak IB B: 30% EtOH 5 min run | 1.7 | 0.06 |
| 2.39.220. | N-Cyclobutyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclohexyl)-N-methylacetamide | 0.88 | 601.28 | | | 0.01 |
| 2.39.222. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-(2-fluoro-2-methylpropyl)-2-(1-hydroxycyclohexyl)-N-methylacetamide | 0.90 | 621.29 | | | 0.05 |

TABLE 5-continued

| Example | Name | $t_R$ [min] | $[M + H]^+$ | Chiral HPLC | $t_R$ chiral [min] | $IC_{50}$ [uM] |
|---|---|---|---|---|---|---|
| 2.39.222R. | (R)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-(2-fluoro-2-methylpropyl)-2-(1-hydroxycyclohexyl)-N-methylacetamide | 0.90 | 621.29 | Chiralpak ID B: 25% EtOH 5 min run | 1.91 | 10.2 |
| 2.39.222S. | (S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-(2-fluoro-2-methylpropyl)-2-(1-hydroxycyclohexyl)-N-methylacetamide [1,3-di-deoxy-1-((N-(3-fluoro-3-methylbutyl)-2-(1-hydroxycyclohexyl)-N-methylacetamide)-(S)-thio)-3-[4-(3,4,5-trifluorophenyl)-1H-1,2,3-triazol-1-yl]-β-D-galactopyranoside] | 0.90 | 621.29 | Chiralpak ID B: 25% EtOH 5 min run | 2.3 | 0.02 |
| 2.39.224R.* | (R)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclohexyl)-N-methyl-N-(pyridin-2-ylmethyl)acetamide | 0.80 | 680.22 | Chiralpak ID B: 40% MeCN/ 2-ProOH (1/1) 5 min run | 2.97 | 1.4 |
| 2.39.224S.* | (S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclohexyl)-N-methyl-N-(pyridin-2-ylmethyl)acetamide [1,3-di-deoxy-1-((2-(1-hydroxycyclohexyl)-N-methyl-N-(pyridin-2-yl-methyl)acetamide)-(S)-thio)-3-[4-(3,4,5-trifluorophenyl)-1H-1,2,3-triazol-1-yl]-β-D-galactopyranoside] | 0.80 | 680.22 | Chiralpak ID B: 40% MeCN/ 2-ProOH (1/1) 5 min run | 2.46 | 0.06 |
| 2.44.201. | 2-(4,4-Difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N,N-dimethylacetamide | 0.81 | 596.99 | | | 0.10 |
| 2.44.201R. | 2-(4,4-Difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N,N-dimethylacetamide | 0.81 | 596.99 | Chiralpak AD-H B: 50% EtOH 5 min run | 0.96 | 1.33 |
| 2.44.201S. | 2-(4,4-Difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N,N-dimethylacetamide | 0.81 | 596.99 | Chiralpak AD-H B: 50% EtOH 5 min run | 1.52 | 0.04 |
| 2.44.203. | 2-(4,4-Difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-N-methylacetamide | 0.81 | 575.3 | | | 0.06 |
| 2.44.206R.* | (R)-N-Cyclobutyl-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-methylacetamide | 0.79 | 609.23 | Chiralcel OJH B: 15% MeOH 5 min run | 1.6 | 0.44 |
| 2.44.206S.* | (S)-N-Cyclobutyl-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-methylacetamide | 0.79 | 609.23 | Chiralcel OJH B: 15% MeOH 5 min run | 2.34 | 0.04 |
| 2.44.208. | 2-(4,4-Difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-1-(piperidin-1-yl)ethan-1-one | 0.87 | 601.3 | | | 0.07 |
| 2.44.208R. | (R)-2-(4,4-Difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-1-(piperidin-1-yl)ethan-1-one | 0.87 | 601.3 | Chiralpak AD-H B: 45% EtOH 3 min run | 2.1 | 3.36 |
| 2.44.208S. | (S)-2-(4,4-Difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-1-(piperidin-1-yl)ethan-1-one | 0.87 | 601.3 | Chiralpak AD-H B: 45% EtOH 3 min run | 1.2 | 0.02 |

TABLE 5-continued

| Example | Name | $t_R$ [min] | $[M + H]^+$ | Chiral HPLC | $t_R$ chiral [min] | $IC_{50}$ [uM] |
|---|---|---|---|---|---|---|
| 2.44.218. | N-(Cyclopropylmethyl)-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-methylacetamide | 0.89 | 637.33 | | | 0.02 |
| 2.44.218R. | (R)-N-(Cyclopropylmethyl)-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-methylacetamide | 0.89 | 637.33 | Chiralcel OJ-H B: 15% MeOH 5 min run | 1.52 | 1.15 |
| 2.44.218S. | (S)-N-(Cyclopropylmethyl)-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-methylacetamide | 0.89 | 637.33 | Chiralcel OJ-H B: 15% MeOH 5 min run | 2.19 | 0.05 |
| 2.44.221. | N-Cyclopropyl-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-methylacetamide | 0.86 | 623.17 | | | 0.03 |
| 2.44.222. | 2-(4,4-Difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-(2-fluoro-2-methylpropyl)-N-methylacetamide | 0.90 | 621.29 | | | 0.13 |
| 2.44.223. | 2-(4,4-Difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-((1-fluorocyclopentyl)methyl)-N-methylacetamide | 0.95 | 683.33 | | | 0.05 |
| 2.44.223R. | 2-(4,4-Difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-((1-fluorocyclopentyl)methyl)-N-methylacetamide | 0.95 | 683.33 | Chiralpak AD-H B: 30% 2ProOH 5 min run | 1.99 | 3.57 |
| 2.44.223S. | (S)-2-(4,4-Difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-((1-fluorocyclopentyl)methyl)-N-methylacetamide | 0.95 | 683.33 | Chiralpak AD-H B: 30% 2-ProOH 5 min run | 3.04 | 0.07 |
| 2.44.225. | 2-(4,4-Difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-(3,3-dimethylbutyl)-N-methylacetamide | 0.98 | 667.28 | | | 0.07 |
| 2.44.226. | 2-(4,4-Difluoro-1-hydroxycyclohexyl)-1-(4,4-difluoropiperidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)ethan-1-one | 0.90 | 673.23 | | | 0.09 |
| 2.44.227R.* | (R)-2-(4,4-Difluoro-1-hydroxycyclohexyl)-1-(3,3-difluoroazetidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)ethan-1-one | 0.84 | 646.01 | Chiralcel OJH B: 18% (1/1) ACN/EtOH 3 min run | 1.16 | 1.05 |
| 2.44.227S.* | (S)-2-(4,4-Difluoro-1-hydroxycyclohexyl)-1-(3,3-difluoroazetidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)ethan-1-one | 0.84 | 646.01 | Chiralcel OJH B: 18% (1/1) ACN/EtOH 3 min run | 1.93 | 0.10 |
| 2.38.203. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(1-hydroxycyclopentyl)-N-methylacetamide | 0.77 | 561.31 | | | 0.43 |
| 2.38.206. | 1-(Azetidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclopentyl)ethan-1-one | 0.71 | 559.23 | | | 0.23 |

TABLE 5-continued

| Example | Name | $t_R$ [min] | $[M + H]^+$ | Chiral HPLC | $t_R$ chiral [min] | $IC_{50}$ [uM] |
|---|---|---|---|---|---|---|
| 2.38.219. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclopentyl)-N-methyl-N-(2,2,2-trifluoroethyl)acetamide | 0.86 | 615.18 | | | 0.04 |
| 2.38.220. | N-Cyclobutyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclopentyl)-N-methylacetamide | 0.85 | 587.28 | | | 0.03 |
| 2.38.228. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclopentyl)-N-methyl-N-neopentylacetamide | 0.90 | 603.32 | | | 0.15 |
| 2.34.203. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(1-hydroxycyclobutyl)-N-methylacetamide | 0.73 | 547.22 | | | 0.40 |
| 2.34.203R. | (R)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(1-hydroxycyclobutyl)-N-methylacetamide | 0.73 | 547.22 | Chiralcel OJ-H B: 15% MeOH 2.5 min run | 1.37 | 3.58 |
| 2.34.203S. | (S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(1-hydroxycyclobutyl)-N-methylacetamide | 0.73 | 547.22 | Chiralcel OJ-H B: 15% MeOH 2.5 min run | 1.71 | 0.12 |
| 2.34.206. | 1-(Azetidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)ethan-1-one | 0.70 | 545.2 | | | 1.20 |
| 2.34.206R. | (R)-1-(Azetidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)ethan-1-one | 0.70 | 545.2 | Chiralcel OJ-H B: 15% MeOH 5 min run | 1.57 | 1.8 |
| 2.34.206S. | (S)-1-(Azetidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)ethan-1-one | 0.70 | 545.2 | Chiralcel OJ-H B: 15% MeOH 5 min run | 2.07 | 0.34 |
| 2.34.208. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)-1-(piperidin-1-yl)ethan-1-one | 0.81 | 573.25 | | | 0.38 |
| 2.34.208R. | (R)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)-1-(piperidin-1-yl)ethan-1-one | 0.81 | 573.25 | Chiralcel OJ-H B: 15% MeOH 5 min run | 1.54 | 3.24 |
| 2.34.208S. | (S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)-1-(piperidin-1-yl)ethan-1-one | 0.81 | 573.25 | Chiralcel OJ-H B: 15% MeOH 5 min run | 2.05 | 0.14 |
| 2.34.218. | N-(Cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)-N-methylacetamide | 0.81 | 573.24 | | | 0.31 |
| 2.34.218R. | (R)-N-(Cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)-N-methylacetamide | 0.81 | 573.24 | Chiralpak IB B: 30% EtOH 5 min run | | 6.08 |
| 2.34.218S. | (S)-N-(Cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)-N-methylacetamide [1,3-di-deoxy-1-((2-(3,3-difluoro-1-hydroxycyclobutyl)-N-ethyl-N- | 0.81 | 573.24 | Chiralpak IB B: 30% EtOH 5 min run | | 0.06 |

TABLE 5-continued

| Example | Name | $t_R$ [min] | [M + H]$^+$ | Chiral HPLC | $t_R$ chiral [min] | IC$_{50}$ [uM] |
|---|---|---|---|---|---|---|
| | methylacetamide)-(S)-thio)-3-[4-(3,4,5-trifluorophenyl)-1H-1,2,3-triazol-1-yl]-β-D-galactopyranoside] | | | | | |
| 2.34.219. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)-N-methyl-N-(2,2,2-trifluoroethyl)acetamide | 0.84 | 601.18 | | | 0.26 |
| 2.34.219R. | (R)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)-N-methyl-N-(2,2,2-trifluoroethyl)acetamide | 0.84 | 601.18 | Chiralcel OJ-H B: 15% MeOH 5 min run | 1.23 | 7.84 |
| 2.34.219S. | (S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)-N-methyl-N-(2,2,2-trifluoroethyl)acetamide | 0.84 | 601.18 | Chiralcel OJ-H B: 15% MeOH 5 min run | 1.64 | 0.11 |
| 2.34.222. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-(2-fluoro-2-methylpropyl)-2-(1-hydroxycyclobutyl)-N-methylacetamide | 0.83 | 593.24 | | | 0.41 |
| 2.34.222R. | (R)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-(2-fluoro-2-methylpropyl)-2-(1-hydroxycyclobutyl)-N-methylacetamide | 0.83 | 593.24 | Chiralcel OJ-H B: 10% MeOH 5 min run | 2.56 | 8.61 |
| 2.34.222S. | (S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-(2-fluoro-2-methylpropyl)-2-(1-hydroxycyclobutyl)-N-methylacetamide | 0.83 | 593.24 | Chiralcel OJ-H B: 10% MeOH 5 min run | 3.56 | 0.09 |
| 2.34.228. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)-N-methyl-N-neopentylacetamide | 0.88 | 589.27 | | | 0.31 |
| 2.34.228R. | (R)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)-N-methyl-N-neopentylacetamide | 0.88 | 589.27 | Chiralcel OJ-H B: 15% MeOH 5 min run | 1.23 | 5.9 |
| 2.34.228S. | (S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)-N-methyl-N-neopentylacetamide | 0.88 | 589.27 | Chiralcel OJ-H B: 15% MeOH 5 min run | 1.59 | 0.12 |
| 2.33.203R.* | (R)-2-(3,3-Difluoro-1-hydroxycyclobutyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-N-methylacetamide | 0.79 | 583.26 | Chiralpak ID B: 30% 2-PrOH 5 min run | 1.5 | 1.45 |
| 2.33.203S.* | (S)-2-(3,3-Difluoro-1-hydroxycyclobutyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-N-methylacetamide | 0.79 | 583.26 | Chiralpak ID B: 30% 2-PrOH 5 min run | 2.27 | 0.05 |
| 2.33.206. | 1-(Azetidin-1-yl)-2-(3,3-difluoro-1-hydroxycyclobutyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)ethan-1-one | 0.76 | 581.2 | | | 0.58 |
| 2.33.218R.* | (R)-N-(Cyclopropylmethyl)-2-(3,3-difluoro-1-hydroxycyclobutyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-methylacetamide | 0.85 | 609.21 | Chiralcel OJ-H B: 30% 2-PrOH 5 min run | 1.61 | 0.44 |
| 2.33.218S.* | (S)-N-(Cyclopropylmethyl)-2-(3,3-difluoro-1-hydroxycyclobutyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-methylacetamide | 0.85 | 609.21 | Chiralcel OJ-H B: 30% 2-PrOH 5 min run | 2.62 | 0.04 |

*Epimers are separated during the purification on preparative HPLC/MS(I) or HPLC/MS(II).

Following examples are prepared starting from tert-butyl sulfanyl acetate, the corresponding ketones (Intermediate 7 and analogous) and Intermediate 3, according to the procedures described for Example 2.41.201. LC-MS and Gal-3 inhibition data are listed in Table 6 below. The LC-MS conditions used are LC-MS (A). Chiral analytical HPLC (I) (conditions and retention time) and inhibition data of the epimers R and S of selected examples are also listed.

TABLE 6

| Example | Name | $t_R$ [min] | $[M + H]^+$ | Chiral HPLC | $t_R$ chiral [min] | $IC_{50}$ [uM] |
|---|---|---|---|---|---|---|
| 2.32.203. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N,3-diethyl-3-hydroxy-N-methylpentanamide | 0.82 | 563.25 | | | 0.49 |
| 2.32.203R. | (R)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N,3-diethyl-3-hydroxy-N-methylpentanamide | 0.82 | 563.25 | Chiralcel OJ-H B: 10% MeOH 5 min run | 2.51 | 4.55 |
| 2.32.203S. | (S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N,3-diethyl-3-hydroxy-N-methylpentanamide | 0.82 | 563.25 | Chiralcel OJ-H B: 10% MeOH 5 min run | 3.07 | 0.24 |
| 2.32.218. | N-(Cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-ethyl-3-hydroxy-N-methylpentanamide | 0.87 | 589.31 | | | 0.71 |
| 2.32.222. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-3-ethyl-N-(2-fluoro-2-methylpropyl)-3-hydroxy-N-methylpentanamide | 0.88 | 609.27 | | | 0.36 |
| 2.31.207. | N-Benzyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N,3-dimethylbutanamide | 0.83 | 597.21 | | | 0.06 |
| 2.31.208. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-methyl-1-(piperidin-1-yl)butan-1-one | 0.77 | 561.05 | | | 0.07 |
| 2.31.211R.* | (R)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-methyl-1-(pyrrolidin-1-yl)butan-1-one | 0.71 | 547.21 | Chiralpak IB B: 30% (1/1) MeCN/EtOH 5 min run | 1.76 | 0.31 |
| 2.31.211S* | (S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-methyl-1-(pyrrolidin-1-yl)butan-1-one | 0.71 | 547.21 | Chiralpak IB B: 30% (1/1) MeCN/EtOH 5 min run | 2.2 | 0.08 |
| 2.31.215. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N,3-dimethyl-N-((1-methyl-1H-imidazol-4-yl)methyl)butanamide | 0.61 | 601.21 | | | 0.19 |
| 2.31.218. | N-(Cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N,3-dimethylbutanamide | 0.78 | 561.05 | | | 0.03 |
| 2.31.228. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N,3-dimethyl-N-neopentylbutanamide | 0.84 | 577.08 | | | 0.67 |
| 2.31.229. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N-(2-methoxyethyl)-N,3-dimethylbutanamide | 0.72 | 565.03 | | | 0.11 |

TABLE 6-continued

| Example | Name | $t_R$ [min] | [M + H]$^+$ | Chiral HPLC | $t_R$ chiral [min] | IC$_{50}$ [uM] |
|---|---|---|---|---|---|---|
| 2.31.230. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N,3-dimethyl-N-(2-morpholinoethyl)butanamide | 0.61 | 620.06 | | | 0.11 |

*Epimers are separated during the purification on preparative HPLC/MS(I) or HPLC/MS(II).

Following examples have been prepared starting from tert-butyl sulfanyl acetate, the corresponding aldehydes and Intermediate 3, according to the procedures described for Example 2.41.201. LC-MS and Gal-3 inhibition data are listed in Table 7 below. The LC-MS conditions used are LC-MS (A).

combined organic layer is dried over Na$_2$SO$_4$, filtered and solvent removed in vacuo to give a colorless oil. The crude is purified by preparative HPLC/MS (II) to recover the title compound as a white powder (0.06 g, 92%). LC-MS (A): $t_R$=0.97 min; [M+H]$^+$: 780.18.

TABLE 7

| Example | Name | $t_R$ [min] | [M + H]$^+$ | IC$_{50}$ [uM] |
|---|---|---|---|---|
| 2.60.203. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-3-hydroxy-N-methylpentanamide | 0.72 | 535.21 | 0.17 |
| 2.60.206. | 1-(Azetidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxypentan-1-one | 0.68 | 533.12 | 0.50 |
| 2.60.218. | N-(Cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N-methylpentanamide | 0.78 | 561.27 | 0.12 |
| 2.64.203. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-3-hydroxy-N-methyl-4-phenylbutanamide | 0.84 | 598.02 | 0.22 |
| 2.64.206. | 1-(Azetidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-4-phenylbutan-1-one | 0.79 | 595.22 | 0.71 |
| 2.64.218. | N-(Cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N-methyl-4-phenylbutanamide | 0.89 | 623.24 | 0.11 |
| 2.65.203. | 2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-3-hydroxy-N-methyl-3-(1-methyl-1H-pyrazol-3-yl)propanamide | 0.68 | 587.26 | 0.65 |
| 2.65.206. | 1-(Azetidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-(1-methyl-1H-pyrazol-3-yl)propan-1-one | 0.66 | 585.23 | 1.04 |
| 2.65.218. | N-(cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N-methyl-3-(1-methyl-1H-pyrazol-3-yl)propanamide | 0.74 | 613.32 | 0.69 |

Example 2.47.203

2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxy-1-(methylsulfonyl)piperidin-4-yl)-N-methylacetamide (2R,3R,4S,5R,6S)-2-(Acetoxymethyl)-6-((2-(ethyl(methyl)amino)-1-(4-hydroxy-1-(methylsulfonyl)piperidin-4-yl)-2-oxoethyl)thio)-4-(4-(3,4,5-trifluorophenyl)-1H-1,2,3-triazol-1-yl)tetrahydro-2H-pyran-3,5-diyl diacetate To a solution of Intermediate 10 (0.06 g, 0.1 mmol) in DCM (3.0 mL) at rt are added methanesulfonyl chloride (0.007 mL, 1.2 eq) and DIPEA (0.041 mL, 0.17 mmol, 3.0 eq). The reaction mixture is stirred at rt for 2 h, then partitioned between DCM and water. The layers are separated, the aqueous layer is extracted with DCM (3×). The 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxy-1-(methylsulfonyl)piperidin-4-yl)-N-methylacetamide (2.47203.)

K$_2$CO$_3$ (0.001 g, 0.2 eq) is added to a solution of (2R,3R,4S,5R,6S)-2-(acetoxymethyl)-6-(((2-(ethyl(methyl)amino)-1-(4-hydroxy-1-(methylsulfonyl)piperidin-4-yl)-2-oxoethypthio)-4-(4-(3,4,5-trifluorophenyl)-1H-1,2,3-triazol-1-yl)tetrahydro-2H-pyran-3,5-diyl diacetate (0.03 g, 0.04 mmol) in MeOH (1.5 mL) at rt. The reaction mixture is stirred at rt over 17 h, then partitioned between MeCN and water. The mixture is directly purified by preparative HPLC/MS(II) to recover the title compound as a beige powder (0.024 g, 97%). LC-MS (A): $t_R$=0.74 min; [M+H]$^+$: 653.97. $^1$H NMR (400 MHz, MeOD) δ: 8.56 (m, 1H), 7.65 (m, 2H), 4.9-4.75 (m, 2H), 4.28-4.16 (m, 2H), 4.13 (m, 1H), 3.9-3.71 (m, 3H), 3.65-3.55 (m, 3H), 3.55-3.45 (m, 1H), 3.28 (s, 0.8H), 3.24 (s, 1.2H), 3.15-3.05 (m, 1H), 3.0 (s, 0.5H), 2.97

(s, 0.5H), 2.86 (s, 3H), 2.35-2.23 (m, 1H), 2.4-1.9 (m, 1H), 1.82-1.7 (m, 2H), 1.3 (m, 1.3 H), 1.15 (m, 1.8 H).

Example 2.47.203R (R)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxy-1-(methylsulfonyl)piperidin-4-yl)-N-methylacetamide Separation of the epimers of Example 2.47.203. (0.024 g) by chiral preparative HPLC (V) yielded the title compound (0.008 g) as a beige powder. Chiral analytical HPLC (J): $t_R$=2.66 min.

Example 2.47.203S 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxy-1-(methylsulfonyl)piperidin-4-yl)-N-methylacetamide Separation of the epimers of Example 2.47.203. (0.024 g) by chiral preparative HPLC (V) yielded the title compound (0.008 g) as a beige powder. Chiral analytical HPLC (J): $t_R$=3.52 min.

Following examples have been prepared starting from Intermediate 10, Intermediate 10AR, Intermediate 10AS, Intermediate 10I and the corresponding sulfonylchlorides, carbamoyl chloride and isocyanate in analogy to Example 2.47.203. LC-MS and Gal-3 inhibition data are listed in Table 8 below. The LC-MS conditions used are LC-MS (A). Chiral analytical HPLC (I) (conditions and retention time) and inhibition data of the epimers R and S of selected examples are also listed.

TABLE 8

| Example | Name | $t_R$ [min] | [M + H]$^+$ | Chiral HPLC | $t_R$ chiral [min] | IC$_{50}$ [uM] |
|---|---|---|---|---|---|---|
| 2.47.203. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxy-1-(methylsulfonyl)piperidin-4-yl)-N-methylacetamide | 0.74 | 653.97 | | | 0.03 |
| 2.47.203R. | (R)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxy-1-(methylsulfonyl)piperidin-4-yl)-N-methylacetamide | 0.74 | 653.97 | Chiralpak IH B: 20% MeCN/EtOH (1/1) 5 min run | 2.69 | 6.77 |
| 2.47.203S. | (S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxy-1-(methylsulfonyl)piperidin-4-yl)-N-methylacetamide | 0.74 | 653.97 | Chiralpak IH B: 20% MeCN/EtOH (1/1) 5 min run | 3.52 | 0.01 |
| 2.51.203. | 2-(1-(Cyclopropylsulfonyl)-4-hydroxypiperidin-4-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-N-methylacetamide | 0.78 | 680.19 | | | 0.03 |
| 2.51.203R. | (R)-2-(1-(Cyclopropylsulfonyl)-4-hydroxypiperidin-4-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-N-methylacetamide | 0.78 | 680.19 | Chiralcel OJ-H B: 25% MeOH 5 min run | 1.31 | 4.96 |
| 2.51.203S. | (S)-2-(1-(Cyclopropylsulfonyl)-4-hydroxypiperidin-4-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-N-methylacetamide [1,3-di-deoxy-1-((2-(1-(cyclopropylsulfonyl)-4-hydroxypiperidin-4-yl)-N-ethyl-N-methylacetamide)-(S)-thio)-3-[4-(3,4,5-trifluorophenyl)-1H-1,2,3-triazol-1-yl]-β-D-galactopyranoside] | 0.78 | 680.19 | Chiralcel OJ-H B: 25% MeOH 5 min run | 2.14 | 0.02 |
| 2.49.203. | N-Cyclopropyl-4-(1-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(ethyl(methyl)amino)-2-oxoethyl)-4-hydroxypiperidine-1-carboxamide | 0.71 | 659.25 | | | 0.05 |
| 2.49.203R. | (R)-N-Cyclopropyl-4-(1-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(ethyl(methyl)amino)-2-oxoethyl)-4-hydroxypiperidine-1-carboxamide | 0.71 | 659.25 | Chiralcel OJ-H B: 15% MeOH 5 min run | 1.57 | 2.65 |

TABLE 8-continued

| Example | Name | $t_R$ [min] | $[M + H]^+$ | Chiral HPLC | $t_R$ chiral [min] | $IC_{50}$ [uM] |
|---|---|---|---|---|---|---|
| 2.49.203S. | (S)-N-Cyclopropyl-4-(1-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(ethyl(methyl)amino)-2-oxoethyl)-4-hydroxypiperidine-1-carboxamide | 0.71 | 659.25 | Chiralcel OJ-H B: 15% MeOH 5 min run | 2.04 | 0.04 |
| 2.50.203. | Methyl 4-(1-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(ethyl(methyl)amino)-2-oxoethyl)-4-hydroxypiperidine-1-carboxylate | 0.76 | 634.26 | | | 0.07 |
| 2.50.203R. | (R)-Methyl 4-(1-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(ethyl(methyl)amino)-2-oxoethyl)-4-hydroxypiperidine-1-carboxylate | 0.76 | 634.26 | Chiralcel OJ-H B: 15% MeOH 5 min run | 1.14 | 4.45 |
| 2.50.203S. | (S)-Methyl 4-(1-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(ethyl(methyl)amino)-2-oxoethyl)-4-hydroxypiperidine-1-carboxylate | 0.76 | 634.26 | Chiralcel OJ-H B: 15% MeOH 5 min run | 1.98 | 0.04 |
| 2.58.203R. | (2R,3R,4S,5R,6S)-2-(Acetoxymethyl)-6-(((R)-2-(ethyl(methyl)amino)-1-(3-hydroxy-1-(methoxycarbonyl)azetidin-3-yl)-2-oxoethyl)thio)-4-(4-(3,4,5-trifluorophenyl)-1H-1,2,3-triazol-1-yl)tetrahydro-2H-pyran-3,5-diyl diacetate | 0.71 | 606.23 | Chiralpak IC B: 35% (1/1) MeCN/EtOH 5 min run | 3.1 | 0.45 |
| 2.58.203S. | (2R,3R,4S,5R,6S)-2-(Acetoxymethyl)-6-(((S)-2-(ethyl(methyl)amino)-1-(3-hydroxy-1-(methoxycarbonyl)azetidin-3-yl)-2-oxoethyl)thio)-4-(4-(3,4,5-trifluorophenyl)-1H-1,2,3-triazol-1-yl)tetrahydro-2H-pyran-3,5-diyl diacetate | 0.71 | 606.19 | Chiralpak IC B: 35% (1/1) MeCN/EtOH 5 min run | 2.13 | 0.03 |
| 2.49.226.I. | N-Cyclopropyl-4-(2-(ethyl(methyl)amino)-1-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-oxoethyl)-4-hydroxypiperidine-1-carboxamide | 0.87 | 735.16 | | | 0.1 |
| 2.49.226R.I. | N-Cyclopropyl-4-((R)-2-(ethyl(methyl)amino)-1-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-oxoethyl)-4-hydroxypiperidine-1-carboxamide | | | Chiralpak IB B: 25% (1/1) MeCN/EtOH 5 min run | 2.8 | 1.74 |
| 2.49.226S.I. | N-Cyclopropyl-4-((S)-2-(ethyl(methyl)amino)-1-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-oxoethyl)-4-hydroxypiperidine-1-carboxamide | | | Chiralpak IB B: 25% (1/1) MeCN/EtOH 5 min run | 2.33 | 0.06 |

Example 2.41.232

2R,3R,4S,5R,6S)-2-(Acetoxymethyl)-6-((2-(ethyl(phenyl)amino)-1-(4-hydroxytetrahydro-2H-pyran-4-yl)-2-oxoethyl)thio)-4-(4-(3,4,5-trifluorophenyl)-1H-1,2,3-triazol-1-yl)tetra hydro-2H-pyran-3,5-diyl diacetate 1. N-Ethyl-N-phenyl-2-((tetrahydro-2H-pyran-2-yl)thio)acetamide N-Ethyl-N-phenyl-2-((tetrahydro-2H-pyran-2-yl)thio)acetamide is prepared from 3,4-dihydro-2H-pyran, ethyl thioglycolate, N-ethyl aniline and tetrahydro-4H-pyran-4-one according to the procedures described for Intermediate 12 as a beige oil. LC-MS (A): $t_R$=0.81; $[M+H]^+$: 296.15.

2. (2R,3R,4S,5R,6S)-2-(Acetoxymethyl)-6-((2-(ethyl(phenyl)amino)-1-(4-hydroxytetrahydro-2H-pyran-4-yl)-2-oxoethyl)thio)-4-(4-(3,4,5-trifluorophenyl)-1H-1,2,3-triazol-1-yl)tetrahydro-2H-pyran-3,5-diyl diacetate To a solution of N-ethyl-2-(4-hydroxytetrahydro-2H-pyran-4-yl)-2-mercapto-N-phenylacetamide (0.09 g, 0.3 mmol) in aq. 10% $Na_2CO_3$ (2.0 mL) is added TBAHS (0.62 g, 1.78 mmol, 6.0 eq). To this mixture is added Intermediate 3 (0.22 g, 1.2 mmol, 1.2 eq in EA (4.0 mL) and the mixture is stirred at rt for 15 h, diluted with EA (25.0 mL), water (25.0 mL), and brine (25.0 mL). The phases are separated and the aq. layer is extracted with EA (50.0 mL). The combined organic phase is dried over $Na_2SO_4$, filtered and solvent removed in vacuo. The residue is purified by preparative HPLC/MS (I) to recover the title compound as a beige powder. (0.06 g, 24%). LC-MS (A): $t_R$=1.05 min; [M+H]⁺: 765.17.

3. 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxytetrahydro-2H-pyran-4-yl)-N-phenylacetamide (2.41.232.)

K₂CO₃ (0.002 g, 0.014 mmol, 0.2 eq) is added at rt to a solution of (2R,3R,4S,5R,6S)-2-(acetoxymethyl)-6-((2-(ethyl(phenyl)amino)-1-(4-hydroxytetrahydro-2H-pyran-4-yl)-2-oxoethypthio)-4-(4-(3,4,5-trifluorophenyl)-1H-1,2,3-triazol-1-yl)tetrahydro-2H-pyran-3,5-diyl diacetate (0.055 g, 0.07 mmol) in MeOH (2.0 mL). The reaction mixture is stirred at rt for 15 h, quenched with MeCN, followed by water and the mixture is directly purified by preparative HPLC/MS (I) to recover the title compound as a beige solid (0.040 g, 87%). LC-MS (A): $t_R$=0.83 min; [M+H]⁺: 639.15. ¹H NMR (400 MHz, MeOD) δ: 8.51-8.62 (m, 1H), 7.39-7.73 (m, 7H), 4.75-4.82 (m, 1H), 4.55-4.68 (m, 0H), 4.33-4.41 (m, 1H), 4.05-4.27 (m, 2H), 3.83-4.00 (m, 1H), 3.65-3.80 (m, 6H), 3.55-3.65 (m, 1H), 3.40-3.54 (m, 2H), 1.48-2.21 (m, 4H), 1.08-1.26 (m, 3H).

Following aryl/heteroaryl amides have been prepared starting from the corresponding 2-mercapto acetamides (prepared in analogy to Intermediate 12) and Intermediate 2 or Intermediate 14 in analogy to Example 2.41.232. LC-MS and Gal-3 inhibition data are listed in Table 9 below. The LC-MS conditions used are LC-MS (A). Chiral HPLC (conditions and retention time) and inhibition data of the epimers R and S of selected Examples are also listed.

TABLE 9

| Example | Name | $t_R$ | [M + H]⁺ | HPLC conditions | $t_R$ chiral | IC₅₀ [uM] |
|---|---|---|---|---|---|---|
| 2.41.232. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxytetrahydro-2H-pyran-4-yl)-N-phenylacetamide | 0.83 | 639.15 | | | 0.09 |
| 2.41.231. | 2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-phenylacetamide | 0.79 | 625.06 | | | 0.11 |
| 2.41.231R. | (R)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-phenylacetamide | 0.80 | 625.93 | Chiralpak ID B: 25% (1/1) MeCN/EtOH 5 min run | 3.26 | 3.44 |
| 2.41.231S. | (S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-phenylacetamide | 0.81 | 625.91 | Chiralpak ID B: 25% (1/1) MeCN/EtOH 5 min run | 4.03 | 0.07 |
| 2.41.233R. | (R)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(pyridin-2-yl)acetamide | 0.71 | 625.98 | Chiralcel OZ-H B: 40% (1/1) MeCN/EtOH 5 min run | 3.86 | 8.5 |
| 2.41.233S. | (S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(pyridin-2-yl)acetamide | 0.72 | 625.97 | Chiralcel OZ-H B: 40% (1/1) MeCN/EtOH 5 min run | 2.27 | 0.04 |
| 2.41.234R | (R)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(pyridin-3-yl)acetamide | 0.64 | 625.98 | Chiralpak IH B: 25% (1/1) MeCN/EtOH 5 min run | 1.67 | 7.8 |
| 2.41.234S. | (S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(pyridin-3-yl)acetamide | 0.65 | 625.98 | Chiralpak IH B: 25% (1/1) MeCN/EtOH 5 min run | 3.8 | 0.1 |

TABLE 9-continued

| Example | Name | $t_R$ | $[M + H]^+$ | HPLC conditions | $t_R$ chiral | IC$_{50}$ [uM] |
|---|---|---|---|---|---|---|
| 2.41.233R.I. | (R)-2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methyl-N-(pyridin-2-yl)acetamide | 0.94 | 674.18 | Chiralpak IE B: 30% (1/1) MeCN/2-PrOH 5 min run | 2.14 | 7.24 |
| 2.41.233S.I. | (S)-2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methyl-N-(pyridin-2-yl)acetamide [1,3-di-deoxy-1-((2-(4,4-difluoro-1-hydroxycyclohexyl)-N-methyl-N-(pyridin-2-yl)acetamide)-(S)-thio)-2-O-methyl-3-[4-(3,4,5-trifluorophenyl)-1H-1,2,3-triazol-1-yl]-b-D-galactopyranoside] | 0.94 | 674.21 | Chiralpak IE B: 30% (1/1) MeCN/2-PrOH 5 min run | 1.69 | 0.05 |

Following examples are prepared starting from the corresponding 2-mercapto acetamides (prepared in analogy to Intermediate 12) and Intermediate 2 or Intermediate 14 in analogy to Example 2.41.232. LC-MS and Gal-3 inhibition data are listed in Table 10 below. The LC-MS conditions used are LC-MS (A). Chiral HPLC (conditions and retention time) and inhibition data of the epimers R and S of selected Examples are also listed.

TABLE 10

| Example | Name | $t_R$ | $[M + H]^+$ | HPLC conditions | $t_R$ chiral | IC$_{50}$ [uM] |
|---|---|---|---|---|---|---|
| 2.41.237. | N-Cyclobutyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxytetrahydro-2H-pyran-4-yl)acetamide | 0.80 | 617.21 | | | 0.03 |
| 2.41.220. | N-Cyclobutyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methylacetamide | 0.77 | 603.19 | | | 0.05 |
| 2.44.238.I. | N-Cyclopropyl-2-(4,4-difluoro-1-hydroxycyclohexyl)-N-ethyl-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide | 0.99 | 651.22 | | | 0.04 |
| 2.44.238R.I. | (R)-N-Cyclopropyl-2-(4,4-difluoro-1-hydroxycyclohexyl)-N-ethyl-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide | 1.0 | 651.13 | Chiralcel OZ-H B: 35% (1/1) MeCN/EtOH 5 min run | 1.89 | 1.0 |
| 2.44.238S.I. | (S)-N-Cyclopropyl-2-(4,4-difluoro-1-hydroxycyclohexyl)-N-ethyl-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide [1,3-di-deoxy-1-((2-(4,4-difluoro-1-hydroxycyclohexyl)-(N-(cyclopropyl))-N-ethylacetamide)-(S)-thio)-2-O-methyl-3-[4-(3,4,5-trifluorophenyl)-1H-1,2,3-triazol-1-yl]-b-D-galactopyranoside] | 1.0 | 651.14 | Chiralcel OZ-H B: 35% (1/1) MeCN/EtOH 5 min run | 2.68 | 0.02 |

TABLE 10-continued

| Example | Name | $t_R$ | $[M + H]^+$ | HPLC conditions | $t_R$ chiral | $IC_{50}$ [uM] |
|---|---|---|---|---|---|---|
| 2.44.239.I. | N-(Cyclopropylmethyl)-2-(4,4-difluoro-1-hydroxycyclohexyl)-N-ethyl-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide | 1.00 | 665.16 | | | 0.04 |
| 2.44.214.I. | 2-(4,4-Difluoro-1-hydroxycyclohexyl)-N-ethyl-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-((tetrahydro-2H-pyran-4-yl)methyl)acetamide | 0.96 | 710 | | | 0.03 |
| 2.44.240.I. | N-Benzyl-2-(4,4-difluoro-1-hydroxycyclohexyl)-N-ethyl-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide | 1.04 | 701.17 | | | 0.04 |
| 2.44.256.I. | 2-(4,4-Difluoro-1-hydroxycyclohexyl)-N-((3,3-difluorocyclobutyl)methyl)-N-ethyl-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide | 1.05 | 715.13 | | | 0.05 |
| 2.44.257.I. | 2-(4,4-Difluoro-1-hydroxycyclohexyl)-N-ethyl-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-(tetrahydro-2H-pyran-4-yl)acetamide | 0.97 | 695.14 | | | 0.07 |

Example 10.41.203

2-(((2S,3R,4S,5R,6R)-4-(4-(3,5-Difluorophenyl)-1H-1,2,3-triazol-1-yl)-3,5-dihydroxy-6-(hydroxymethyl)tetrahydro-2H-Pyran-2-yl)thio)-N-ethyl-2-(4-hydroxytetrahydro-2H-pyran-4-yl)-N-methylacetamide 1. (2R,3R,4S,5R,6S)-2-(Acetoxymethyl)-4-(4-(3,5-difluorophenyl)-1H-1,2,3-triazol-1-yl)-6-((2-(ethyl(methyl)amino)-1-(4-hydroxytetrahydro-2H-pyran-4-yl)-2-oxoethyl)thio)tetrahydro-2H-pyran-3,5-diyl diacetate To a solution of Intermediate 13 (0.05 g, 0.10 mmol) in DMF (2.0 mL) are added 1-ethynyl-3,5-difluorobenzene (0.02 g, 0.15 mmol, 1.5 eq), CuI (0.006 g, 0.03 mmol, 0.3 eq) and DIPEA (0.05 mL, 0.30 mmol, 3.0 eq). The reaction mixture is stirred at 43° C. for 1 h, then cooled to rt, diluted with EA and filtered. The org. layer is washed with aq. sat. NH$_4$Cl, brine, dried over Na$_2$SO$_4$, filtered and solvent removed in vacuo. The resulting crude is purified by preparative HPLC/MS (I) to give the title compound as a beige solid (0.06 g, 90%). LC-MS (A): $t_R$=0.93 min; [M+H]$^+$: 685.18.

2. 2-(((2S,3R,4S,5R,6R)-4-(4-(3,5-Difluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide (10.41.203.)

To a solution of 2R,3R,4S,5R,6S)-2-(acetoxymethyl)-4-(4-(3,5-difluorophenyl)-1H-1,2,3-triazol-1-yl)-6-((2-(ethyl(methyl)amino)-1-(4-hydroxytetrahydro-2H-pyran-4-yl)-2-oxoethypthio)tetrahydro-2H-pyran-3,5-diyl diacetate (0.06 g, 0.09 mmol, 1.0 eq) in MeOH (3.0 mL) is added K$_2$CO$_3$ (0.003 g, 0.02 mmol, 0.2 eq). The reaction mixture is stirred at rt for 3 h, acetonitrile is added, followed by water and the mixture is directly purified by preparative HPLC/MS (I) to give the title product as a beige solid (0.05 g, 91%). LC-MS (A): $t_R$=0.67 min; [M+H]$^+$: 559.22.

Following examples are prepared starting from Intermediate 13 or a close analogue and the corresponding alkynes according to the procedures described for Example 10.41.203. LC-MS and Gal-3 inhibition data are listed in Table 11 below. The LC-MS conditions used are LC-MS (A). Chiral HPLC (conditions and retention time) and inhibition data of the epimers R and S of selected Examples are also listed.

TABLE 11

| Example | Name | $t_R$ | $[M + H]^+$ | HPLC conditions | $t_R$ chiral | $IC_{50}$ [uM] |
|---|---|---|---|---|---|---|
| 10.41.203. | 2-(((2S,3R,4S,5R,6R)-4-(4-(3,5-Difluorophenyl)-1H-1,2,3-triazol-1-yl)-3,5-dihydroxy-6- | 0.67 | 559.22 | | | 0.10 |

TABLE 11-continued

| Example | Name | $t_R$ | $[M + H]^+$ | HPLC conditions | $t_R$ chiral | IC$_{50}$ [uM] |
|---|---|---|---|---|---|---|
| 1.41.203. | (hydroxymethyl)tetrahydro-2H-pyran-2-yl)thio)-N-ethyl-2-(4-hydroxytetrahydro-2H-pyran-4-yl)-N-methylacetamide N-Ethyl-2-(((2S,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)thio)-2-(4-hydroxytetrahydro-2H-pyran-4-yl)-N-methylacetamide | 0.63 | 541.15 | | | 0.13 |
| 3.41.203. | 2-(((2S,3R,4S,5R,6R)-4-(4-(3,5-Difluoro-4-methylphenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide | 0.72 | 573.22 | | | 0.04 |
| 11.41.203. | 2-(((2S,3R,4S,5R,6R)-4-(4-(4-Chloro-3,5-difluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide | 0.74 | 593.17 | | | 0.03 |
| 14.41.203. | 2-(((2S,3R,4S,5R,6R)-4-(4-(4-Bromothiazol-2-yl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide | 0.63 | 610.07 | | | 0.15 |
| 12.41.203. | 2-(((2S,3R,4S,5R,6R)-4-(4-(4-Bromo-3-fluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide | 0.72 | 621.17 | | | 0.04 |
| 13.41.203. | 2-(((2S,3R,4S,5R,6R)-4-(4-(3-Chloro-5-fluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide | 0.71 | 575.33 | | | 0.08 |
| 15.41.203. | 2-(((2S,3R,4S,5R,6R)-4-(4-(3-Chloro-4,5-difluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide | 0.73 | 593.33 | | | 0.06 |
| 16.41.203. | 2-(((2S,3R,4S,5R,6R)-4-(4-(3,4-Difluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide | 0.67 | 559.21 | | | 0.06 |
| 17.41.203. | 2-(((2S,3R,4S,5R,6R)-4-(4-(3,4-Dichloro-5-fluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide | 0.77 | 609.17 | | | 0.04 |
| 18.41.203. | 2-(((2S,3R,4S,5R,6R)-4-(4-(4-Bromo-3,5-difluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide | 0.74 | 639.04 | | | 0.04 |
| 19.41.203. | 2-(((2S,3R,4S,5R,6R)-4-(4-(3-Cyano-5-methylphenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide | 0.67 | 562.28 | | | 0.15 |
| 20.41.203. | N-ethyl-2-(((2S,3R,4S,5R,6R)-4-(4-(3-Fluoro-5-methylphenyl)-1H-1,2,3-triazol-1-yl)-3,5-dihydroxy-6-(hydroxymethyl)tetrahydro-2H-pyran-2-yl)thio)-2-(4-hydroxytetrahydro-2H-pyran-4-yl)-N-methylacetamide | 0.69 | 555.25 | | | 0.06 |

TABLE 11-continued

| Example | Name | $t_R$ | [M + H]⁺ | HPLC conditions | $t_R$ chiral | IC$_{50}$ [uM] |
|---|---|---|---|---|---|---|
| 21.44.221R*. | (R)-N-Cyclopropyl-2-(4,4-difluoro-1-hydroxycyclohexyl)-2-(((2S,3R,4S,5R,6R)-4-(4-(6-fluoro-5-methylpyridin-3-yl)-1H-1,2,3-triazol-1-yl)-3,5-dihydroxy-6-(hydroxymethyl)tetrahydro-2H-pyran-2-yl)thio)-N-methylacetamide | 0.77 | 602.18 | | | 0.23 |
| 21.44.221S*. | (S)-N-Cyclopropyl-2-(4,4-difluoro-1-hydroxycyclohexyl)-2-(((2S,3R,4S,5R,6R)-4-(4-(6-fluoro-5-methylpyridin-3-yl)-1H-1,2,3-triazol-1-yl)-3,5-dihydroxy-6-(hydroxymethyl)tetrahydro-2H-pyran-2-yl)thio)-N-methylacetamide | 0.78 | 602.17 | | | 0.05 |

*Epimers are separated during the purification on preparative HPLC/MS(I).

Example 2.44.222.1

2-(4,4-Difluoro-1-hydroxycyclohexyl)-N-(2-fluoro-2-methylpropyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetra hydro-2H-pyran-2-yl)thio)-N-methylacetamide 1. tert-Butyl 2-(4,4-difluoro-1-hydroxycyclohexyl)-2-mercaptoacetate tert-Butyl 2-(4,4-difluoro-1-hydroxycyclohexyl)-2-mercaptoacetate is synthesized from tert-butyl 2-sulfanylacetate and 4,4-difluorocyclohexan-1-one as a white solid in analogy to Intermediate 7. LC-MS(A) $t_R$=0.94 min, [M+H]⁺: 283.17.

2. tert-Butyl 2-(((2S,3R,4S,5R,6R)-5-acetoxy-6-(acetoxymethyl)-3-methoxy-4-(4-(3,4,5-trifluorophenyl)-1H-1,2,3-triazol-1-yl)tetrahydro-2H-pyran-2-yl)thio)-2-(4,4-difluoro-1-hydroxycyclohexyl)acetate To a solution of tert-butyl 2-(4,4-difluoro-1-hydroxycyclohexyl)-2-mercaptoacetate (0.12 g, 0.43 mmol,) in aq.10% Na₂CO₃ (4.0 mL) is added TBAHS (0.89 g, 2.55 mmol, 6.0 eq), followed by a solution of Intermediate 14 (0.63 g, 0.50 mmol, 1.2 eq) in EA (10.0 mL). The reaction mixture is stirred at rt for 2 h, diluted with EA, water and brine and the phases are separated. The aq. layer is extracted with EA, the combined organic phase is dried over Na₂SO₄, filtered and solvent removed in vacuo to give a solid. Purification by preparative HPLC/MS (II) yielded the expected product as a white solid (0.22 g, 71%). LC-MS(A) $t_R$=1.13 min, [M+H]⁺: 724.21.

3. 2-(((2S,3R,4S,5R,6R)-5-Acetoxy-6-(acetoxymethyl)-3-m ethoxy-4-(4-(3,4,5-trifluorophenyl)-1H-1,2,3-triazol-1-yl)tetrahydro-2H-pyran-2-yl)thio)-2-(4,4-difluoro-1-hydroxycyclohexyl) acetic acid To a solution of tert-butyl 2-(((2S,3R,4S,5R,6R)-5-acetoxy-6-(acetoxymethyl)-3-methoxy-4-(4-(3,4,5-trifluorophenyl)-1H-1,2,3-triazol-1-yl)tetrahydro-2H-pyran-2-yl)thio)-2-(4,4-difluoro-1-hydroxycyclohexyl)acetate (0.22 g, 0.30 mmol) in DCM (8.0 mL) is added TFA (0.39 mL, 5.11 mmol, 17.0 eq), the reaction mixture is stirred at rt for 20 h. The mixture is neutralized with aq. 2M NaOH, diluted with DCM and the layers are separated. The aqueous layer is extracted with DCM (3×) and the combined organic layer is dried over Na₂SO₄, filtered and solvent removed in vacuo to recover the title product as a beige powder (0.14 g, 68%), that is not further purified. LC-MS(A) $t_R$=0.97 min, [M+H]⁺: 668.15.

4. ((2R,3R,4S,5R,6S)-3-Acetoxy-6-((1-(4,4-difluoro-1-hydroxycyclohexyl)-2-((2-fluoro-2-methylpropyl)(methyl)amino)-2-oxoethyl)thio)-5-methoxy-4-(4-(3,4,5-trifluorophenyl)-1H-1,2,3-triazol-1-yl) tetrahydro-2H-pyran-2-yl)methyl acetate To a solution of 2-(((2S,3R,4S,5R,6R)-5-acetoxy-6-(acetoxymethyl)-3-methoxy-4-(4-(3,4,5-trifluorophenyl)-1H-1,2,3-triazol-1-yl)tetrahydro-2H-pyran-2-yl)thio)-2-(4,4-difluoro-1-hydroxycyclohexyl)acetic acid (0.45 g, 0.58 mmol) in DMF (20.0 mL) is added HATU (0.25 g, 0.616 mmol, 1.05 eq), followed by a solution of 2-fluoro-N,2-dimethylpropan-1-amine HCl salt (0.1 g, 0.7 mmol, 1.2 eq) and DIPEA (0.27 mL, 1.58 mmol, 2.7 eq) in DMF (2.0 mL). The mixture is stirred at rt for 72 h, filtered and directly purified by preparative HPLC/MS (I) to give the title compound as a beige solid (0.14 g, 32%). LC-MS(A) $t_R$=1.10 min, [M+H]⁺: 755.23.

5. 2-(4,4-Difluoro-1-hydroxycyclohexyl)-N-(2-fluoro-2-methylpropyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide (2.44.222.1.)

To a solution of ((2R,3R,4S,5R,6S)-3-acetoxy-6-((1-(4,4-difluoro-1-hydroxycyclohexyl)-2-((2-fluoro-2-methylpropyl)(methyl)amino)-2-oxoethypthio)-5-methoxy-4-(4-(3,4,5-trifluorophenyl)-1H-1,2,3-triazol-1-yl)tetrahydro-2H-pyran-2-yl)methyl acetate (0.142 g, 0.094 mmol) in MeOH (7.0 mL) is added K₂CO₃ (0.003 g, 0.02 mmol, 0.2 eq). After 2 h stirring at rt, the reaction mixture is diluted with MeCN, followed by water and directly purified by preparative HPLC/MS (I) to give the title compound as a beige solid (0.055 g, 88%). LC-MS(A) $t_R$=0.99 min, [M+H]⁺: 671.42.

Example 2.44.222R.I (R)-2-(4,4-Difluoro-1-hydroxycyclohexyl)-N-(2-fluoro-2-methylpropyl)-2-(((2S,3R,4S,5R,6R)-5-hydroxy-6-(hydroxymethyl)-3-methoxy-4-(4-(3,4,5-trifluorophenyl)-1H-

1,2,3-triazol-1-yl)tetrahydro-2H-pyran-2-yl)thio)-N-methylacetamide[1,3-di-deoxy-1-(((2-(4,4-difluoro-1-hydroxycyclohexyl)-(N-(3-fluoro-3-methylbutyl)-N-methylacetamide)-(R)-thio)-2-O-methyl-3-[4-(3,4,5-trifluorophenyl)-1H-1,2,3-triazol-1-yl]-b-D-dalactopyranoside]

Separation of the epimers of Example 2.44.222.1. (0.055 g) by chiral preparative HPLC (VI) yielded the title compound (0.024 g) as a white solid. Chiral analytical HPLC (K): $t_R$=1.62 min.

Example 2.44.222S.I

S)-2-(4,4-Difluoro-1-hydroxycyclohexyl)-N-(2-fluoro-2-m ethylpropyl)-24(2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide[1,3-di-deoxy-1-((2-(4,4-difluoro-1-hydroxycyclohexyl)-(N-(3-fluoro-3-methylbutyl)-N-methylacetamide)-(S)-thio)-2-O-methyl-3-[4-(3,4,5-trifluorophenyl)-1H-1,2,3-triazol-1-yl]b-D-dalactopyranoside]

Separation of the epimers of Example 2.44.222.1. (0.055 g) by chiral preparative HPLC (VI) yielded the title compound (0.016 g) as a white solid. Chiral analytical HPLC (K): $t_R$=2.24 min. $^1$H NMR (400 MHz, MeOD) δ: 8.68 (s, 0.8H), 8.66 (s, 0.2H), 7.68 (m, 2H), 4.95 (dd, $J_1$=10.8 Hz, $J_2$=3.3 Hz, 1H),), 4.85 (d, J=9.5 Hz, 1H), 4.3 (s, 1H), 4.1 (d, J=2.3 Hz, 1H), 4.0-3.93 (m, 1H), 3.85-3.6 (m, 5H), 3.7 (s, 0.8H), 3.5 (s, 2.3H), 3.55 (s, 3H) 2.4-1.7 (m, 8H), 1.5-1.3 (m, 6H).

Following examples are prepared starting from 2-(((2S,3R,4S,5R,6R)-5-acetoxy-6-(acetoxymethyl)-3-methoxy-4-(4-(3,4,5-trifluorophenyl)-1H-1,2,3-triazol-1-yl)tetrahydro-2H-pyran-2-yl)thio)-2-(4,4-difluoro-1-hydroxycyclohexyl) acetic acid (Example 2.44.222.1. Step 3.) and the corresponding secondary and primary amines according to the procedures described for Example 2.44.222.1. LC-MS and Gal-3 inhibition data are listed in Table 12 below. The LC-MS conditions used were LC-MS (A). Chiral analytical HPLC (I) (conditions and retention time) and inhibition data of the epimers R and S of selected Examples are also listed.

TABLE 12

| Example | Name | $t_R$ | $[M + H]^+$ | HPLC conditions | $t_R$ chiral | $IC_{50}$ [uM] |
|---|---|---|---|---|---|---|
| 2.44.222.I. | 2-(4,4-Difluoro-1-hydroxycyclohexyl)-N-(2-fluoro-2-methylpropyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide | 0.99 | 671.25 | | | 0.05 |
| 2.44.222R.I. | (R)-2-(4,4-Difluoro-1-hydroxycyclohexyl)-N-(2-fluoro-2-methylpropyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide | 1.00 | 671.15 | Chiralcel OZ-H B: 30% (1/1) MeCN/EtOH 5 min run | 1.6 | 7.9 |
| 2.44.222S.I. | (S)-2-(4,4-Difluoro-1-hydroxycyclohexyl)-N-(2-fluoro-2-methylpropyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide | 1.01 | 671.14 | Chiralcel OZ-H B: 30% (1/1) MeCN/EtOH 5 min run | 2.24 | 0.01 |
| 2.44.226R.I. | (R)-2-(4,4-difluoro-1-hydroxycyclohexyl)-1-(4,4-difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)ethan-1-one | 1.0 | 687.11 | Chiralpak IC B: 15% (1/1) MeCN/EtOH 5 min run | 2.2 | 0.89 |
| 2.44.226S.I. | (S)-2-(4,4-difluoro-1-hydroxycyclohexyl)-1-(4,4-difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)ethan-1-one | 1.0 | 687.1 | Chiralpak IC B: 15% (1/1) MeCN/EtOH 5 min run | 2.9 | 0.05 |
| 2.44.218.I. | N-(Cyclopropylmethyl)-2-(4,4-difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide | 0.97 | 651.27 | | | 0.03 |
| 2.44.201.I. | 2-(4,4-Difluoro-1-hydroxycyclohexyl)-2-(((2S,3R,4S,5R,6R)-5-hydroxy-6-(hydroxymethyl)-3-methoxy-4-(4- | 0.89 | 611.27 | | | 0.06 |

TABLE 12-continued

| Example | Name | $t_R$ | $[M + H]^+$ | HPLC conditions | $t_R$ chiral | $IC_{50}$ [uM] |
|---|---|---|---|---|---|---|
| | (3,4,5-trifluorophenyl)-1H-1,2,3-triazol-1-yl)tetrahydro-2H-pyran-2-yl)thio)-N,N-dimethylacetamide | | | | | |
| 2.44.203.I. | 2-(4,4-Difluoro-1-hydroxycyclohexyl)-N-ethyl-2-((((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide | 0.92 | 625.28 | | | 0.04 |
| 2.44.241.I. | 2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methyl-N-(2,2,2-trifluoroethyl)acetamide | 0.99 | 679.15 | | | 0.18 |
| 2.44.242.I. | 2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-isopropyl-N-methylacetamide | 0.96 | 639.22 | | | 0.08 |
| 2.44.225.I. | 2-(4,4-Difluoro-1-hydroxycyclohexyl)-N-(3,3-dimethylbutyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide | 1.06 | 681.26 | | | 0.10 |
| 2.44.217.I. | N-(2-Cyclopropylethyl)-2-(4,4-difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide | 1.01 | 665.22 | | | 0.05 |
| 2.44.237.I. | 2-(4,4-Difluoro-1-hydroxycyclohexyl)-N-(3,3-difluorocyclobutyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide | 0.99 | 687.22 | | | 0.09 |
| 2.44.243.I. | 2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methyl-N-(oxetan-3-yl)acetamide | 0.88 | 653.21 | | | 0.11 |
| 2.44.213.I. | 2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methyl-N-(tetrahydro-2H-pyran-4-yl)acetamide | 0.92 | 681.24 | | | 0.07 |
| 2.44.244.I. | 2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-1-morpholinoethan-1-one | 0.89 | 653.22 | | | 0.07 |
| 2.44.245.I. | 2-(4,4-Difluoro-1-hydroxycyclohexyl)-1-(4,4-dimethylpiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)ethan-1-one | 1.03 | 679.31 | | | 0.09 |
| 2.44.246.I. | 2-(4,4-Difluoro-1-hydroxycyclohexyl)-N-(4,4-dimethylcyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide | 1.09 | 707.03 | | | 0.32 |

TABLE 12-continued

| Example | Name | $t_R$ | $[M + H]^+$ | HPLC conditions | $t_R$ chiral | $IC_{50}$ [uM] |
|---|---|---|---|---|---|---|
| 2.44.247.I. | N-(Bicyclo[1.1.1]pentan-1-yl)-2-(4,4-difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide | 1.02 | 663.19 | | | 0.05 |
| 2.44.248.I. | 2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide | 0.91 | 597.98 | | | 0.49 |
| 2.44.249.I. | 2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-(tetrahydro-2H-pyran-4-yl)acetamide | 0.89 | 667.14 | | | 0.08 |
| 2.44.250.I. | 2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-(pentan-3-yl)acetamide | 1.0 | 653.16 | | | 0.05 |
| 2.44.251.I. | 2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-isopropylacetamide | 0.94 | 625.14 | | | 0.09 |
| 2.44.252.I. | 2-(4,4-Difluoro-1-hydroxycyclohexyl)-N-(3,3-dimethylbuty1)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide | 1.04 | 667.16 | | | 0.32 |
| 2.44.253.I. | 2-(4,4-Difluoro-1-hydroxycyclohexyl)-N-(3,3-difluorocyclobutyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide | 0.96 | 673.12 | | | 0.16 |
| 2.44.254.I. | 2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-(2,2,2-trifluoroethyl)acetamide | 0.96 | 665.09 | | | 0.13 |
| 2.44.255.I | 2-(4,4-Difluoro-1-hydroxycyclohexyl)-N-(4,4-dimethylcyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide | 1.07 | 693.95 | | | 0.39 |

Example 2.67.226.1

1-(4,4-Difluoropiperidin-1-yl)-2-(((2S,3R,4S,5R, 6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-(6-hydroxyspiro[2.5] octan-6-yl)ethan-1-one 1. 1-(4,4-Difluoropiperidin-1-yl)-2-(6-hydroxyspiro [2.5]octan-6-yl)-2-mercaptoethan-1-one 1-(4,4-Difluoropiperidin-1-yl)-2-(6-hydroxyspiro[2.5]octan-6-yl)-2-mercaptoethan-1-one is synthesized from 3,4-dihydro-2H-pyran, ethyl 2-mercaptoacetate, 4,4-difluoropiperidine and spiro[2.5]octan-6-one as a beige solid according to the procedure described for the synthesis of Intermediate 12. LC-MS(A) $t_R$=0.95 min, $[M+H]^+$: 320.15

2. ((2R,3R,4S,5R,6S)-3-Acetoxy-6-((2-(4,4-difluoropiperidin-1-yl)-1-(6-hydroxyspiro[2.5]octan-6-yl)-2-oxoethyl)thio)-5-methoxy-4-(4-(3,4,5-trifluorophenyl)-1H-1,2,3-triazol-1-yl)tetrahydro-2H-pyran-2-yl) methyl acetate ((2R,3R,4S,5R,6S)-3-Acetoxy-6-((2-(4,4-difluoropiperidin-1-yl)-1-(6-hydroxyspiro[2.5]octan-6-yl)-2-oxoethypthio)-5-methoxy-4-(4-(3,4,5-trifluorophenyl)-1H-1,2,3-triazol-1-yl)tetrahydro-2H-pyran-2-yl)methyl acetate is prepared from Step 1. of this experiment, 1-(4,4-difluoropiperidin-1-yl)-2-(6-hydroxyspiro[2.5]octan-6-yl)-2-mercaptoethan-1-one, and Intermediate 14 as a beige solid according to the procedure described for the synthesis of Intermediate 13. LC-MS(A) $t_R$=1.13 min, [M+H]$^+$: 761.26

3. 1-(4,4-Difluoropiperidin-1-yl)-2O2S,3R,4S,5R, 6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-(6-hydroxyspiro[2.5]octan-6-yl)ethan-1-one (2.67.226.1.)

To a solution of ((2R,3R,4S,5R,6S)-3-acetoxy-6-(((2-(4, 4-difluoropiperidin-1-yl)-1-(6-hydroxyspiro[2.5]octan-6-yl)-2-oxoethypthio)- 5-methoxy-4-(4-(3,4,5-trifluorophenyl)-1H-1,2,3-triazol-1-yl)tetrahydro-2H-pyran-2-yl)methyl acetate (0.05 g, 0.07 mmol, 1.0 eq) in MeOH (3.0 mL) is added $K_2CO_3$ (0.002 g, 0.01 mmol, 0.2 eq) at rt. The reaction mixture is stirred at rt for 90 min, then diluted with MeCN, followed by water. The mixture is directly purified by preparative HPLC/MS(I) to yield the title compound as a beige solid (0.04 g, 79%). LC-MS(A) $t_R$=1.02 min, [M+H]$^+$: 677.19.

Following examples have been prepared starting from 1-(4,4-difluoropiperidin-1-yl)-2-((tetrahydro-2H-pyran-2-yl)thio)ethan-1-one (synthesized in analogy to Intermediate 12, Step 1.-3.), the corresponding ketones and Intermediate 14 in analogy to Example 2.67.226.1. LC-MS and Gal-3 inhibition data are listed in Table 13 below. The LC-MS conditions used are LC-MS (A). Chiral HPLC (conditions and retention time) and inhibition data of the epimers R and S of selected Examples are also listed.

TABLE 13

| Example | Name | $t_R$ | [M + H]$^+$ | HPLC conditions | $t_R$ chiral | IC$_{50}$ [uM] |
|---|---|---|---|---|---|---|
| 2.67.226.I. | 1-(4,4-Difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-(6-hydroxyspiro[2.5]octan-6-yl)ethan-1-one | 1.02 | 677.19 | | | 0.12 |
| 2.68.226.I. | 1-(4,4-Difluoropiperidin-1-yl)-2-(1-hydroxy-4,4-dimethylcyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)ethan-1-one | 1.04 | 679.23 | | | 0.10 |
| 2.69.226R.I.* | (R)-1-(4,4-Difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-(7-hydroxyspiro[3.5]nonan-7-yl)ethan-1-one | 1.05 | 691.25 | Chiralpak ID B: 25% (1/1) MeCN/MeOH 5 min run | 1.94 | 0.57 |
| 2.69.226S.I.* | (S)-1-(4,4-Difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-(7-hydroxyspiro[3.5]nonan-7-yl)ethan-1-one | 1.06 | 691.26 | Chiralpak ID B: 25% (1/1) MeCN/MeOH 5 min run | 2.2 | 0.12 |
| 2.70.226.I. | 1-(4,4-Difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-(7-hydroxy-2-oxaspiro[3.5]nonan-7-yl)ethan-1-one | 0.91 | 694.06 | | | 0.11 |
| 2.71.226R.I.* | (R)-1-(4,4-Difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-(8-hydroxyspiro[4.5]decan-8-yl)ethan-1-one | 1.07 | 705.27 | Chiralpak IA B: 30% (1/1) MeCN/EtOH 5 min run | 2.02 | 0.67 |
| 2.71.226S.I.* | (S)-1-(4,4-Difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-(8-hydroxyspiro[4.5]decan-8-yl)ethan-1-one | 1.08 | 705.28 | Chiralpak IA B: 30% (1/1) MeCN/EtOH 5 min run | 2.27 | 0.1 |
| 2.72.226.I. | 1-(4,4-Difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-(9-hydroxy-3-oxaspiro[5.5]undecan-9-yl)ethan-1-one | 0.96 | 721.51 | | | 0.06 |

TABLE 13-continued

| Example | Name | $t_R$ | $[M + H]^+$ | HPLC conditions | $t_R$ chiral | $IC_{50}$ [uM] |
|---|---|---|---|---|---|---|
| 2.72.226R.I.* | (R)-1-(4,4-Difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-(9-hydroxy-3-oxaspiro[5.5]undecan-9-yl)ethan-1-one | 0.96 | 721.17 | Chiralcel OZH B: 45% (1/1) MeCN/MeOH 5 min run | 1.48 | 14.9 |
| 2.72.226S.I.* | (S)-1-(4,4-Difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-(9-hydroxy-3-oxaspiro[5.5]undecan-9-yl)ethan-1-one | 0.97 | 721.15 | Chiralcel OZH B: 45% (1/1) MeCN/MeOH 5 min run | 2.23 | 0.04 |
| 2.43.226.I. | 1-(4,4-Difluoropiperidin-1-yl)-2-(4-hydroxy-2,2-dimethyltetrahydro-2H-pyran-4-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)ethan-1-one | 1.0 | 713.43 | | | 0.25 |
| 2.73.226.I. | 2-(1,1-Difluoro-6-hydroxyspiro[2.5]octan-6-yl)-1-(4,4-difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)ethan-1-one | 0.92-0.94 | 681.18 | | | 0.10 |

*Epimers are separated during the purification on preparative HPLC/MS(I) or HPLC/MS(II).

Example 2.44.226.II 2-(4,4-Difluoro-1-hydroxycyclohexyl)-1-(4,4-difluoropiperidin-1-yl)-2-(((2S,3R,4S,5R,6R)-3-ethoxy-5-hydroxy-6-(hydroxymethyl)-4-(4-(3,4,5-trifluorophenyl)-1H-1,2,3-triazol-1-yl)tetrahydro-2H-pyran-2ll)thio)ethan-1-one Example 2.44.226.II. is prepared from 2-(4,4-difluoro-1-hydroxycyclohexyl)-1-(4,4-difluoropiperidin-1-yl)-2-mercaptoethan-1-one (prepared in analogy to Intermediate 11) and Intermediate 15 in analogy to Example 2.67.226.1. as a beige solid. LC-MS (A): $t_R$=1.0 min; $[M+H]^+$: 701.21. LC-MS and Gal-3 inhibition data of Example 2.44.226.II. are listed in Table 14 below. The LC-MS conditions used are LC-MS (A).

TABLE 14

| Example | Name | $t_R$ | $[M + H]^+$ | $IC_{50}$ [uM] |
|---|---|---|---|---|
| 2.44.226.II. | 2-(4,4-Difluoro-1-hydroxycyclohexyl)-1-(4,4-difluoropiperidin-1-yl)-2-(((2S,3R,4S,5R,6R)-3-ethoxy-5-hydroxy-6-(hydroxymethyl)-4-(4-(3,4,5-trifluorophenyl)-1H-1,2,3-triazol-1-yl)tetrahydro-2H-pyran-2-yl)thio)ethan-1-one | 1.00 | 701.21 | 0.1 |

Galectin-1 enzyme inhibition data are listed in Table 15 below. Inhibition data of the epimers R and S of selected Examples are also listed.

TABLE 15

| Example | $IC_{50}$ [uM] | Example | $IC_{50}$ [uM] | Example | $IC_{50}$ [uM] | Example | $IC_{50}$ [uM] |
|---|---|---|---|---|---|---|---|
| 2.53.203. | 35.9 | 2.31.204. | 2.8 | 2.41.201. | 1.8 | 2.41.207R. | 51.5 |
| 2.56.203S. | 36 | 2.31.205R. | 20.0 | 2.41.201R. | >100 | 2.41.207S. | 0.9 |
| 2.41.200. | 0.26 | 2.31.205S. | 0.82 | 2.41.201S. | 0.21 | 2.41.208. | 0.22 |
| 2.41.200R. | 10.9 | 2.31.206. | 1.4 | 2.41.202. | 0.11 | 2.41.208R. | 32.3 |
| 2.41.200S. | 0.11 | 2.40.200. | 0.19 | 2.41.204. | 0.95 | 2.41.208S. | 0.8 |
| 2.31.201. | 1.92 | 2.40.203. | 0.16 | 2.41.205R. | 4.9 | 2.41.209. | 0.31 |
| 2.31.203. | 0.88 | 2.40.207. | 0.59 | 2.41.205S. | 0.55 | 2.41.209S. | 0.17 |
| 2.31.203S. | 0.24 | 2.40.208. | 0.05 | 2.41.206. | 1.5 | 2.41.210. | 1.12 |
| 2.31.202. | 2.77 | 2.40.209. | 0.23 | 2.41.207. | 0.072 | 2.41.211. | 0.33 |
| 2.41.212. | 0.2 | 2.39.220. | 8.79 | 2.44.227R. | 5.13 | 2.34.222S. | 0.11 |
| 2.41.212R. | 79.2 | 2.39.222. | 0.12 | 2.44.227S. | 0.23 | 2.34.228. | 0.16 |
| 2.41.212S. | 0.08 | 2.39.222R. | 38.1 | 2.38.203. | 1.13 | 2.34.228R. | 22.6 |
| 2.41.213. | 0.2 | 2.39.222S. | 0.09 | 2.38.206. | 0.77 | 2.34.228S. | 0.09 |
| 2.41.214. | 0.12 | 2.39.224R. | 2.82 | 2.38.219. | 0.11 | 2.33.203R. | 4.2 |
| 2.41.215. | 0.37 | 2.39.224S. | 0.07 | 2.38.220. | 0.02 | 2.33.203S. | 0.11 |
| 2.41.216. | 0.38 | 2.44.201. | 0.23 | 2.38.228. | 0.17 | 2.33.206. | 1.71 |

TABLE 15-continued

| Example | IC$_{50}$ [uM] | Example | IC$_{50}$ [uM] | Example | IC$_{50}$ [uM] | Example | IC$_{50}$ [uM] |
|---|---|---|---|---|---|---|---|
| 2.41.216S. | 0.11 | 2.44.201R. | 1.71 | 2.34.203. | 0.64 | 2.33.218R. | 0.58 |
| 2.41.217. | 0.22 | 2.44.201S. | 0.18 | 2.34.203R. | 28.3 | 2.33.218S. | 0.06 |
| 2.41.218. | 0.19 | 2.44.203. | 0.14 | 2.34.203S. | 0.17 | 2.32.203. | 1.89 |
| 2.41.218R. | 19.03 | 2.44.206R. | 1.48 | 2.34.206. | 2.71 | 2.32.203R. | 30.8 |
| 2.41.218S. | 0.05 | 2.44.206S. | 0.19 | 2.34.206R. | 6.91 | 2.32.203S. | 0.73 |
| 2.41.203. | 0.42 | 2.44.208. | 0.21 | 2.34.206S. | 0.62 | 2.32.218. | 1.13 |
| 2.41.203R. | >39.8 | 2.44.208S. | 0.03 | 2.34.208. | 0.52 | 2.32.222. | 2.06 |
| 2.41.203S. | 0.067 | 2.44.218. | 0.03 | 2.34.208R. | 11.5 | 2.31.207. | 0.57 |
| 2.41.219. | 0.21 | 2.44.218R. | 1.9 | 2.34.208S. | 0.14 | 2.31.208. | 0.03 |
| 2.41.236. | 9.9 | 2.44.218S. | 0.04 | 2.34.218. | 0.22 | 2.31.211R | 2.15 |
| 2.41.235. | 0.09 | 2.44.221. | 0.06 | 2.34.218R. | 20.9 | 2.31.211S. | 0.53 |
| 2.41.235R. | 6.54 | 2.44.222. | 0.35 | 2.34.218S. | 0.07 | 2.31.215. | 1.68 |
| 2.41.235S. | 0.09 | 2.44.223. | 0.12 | 2.34.219. | 0.64 | 2.31.218. | 0.22 |
| 2.39.203. | 0.17 | 2.44.223R. | 13.44 | 2.34.219R. | 33.6 | 2.31.228. | 1.65 |
| 2.39.208. | 0.07 | 2.44.223S. | 0.08 | 2.34.219S. | 0.12 | 2.31.229. | 0.8 |
| 2.39.219R. | 0.55 | 2.44.225. | 0.15 | 2.34.222. | 0.22 | 2.31.230. | 1.25 |
| 2.39.219S. | 0.1 | 2.44.226. | 0.11 | 2.34.222R. | 46 | 2.60.203. | 1.02 |
| 2.60.206. | 3.4 | 2.49.226S.I. | 1.7 | 11.41.203. | 0.32 | 2.44.238.I. | 0.06 |
| 2.60.218 | 0.2 | 2.41.232. | 0.06 | 14.41.203. | 0.03 | 2.44.243.I. | 0.17 |
| 2.64.203 | 1.46 | 2.41.231. | 0.08 | 12.41.203. | 0.36 | 2.44.213.I. | 0.15 |
| 2.64.206. | 5.94 | 2.41.231R. | 8.26 | 13.41.203. | 0.13 | 2.44.244.I. | 0.1 |
| 2.64.218. | 0.34 | 2.41.231S. | 0.05 | 15.41.203. | 0.08 | 2.44.245.I. | 0.21 |
| 2.65.203. | 3.05 | 2.41.233R. | 9.8 | 16.41.203. | 0.13 | 2.44.246.I. | 1.2 |
| 2.65.206. | 7.29 | 2.41.233S. | 0.03 | 17.41.203. | 0.14 | 2.44.247.I. | 0.03 |
| 2.65.218. | 3.07 | 2.41.234R | 10.9 | 18.41.203. | 0.35 | 2.44.248.I. | 0.73 |
| 2.47.203. | 0.11 | 2.41.234S. | 0.1 | 19.41.203. | 0.15 | 2.44.249.I. | 0.36 |
| 2.47.203R. | 33.9 | 2.41.233R.I. | 7.1 | 20.41.203. | 0.18 | 2.44.250.I. | 0.27 |
| 2.47.203S. | 0.03 | 2.41.233S.I. | 0.03 | 21.44.221R. | 0.22 | 2.44.251.I. | 0.19 |
| 2.51.203. | 0.07 | 2.41.237. | 0.02 | 21.44.221S. | 0.07 | 2.44.252.I. | 0.83 |
| 2.51.203R. | 7.5 | 2.41.220. | 0.03 | 2.44.222.I. | 0.22 | 2.44.253.I. | 0.67 |
| 2.51.203S. | 0.03 | 2.44.238.I. | 011 | 2.44.222R.I. | 8.78 | 2.44.254.I. | 0.3 |
| 2.49.203. | 0.07 | 2.44.238R.I. | >100 | 2.44.222S.I. | 0.07 | 2.44.255.I. | 0.83 |
| 2.49.203R. | 4.43 | 2.44.238S.I. | 0.03 | 2.44.226R.I. | 5.73 | 2.67.226.I. | 0.17 |
| 2.49.203S. | 0.06 | 2.44.239.I. | 0.02 | 2.44.226S.I. | 0.07 | 2.68.226.I. | 0.19 |
| 2.50.203. | 0.1 | 2.44.214.I. | 0.02 | 2.44.218.I. | 0.08 | 2.69.226R.I. | 1.64 |
| 2.50.203R. | 10.5 | 2.44.240.I. | 0.28 | 2.44.201.I. | 0.25 | 2.69.226S.I. | 0.27 |
| 2.50.203S. | 0.06 | 2.44.256.I. | 0.13 | 2.44.203.I. | 0.12 | 2.70.226.I. | 0.2 |
| 2.58.203R. | 1.18 | 2.44.257.I. | 0.18 | 2.44.241.I. | 0.65 | 2.71.226R.I. | 1.1 |
| 2.58.203S. | 0.1 | 10.41.203. | 0.27 | 2.44.242.I. | 0.11 | 2.71.226S.I. | 0.27 |
| 2.49.226.I. | 0.18 | 1.41.203. | 0.16 | 2.44.225.I. | 0.12 | 2.72.226.I. | 0.12 |
| 2.49.226R.I. | 0.08 | 3.41.203. | 0.68 | 2.44.217.I. | 0.11 | 2.72.226R.I. | 39.6 |
| 2.72.226S.I. | 0.1 | 2.43.226.I. | 0.46 | 2.73.226.I. | 0.15 | 2.44.226.II. | 0.1 |

Biological Assay

Evaluation of Compound Inhibitory Activity (IC$_{50}$)

The inhibitory activity of compounds is determined in competitive binding assays. This spectrophotometric assay measures the binding of biotinylated human Gal-3 (hGal-3) or human Gal-1 (hGal-1), respectively, to a microplate-adsorbed glycoprotein, asialofetuin (ASF) (Proc Natl Acad Sci USA. 2013 Mar. 26; 110(13):5052-7.).

Briefly, compounds are serially diluted in DMSO (working dilutions). ASF-coated 384well plates are supplemented with 22.8 µL/well of biotinylated hGal-3 or hGal-1 in assay buffer (i.e. 300-1000 ng/mL biotinylated hGal-3 or hGal-1) to which 1.2 µL of compound working dilutions are added and mixed.

Plates are incubated for 3 hours at 4° C., then washed with cold assay buffer (3×50 uL), incubated for 1 hour with 25 µL/well of a streptavidin-peroxidase solution (diluted in assay buffer to 80 ng/mL) at 4° C., followed by further washing steps with assay buffer (3×50 uL). Finally, 25 µL/well of ABTS substrate is added. OD (410 nm) is recorded after 30 to 45 min and IC$_{50}$ values are calculated.

The calculated IC$_{50}$ values may fluctuate depending on the daily assay performance. Fluctuations of this kind are known to those skilled in the art. IC$_{50}$ values from several measurements are given as mean values.

The invention claimed is:

1. A compound of Formula (I)

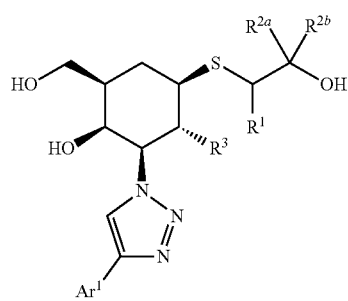

Formula (I)

wherein

R$^1$ represents an amide group of the structure:

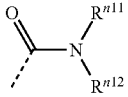

wherein
R$^{N11}$ represents
—C$_{1-6}$-alkyl;
—CH$_2$—CH$_2$—O—C$_{1-3}$-alkyl;
—CH$_2$—C$_{1-3}$-fluoroalkyl;
—C$_{0-2}$-alkylene-C$_{3-6}$-cycloalkyl, wherein said C$_{3-6}$-cycloalkyl is unsubstituted or mono- or di-substituted with fluoro or methyl;
—C$_{0-2}$-alkylene-C$_{4-6}$-cycloalkyl wherein said C$_{4-6}$-cycloalkyl contains one oxygen ring atom;
—CH$_2$—CH$_2$—NR$^{N21}$R$^{N22}$, wherein R$^{N21}$ and R$^{N22}$ together with the nitrogen atom to which they are attached form a 4- to 6-membered heterocyclyl selected from azetidine-1-yl, pyrrolidine-1-yl, piperidine-1-yl, and morpholin-4-yl; or
—C$_{1-2}$-alkylene-R$^{11}$, wherein R$^{11}$ represents phenyl or 5- or 6-membered heteroaryl wherein said phenyl or 5- or 6-membered heteroaryl independently is unsubstituted or mono-substituted with methyl;
phenyl or 5- or 6-membered heteroaryl wherein said phenyl or 5- or 6-membered heteroaryl independently is unsubstituted or mono-substituted with methyl; or

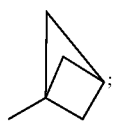

and R$^{N12}$ represents hydrogen or C$_{1-2}$-alkyl;
or R$^{N11}$ and R$^{N12}$ together with the nitrogen atom to which they are attached form a 4- to 6-membered heterocyclyl selected from azetidine-1-yl, pyrrolidine-1-yl, and piperidine-1-yl, wherein said 4- to 6-membered heterocyclyl independently is unsubstituted, mono-, or di-substituted, wherein the substituents independently are methyl or fluoro;
or R$^{N11}$ and R$^{N12}$ together with the nitrogen atom to which they are attached form morpholin-4-yl;
or R$^{N11}$ and R$^{N12}$ together with the nitrogen atom to which they are attached to form a partially aromatic bicyclic ring consisting of a pyrrolidine-1-yl or a piperidine-1-yl, wherein said pyrrolidine or piperidine is fused to a phenyl ring;
Ar$^1$ represents
aryl which is mono-, di-, tri-, tetra-, or penta-substituted, wherein the substituents are independently selected from halogen, methyl, cyano, and methoxy; or
5- or 6-membered heteroaryl, wherein said 5- or 6-membered heteroaryl independently is unsubstituted, mono- or di-substituted, wherein the substituents are independently selected from halogen, methyl, cyano, and methoxy;
R$^{2a}$ represents hydrogen; and R$^{2b}$ represents
—C$_{2-4}$-alkyl,
—C$_{0-1}$-alkylene-Ar$^{2b}$, wherein Ar$^{2b}$ represents phenyl or 5- or 6-membered heteroaryl, wherein said phenyl or 5- or 6-membered heteroaryl independently is unsubstituted, mono- or di-substituted with methyl;
or R$^{2a}$ and R$^{2b}$ both represent hydrogen, methyl, ethyl, or n-propyl;

or R$^{2a}$ and R$^{2b}$ together with the carbon atom to which they are attached form a 3- to 6-membered ring selected from
C$_{3-6}$-cycloalkylene, wherein said C$_{3-6}$-cycloalkylene independently is unsubstituted, mono-, or di-substituted, wherein the substituents independently are methyl or fluoro;
tetrahydro-2H-pyran-4,4-diyl, which is unsubstituted, di-, or tetra-substituted with methyl; or
piperidine-4,4-diyl, pyrrolidine-3,3-diyl, or azetidine-3,3-diyl wherein the nitrogen of said piperidine, pyrrolidine or azetidine independently is unsubstituted, or substituted with —C$_{1-3}$-alkyl, —C$_{0-2}$-alkylene-C$_{3-6}$-cycloalkyl, or -L-R$^{N2}$ wherein
-L- represents —CO—, —SO$_2$—, *—CO—NH—, *—CO—O—, or *—SO$_2$—NH—, and
R$^{N2}$ represents —C$_{1-3}$-alkyl or —C$_{0-2}$-alkylene-C$_{3-6}$-cycloalkyl;
wherein in the above groups the asterisks indicate the bond which is connected to the rest of the molecule; or
R$^{2a}$ and R$^{2b}$ together with the carbon atom to which they are attached form a spiro-bicyclic ring system of the structure (S$^{2AB}$)

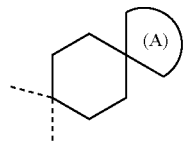

wherein ring (A) represents a 3- to 6-membered non-aromatic carbocyclic ring, wherein said 3- to 6-membered non-aromatic carbocyclic ring optionally contains one ring oxygen atom and wherein said 3- to 6-membered non-aromatic carbocyclic ring is unsubstituted or di-substituted with fluoro; and
R$^3$ represents hydroxy or C$_{1-3}$-alkoxy;
or a pharmaceutically acceptable salt thereof.

2. A compound according to claim 1 wherein said compound is a compound of Formula (I$_S$),

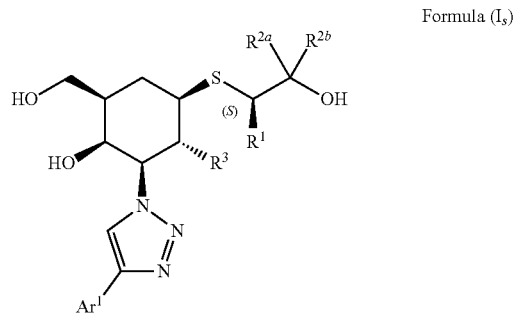

Formula (I$_S$)

wherein the carbon atom to which the group R$^1$ is attached is in the absolute configuration as drawn in Formula (I$_S$);
or a pharmaceutically acceptable salt thereof.

3. A compound according to claim 1; wherein Ar$^1$ represents phenyl which is mono-, di- or tri-substituted, wherein the substituents are independently selected from halogen, methyl, cyano, and methoxy;

wherein at least one of said substituents is attached in a meta- or in para-position of said phenyl;
or a pharmaceutically acceptable salt thereof.

4. A compound according to claim 3; wherein at least one of said substituents is attached in a meta-position of said phenyl and the substituent is halogen;
or a pharmaceutically acceptable salt thereof.

5. A compound according to claim 3; wherein at least one of said substituents is attached in para-position of said phenyl and the substituent is selected from halogen, methyl, cyano, and methoxy;
or a pharmaceutically acceptable salt thereof.

6. A compound according to claim 1; wherein $Ar^1$ represents a phenyl group of the structure

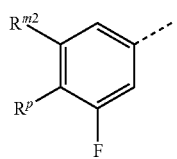

(Ar-I)

wherein
$R^{m2}$ represents halogen; and
$R^p$ represents hydrogen, halogen, methyl, cyano, or methoxy;
or a pharmaceutically acceptable salt thereof.

7. A compound according to claim 1; wherein $R^1$ represents an amide group of the structure

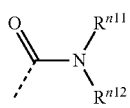

wherein
$R^{N11}$ represents
—$C_{1-6}$-alkyl;
—$CH_2$—$C_{1-3}$-fluoroalkyl;
cyclopropyl, cyclobutyl, —$CH_2$-cyclopropyl, —$CH_2$-cyclopentyl, —$CH_2$-1-fluorocyclopentyl, or —$CH_2$—$CH_2$-cyclopropyl;
—$CH_2$-tetrahydro-2H-pyran-4-yl, or —$CH_2$—$CH_2$-tetrahydro-2H-pyran-4-yl;
tetrahydro-2H-pyran-4-yl, or oxetane-3-yl;
benzyl;
phenyl, or pyridinyl; or

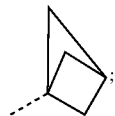

and $R^{N12}$ represents hydrogen or $C_{1-2}$-alkyl;
or $R^{N11}$ and $R^{N12}$ together with the nitrogen atom to which they are attached form a 4- to 6-membered heterocyclyl selected from azetidin-1-yl which is unsubstituted, or di-substituted in position 3 with fluoro; pyrrolidin-1-yl which is unsubstituted, or di-substituted in position 3 with fluoro; and piperidin-1-yl which is unsubstituted, or di-substituted in position 3 or 4 with fluoro;

or $R^{N11}$ and $R^{N12}$ together with the nitrogen atom to which they are attached form morpholin-4-yl;
or $R^{N11}$ and $R^{N12}$ together with the nitrogen atom to which they are attached form an indolin-1-yl ring;
or a pharmaceutically acceptable salt thereof.

8. A compound according to claim 1; wherein $R^1$ represents an amide group of the structure

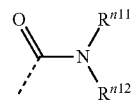

wherein
$R^{N11}$ represents
—$C_{1-6}$-alkyl;
—$CH_2$—$CH_2$—O—$C_{1-3}$-alkyl;
—$CH_2$—$C_{1-3}$-fluoroalkyl; or
cyclopropyl, cyclobutyl, —$CH_2$-cyclopropyl, —$CH_2$-cyclopentyl, —$CH_2$-1-fluorocyclopentyl, or —$CH_2$—$CH_2$-cyclopropyl;
and $R^{N12}$ represents $C_{1-2}$-alkyl;
or a pharmaceutically acceptable salt thereof.

9. A compound according to claim 1; wherein
$R^{2a}$ represents hydrogen; and $R^{2b}$ represents
—$C_{2-4}$-alkyl;
benzyl;
phenyl which is unsubstituted, mono- or di-substituted with methyl; or
5-membered heteroaryl which is unsubstituted or mono-substituted with methyl;
or $R^{2a}$ and $R^{2b}$ both represent methyl, ethyl, or n-propyl;
or $R^{2a}$ and $R^{2b}$ together with the carbon atom to which they are attached form a 3- to 6-membered ring selected from
$C_{4-6}$-cycloalkylene, wherein said $C_{4-6}$-cycloalkylene independently is unsubstituted, mono-, or di-substituted, wherein the substituents independently are methyl or fluoro;
tetrahydro-2H-pyran-4,4-diyl; or
piperidine-4,4-diyl, wherein the nitrogen of said piperidine is unsubstituted, or substituted with —$C_{1-3}$-alkyl, —CO—$C_{1-3}$-alkyl, —CO—O—$C_{1-3}$-alkyl, —CO—NH-cyclopropyl, —$SO_2$—$C_{1-3}$-alkyl, —$SO_2$-cyclopropyl, or —$SO_2$—NH—$C_{1-3}$-alkyl;
azetidine-3,3-diyl, wherein the nitrogen of said azetidine is substituted with —CO—O—$C_{1-3}$-alkyl; or
$R^{2a}$ and $R^{2b}$ together with the carbon atom to which they are attached form a spiro-bicyclic ring system of the structure:

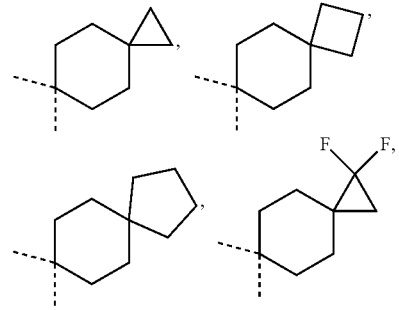

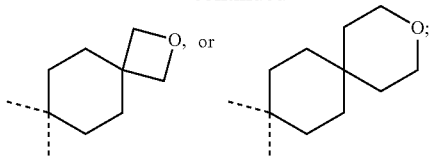

or a pharmaceutically acceptable salt thereof.

10. A compound according to claim 1; wherein R³ represents methoxy;
or a pharmaceutically acceptable salt thereof.

11. A pharmaceutical composition comprising a compound according to claim 1, or a pharmaceutically acceptable salt thereof, and a pharmaceutically acceptable carrier.

12. A method for the treatment of an indication mediated by galectin-3 selected from fibrosis of organs; neuropathic pain; insulin resistance disorders, and cancer wherein the cancer is treated in combination with immunotherapy, comprising administering to a subject in a need thereof an effective amount of a compound according to claim 1, or of a pharmaceutically acceptable salt thereof.

13. A compound, wherein said compound is:
- (S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-isobutyl-N-methylacetamide;
- (S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N,N,3-trimethylbutanamide;
- (S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-3-hydroxy-N,3-dimethylbutanamide;
- (S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N,N-diethyl-3-hydroxy-3-methylbutanamide;
- (S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-methyl-1-((R)-2-methylazetidin-1-yl) butan-1-one;
- (S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-methyl-1-((S)-2-methylazetidin-1-yl) butan-1-one;
- (S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-methyl-1-(3-methylazetidin-1-yl) butan-1-one;
- (S)-1-(azetidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-methylbutan-1-one;
- (S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxy-1-methylpiperidin-4-yl)-N-isobutyl-N-methylacetamide;
- (S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxy-1-methylpiperidin-4-yl)-N-methylacetamide;
- (S)—N-benzyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxy-1-methylpiperidin-4-yl)-N-methylacetamide;
- (S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxy-1-methylpiperidin-4-yl)-1-(piperidin-1-yl)ethan-1-one;
- (S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxy-1-methylpiperidin-4-yl)-1-(indolin-1-yl)ethan-1-one;
- (S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N,N-dimethylacetamide;
- (S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N,N-diethyl-2-(4-hydroxytetrahydro-2H-pyran-4-yl)acetamide;
- (S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-1-((R)-2-methylazetidin-1-yl) ethan-1-one;
- (S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-1-((S)-2-methylazetidin-1-yl) ethan-1-one;
- (S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-1-(3-methylazetidin-1-yl)ethan-1-one;
- (S)-1-(azetidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)ethan-1-one;
- (S)—N-benzyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methylacetamide;
- (S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-1-(piperidin-1-yl)ethan-1-one;
- (S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-1-(indolin-1-yl)ethan-1-one;
- (S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(thiophen-2-ylmethyl)acetamide;
- (S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-1-(pyrrolidin-1-yl)ethan-1-one;
- (S)—N-(cyclopentylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methylacetamide;
- (S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-((tetrahydro-2H-pyran-4-yl)methyl)acetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxytetrahydro-2H-pyran-4-yl)-N-(tetrahydro-2H-pyran-4-yl)methyl)acetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-((1-methyl-1H-imidazol-4-yl)methyl)acetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(2-(tetrahydro-2H-pyran-4-yl)ethyl)acetamide;

(S)—N-(2-cyclopropylethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methylacetamide;

(S)—N-cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxytetrahydro-2H-pyran-4-yl)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(2,2,2-trifluoroethyl)acetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(1-hydroxycyclohexyl)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclohexyl)-1-(piperidin-1-yl)ethan-1-one;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclohexyl)-N-methyl-N-(2,2,2-trifluoroethyl)acetamide;

(S)—N-cyclobutyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclohexyl)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-(2-fluoro-2-methylpropyl)-2-(1-hydroxycyclohexyl)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclohexyl)-N-methyl-N-(pyridin-2-ylmethyl)acetamide;

(S)-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N,N-dimethylacetamide;

(S)-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-N-methylacetamide;

(S)—N-cyclobutyl-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-methylacetamide;

(S)-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-1-(piperidin-1-yl)ethan-1-one;

(S)—N-(cyclopropylmethyl)-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-methylacetamide;

(S)—N-cyclopropyl-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-methylacetamide;

(S)-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-(2-fluoro-2-methylpropyl)-N-methylacetamide;

(S)-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-((1-fluorocyclopentyl)methyl)-N-methylacetamide;

(S)-2-(4,4-difluoro-1-hydroxycyclohexyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-(3,3-dimethylbutyl)-N-methylacetamide;

(S)-2-(4,4-difluoro-1-hydroxycyclohexyl)-1-(4,4-difluoropiperidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)ethan-1-one;

(S)-2-(4,4-difluoro-1-hydroxycyclohexyl)-1-(3,3-difluoroazetidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio) ethan-1-one;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(1-hydroxycyclopentyl)-N-methylacetamide;

(S)-1-(azetidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclopentyl)ethan-1-one;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclopentyl)-N-methyl-N-(2,2,2-trifluoroethyl)acetamide;

(S)—N-cyclobutyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclopentyl)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclopentyl)-N-methyl-N-neopentylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(1-hydroxycyclobutyl)-N-methylacetamide;

(S)-1-(azetidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)ethan-1-one;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)-1-(piperidin-1-yl)ethan-1-one;

(S)—N-(cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)-N-methyl-N-(2,2,2-trifluoroethyl)acetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-(2-fluoro-2-methylpropyl)-2-(1-hydroxycyclobutyl)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(1-hydroxycyclobutyl)-N-methyl-N-neopentylacetamide;

(S)-2-(3,3-difluoro-1-hydroxycyclobutyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-N-methylacetamide;

(S)-1-(azetidin-1-yl)-2-(3,3-difluoro-1-hydroxycyclobutyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio) ethan-1-one;

(S)—N-(cyclopropylmethyl)-2-(3,3-difluoro-1-hydroxycyclobutyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-methylacetamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N,3-diethyl-3-hydroxy-N-methylpentanamide;

(S)—N-(cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-ethyl-3-hydroxy-N-methylpentanamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-ethyl-N-(2-fluoro-2-methylpropyl)-3-hydroxy-N-methylpentanamide;

(S)—N-benzyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N,3-dimethylbutanamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-methyl-1-(piperidin-1-yl) butan-1-one;

(S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-methyl-1-(pyrrolidin-1-yl) butan-1-one;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N-((1-methyl-1H-imidazol-4-yl)methyl) butanamide;

(S)—N-(cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N,3-dimethylbutanamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N,3-dimethyl-N-neopentylbutanamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N-(2-methoxyethyl)-N,3-dimethylbutanamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N,3-dimethyl-N-(2-morpholinoethyl) butanamide;

(2S,3R)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-3-hydroxy-N-methylpentanamide;

(2S,3S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-3-hydroxy-N-methylpentanamide;

(2S,3R)-1-(azetidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxypentan-1-one;

(2S,3S)-1-(azetidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxypentan-1-one;

(2S,3R)—N-(cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N-methylpentanamide;

(2S,3S)—N-(cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N-methylpentanamide;

(2S,3R)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-3-hydroxy-N-methyl-4-phenylbutanamide;

(2S,3S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-3-hydroxy-N-methyl-4-phenylbutanamide;

(2S,3R)-1-(azetidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-4-phenylbutan-1-one;

(2S,3S)-1-(azetidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-4-phenylbutan-1-one;

(2S,3R)—N-(cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N-methyl-4-phenylbutanamide;

(2S,3S)—N-(cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N-methyl-4-phenylbutanamide;

(S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxy-1-(methylsulfonyl) piperidin-4-yl)-N-methylacetamide;

(S)-2-(1-(cyclopropylsulfonyl)-4-hydroxypiperidin-4-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-N-methylacetamide;

Methyl 4-((S)-1-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(ethyl(methyl)amino)-2-oxoethyl)-4-hydroxypiperidine-1-carboxylate;

(2S,3R)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-3-hydroxy-N-methyl-3-(1-methyl-1H-pyrazol-3-yl)propanamide;

(2S,3S)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-3-hydroxy-N-methyl-3-(1-methyl-1H-pyrazol-3-yl)propanamide;

(2S,3R)-1-1-(Azetidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-(1-methyl-1H-pyrazol-3-yl) propan-1-one;

(2S,3S)-1-(Azetidin-1-yl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-3-(1-methyl-1H-pyrazol-3-yl) propan-1-one;

(2S,3R)—N-(cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N-methyl-3-(1-methyl-1H-pyrazol-3-yl) propanamide;

(2S,3S)—N-(cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-3-hydroxy-N-methyl-3-(1-methyl-1H-pyrazol-3-yl) propanamide;

(S)—N-Cyclopropyl-4-(1-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(ethyl(methyl)amino)-2-oxoethyl)-4-hydroxypiperidine-1-carboxamide;

(S)—N-(Cyclopropylmethyl)-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxytetrahydro-2H-pyran-4-yl)acetamide;

(S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(oxetan-3-yl)acetamide;

(2R,3R,4S,5R,6S)-2-(Acetoxymethyl)-6-(((S)-2-(ethyl(methyl)amino)-1-(3-hydroxy-1-(methoxycarbonyl)azetidin-3-yl)-2-oxoethyl)thio)-4-(4-(3,4,5-trifluorophenyl)-1H-1,2,3-triazol-1-yl)tetrahydro-2H-pyran-3,5-diyl diacetate;

N-Cyclopropyl-4-((S)-2-(ethyl(methyl)amino)-1-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-oxoethyl)-4-hydroxypiperidine-1-carboxamide;

(S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxytetrahydro-2H-pyran-4-yl)-N-phenylacetamide;

(S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-phenylacetamide;

(S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(pyridin-2-yl)acetamide;

(S)-2-(((2S,3R,4S,5R,6R)-3,5-Dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methyl-N-(pyridin-3-yl)acetamide;

(S)-2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methyl-N-(pyridin-2-yl)acetamide;

(S)—N-Cyclobutyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-N-ethyl-2-(4-hydroxytetrahydro-2H-pyran-4-yl)acetamide;

(S)—N-Cyclobutyl-2-(((2S,3R,4S,5R,6R)-3,5-dihydroxy-6-(hydroxymethyl)-4-(4-(3,4,5-trifluorophenyl)-1H-1,2,3-triazol-1-yl)tetrahydro-2H-pyran-2-yl)thio)-2-(4-hydroxytetrahydro-2H-pyran-4-yl)-N-methylacetamide;

(S)—N-Cyclopropyl-2-(4,4-difluoro-1-hydroxycyclohexyl)-N-ethyl-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide;

(S)—N-(Cyclopropylmethyl)-2-(4,4-difluoro-1-hydroxycyclohexyl)-N-ethyl-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide;

(S)-2-(4,4-Difluoro-1-hydroxycyclohexyl)-N-ethyl-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-((tetrahydro-2H-pyran-4-yl)methyl)acetamide;

(S)—N-Benzyl-2-(4,4-difluoro-1-hydroxycyclohexyl)-N-ethyl-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide;

(S)-2-(4,4-Difluoro-1-hydroxycyclohexyl)-N-((3,3-difluorocyclobutyl)methyl)-N-ethyl-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide;

(S)-2-(4,4-Difluoro-1-hydroxycyclohexyl)-N-ethyl-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-(tetrahydro-2H-pyran-4-yl)acetamide;

(S)-2-(((2S,3R,4S,5R,6R)-4-(4-(3,5-Difluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

(S)—N-Ethyl-2-(((2S,3R,4S,5R,6R)-4-(4-(3-fluorophenyl)-1H-1,2,3-triazol-1-yl)-3,5-dihydroxy-6-(hydroxymethyl)tetrahydro-2H-pyran-2-yl)thio)-2-(4-hydroxytetrahydro-2H-pyran-4-yl)-N-methylacetamide;

(S)-2-(((2S,3R,4S,5R,6R)-4-(4-(3,5-Difluoro-4-methylphenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

(S)-2-(((2S,3R,4S,5R,6R)-4-(4-(4-Chloro-3,5-difluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

(S)-2-(((2S,3R,4S,5R,6R)-4-(4-(4-Bromothiazol-2-yl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

(S)-2-(((2S,3R,4S,5R,6R)-4-(4-(4-Bromo-3-fluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

(S)-2-(((2S,3R,4S,5R,6R)-4-(4-(3-Chloro-5-fluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

(S)-2-(((2S,3R,4S,5R,6R)-4-(4-(3-Chloro-4,5-difluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

(S)-2-(((2S,3R,4S,5R,6R)-4-(4-(3,4-Difluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

(S)-2-(((2S,3R,4S,5R,6R)-4-(4-(3,4-Dichloro-5-fluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

(S)-2-(((2S,3R,4S,5R,6R)-4-(4-(4-Bromo-3,5-difluorophenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

(S)-2-(((2S,3R,4S,5R,6R)-4-(4-(3-Cyano-5-methylphenyl)-1H-1,2,3-triazol-1-yl)-3,5-dihydroxy-6-(hydroxymethyl)tetrahydro-2H-pyran-2-yl)thio)-N-ethyl-2-(4-hydroxytetrahydro-2H-pyran-4-yl)-N-methylacetamide;

(S)—N-Ethyl-2-(((2S,3R,4S,5R,6R)-4-(4-(3-fluoro-5-methylphenyl)-1H-1,2,3-triazol-1-yl)-3,5-dihydroxy-6-(hydroxymethyl)tetrahydro-2H-pyran-2-yl)thio)-2-(4-hydroxytetrahydro-2H-pyran-4-yl)-N-methylacetamide;

(S)—N-Cyclopropyl-2-(4,4-difluoro-1-hydroxycyclohexyl)-2-(((2S,3R,4S,5R,6R)-4-(4-(6-fluoro-5-methylpyridin-3-yl)-1H-1,2,3-triazol-1-yl)-3,5-dihydroxy-6-(hydroxymethyl)tetrahydro-2H-pyran-2-yl)thio)-N-methylacetamide;

(S)-2-(4,4-Difluoro-1-hydroxycyclohexyl)-N-(2-fluoro-2-methylpropyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide;

(S)-2-(4,4-Difluoro-1-hydroxycyclohexyl)-1-(4,4-difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio) ethan-1-one;

(S)—N-(Cyclopropylmethyl)-2-(4,4-difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide;

(S)-2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N,N-dimethylacetamide;

(S)-2-(4,4-Difluoro-1-hydroxycyclohexyl)-N-ethyl-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide;

(S)-2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methyl-N-(2,2,2-trifluoroethyl)acetamide;

(S)-2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-isopropyl-N-methylacetamide;

(S)-2-(4,4-Difluoro-1-hydroxycyclohexyl)-N-(3,3-dimethylbutyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide;

(S)—N-(2-Cyclopropylethyl)-2-(4,4-difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide;

(S)-2-(4,4-Difluoro-1-hydroxycyclohexyl)-N-(3,3-difluorocyclobutyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide;

(S)-2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methyl-N-(oxetan-3-yl)acetamide;

(S)-2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methyl-N-(tetrahydro-2H-pyran-4-yl)acetamide;

(S)-2-(4,4-Difluoro-1-hydroxycyclohexyl)-2-(((2S,3R,4S,5R,6R)-5-hydroxy-6-(hydroxymethyl)-3-methoxy- 4-(4-(3,4,5-trifluorophenyl)-1H-1,2,3-triazol-1-yl)tetrahydro-2H-pyran-2-yl)thio)-1-morpholinoethan-1-one;

(S)-2-(4,4-Difluoro-1-hydroxycyclohexyl)-1-(4,4-dimethylpiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio) ethan-1-one;

(S)-2-(4,4-Difluoro-1-hydroxycyclohexyl)-N-(4,4-dimethylcyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide;

(S)—N-(Bicyclo[1.1.1]pentan-1-yl)-2-(4,4-difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide;

(S)-2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-methylacetamide;

(S)-2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-(tetrahydro-2H-pyran-4-yl)acetamide;

(S)-2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-(pentan-3-yl)acetamide;

(S)-2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-isopropylacetamide;

(S)-2-(4,4-Difluoro-1-hydroxycyclohexyl)-N-(3,3-dimethylbutyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide;

(S)-2-(4,4-Difluoro-1-hydroxycyclohexyl)-N-(3,3-difluorocyclobutyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide;

(S)-2-(4,4-Difluoro-1-hydroxycyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-N-(2,2,2-trifluoroethyl)acetamide;

(S)-2-(4,4-Difluoro-1-hydroxycyclohexyl)-N-(4,4-dimethylcyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)acetamide;

(S)-1-(4,4-Difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-(6-hydroxyspiro[2.5]octan-6-yl)ethan-1-one;

(S)-1-(4,4-Difluoropiperidin-1-yl)-2-(1-hydroxy-4,4-dimethylcyclohexyl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio) ethan-1-one;

(S)-1-(4,4-Difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-(7-hydroxyspiro[3.5]nonan-7-yl)ethan-1-one;

(S)-1-(4,4-Difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-(7-hydroxy-2-oxaspiro[3.5]nonan-7-yl)ethan-1-one;

(S)-1-(4,4-Difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-(8-hydroxyspiro[4.5]decan-8-yl)ethan-1-one;

(S)-1-(4,4-Difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio)-2-(9-hydroxy-3-oxaspiro[5.5]undecan-9-yl)ethan-1-one;

(S)-1-(4,4-Difluoropiperidin-1-yl)-2-((R)-4-hydroxy-2,2-dimethyltetrahydro-2H-pyran-4-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio) ethan-1-one;

(S)-1-(4,4-Difluoropiperidin-1-yl)-2-((S)-4-hydroxy-2,2-dimethyltetrahydro-2H-pyran-4-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio) ethan-1-one;

(2S)-2-(1,1-Difluoro-6-hydroxyspiro[2.5]octan-6-yl)-1-(4,4-difluoropiperidin-1-yl)-2-(((2S,3R,4S,5R,6R)-5-hydroxy-6-(hydroxymethyl)-3-methoxy-4-(4-(3,4,5-trifluorophenyl)-1H-1,2,3-triazol-1-yl)tetrahydro-2H-pyran-2-yl)thio) ethan-1-one; or (S)-2-(4,4-Difluoro-1-hydroxycyclohexyl)-1-(4,4-difluoropiperidin-1-yl)-2-(((2S,3R,4S,5R,6R)-3-ethoxy-5-hydroxy-6-(hydroxymethyl)-4-(4-(3,4,5-trifluorophenyl)-1H-1,2,3-triazol-1-yl)tetrahydro-2H-pyran-2-yl) thio) ethan-1-one;

or a pharmaceutically acceptable salt thereof.

14. A pharmaceutical composition comprising a compound according to claim 13, or a pharmaceutically acceptable salt thereof, and a pharmaceutically acceptable carrier.

15. A method for the treatment of an indication mediated by galectin-3 selected from fibrosis of organs; neuropathic pain; insulin resistance disorders, and cancer wherein the cancer is treated in combination with immunotherapy, comprising administering to a subject in a need thereof an effective amount of a compound according to claim 13, or of a pharmaceutically acceptable salt thereof.

* * * * *